(12) United States Patent
Quader et al.

(10) Patent No.: US 10,441,662 B2
(45) Date of Patent: Oct. 15, 2019

(54) POLYMER, METHOD FOR PRODUCING POLYMER, AND DRUG CONJUGATE

(71) Applicant: Kawasaki Institute of Industrial Promotion, Kawasaki-shi, Kanagawa (JP)

(72) Inventors: Sabina Quader, Kawasaki (JP); Horacio Cabral, Tokyo (JP); Hiroaki Kinoh, Kawasaki (JP); Kazunori Kataoka, Kawasaki (JP)

(73) Assignee: Kawasaki Institute of Industrial Promotion, Kawasaki-shi, Kanagawa (JP)

( * ) Notice: Subject to any disclaimer, the term of this patent is extended or adjusted under 35 U.S.C. 154(b) by 0 days.

(21) Appl. No.: 16/326,837

(22) PCT Filed: Aug. 23, 2017

(86) PCT No.: PCT/JP2017/030150
§ 371 (c)(1),
(2) Date: Feb. 20, 2019

(87) PCT Pub. No.: WO2018/038165
PCT Pub. Date: Mar. 1, 2018

(65) Prior Publication Data
US 2019/0192671 A1      Jun. 27, 2019

(30) Foreign Application Priority Data

Aug. 23, 2016 (JP) .................................. 2016-163134

(51) Int. Cl.
*A61K 47/59* (2017.01)
*A61K 47/69* (2017.01)
*A61P 35/00* (2006.01)

(52) U.S. Cl.
CPC .......... *A61K 47/59* (2017.08); *A61K 47/6907* (2017.08); *A61P 35/00* (2018.01)

(58) Field of Classification Search
CPC ...... A61K 47/59; A61K 47/6907; A61P 35/00
See application file for complete search history.

(56) References Cited

U.S. PATENT DOCUMENTS

2007/0059271 A1* 3/2007 Kataoka

FOREIGN PATENT DOCUMENTS

| EP | 0243929 A2 | 11/1987 |
|---|---|---|
| JP | 62-267300 A | 11/1987 |
| JP | 01-256530 A | 10/1989 |
| JP | 06-321999 A | 11/1994 |

OTHER PUBLICATIONS

International Search Report dated Nov. 7, 2017 in connection with PCT/JP2017/030150.
Huang et al., Synthesis of Aldehyde Functionalized and Degradable Block Copolymers and Their Bioconjugation. Acta Polymerica Sinica. 2015;(4):459-65. 10.11777/j.issn1000-3304.2015.14322.
Hwang et al., Well-defined polymers with activated ester and protected aldehyde side chains for bio-functionalization. J Control Release. Oct. 8, 2007;122(3):279-86. Epub Apr. 21, 2007.
Liu et al., Synthesis of functional core, star polymers via RAFT polymerization for drug delivery applications. Macromol Rapid Commun. May 14, 2012;33(9):760-6. doi: 10.1002/marc.201200029. Epub Apr. 12, 2012.
Xiao et al., A Well-Defined Novel Aldehyde-Functionalized Glycopolymer: Synthesis, Micelle Formation, and Its Protein Immobilization. Macromolecules. 2008;41(7):2374-80. doi: 10.1021/ma702510n.

\* cited by examiner

*Primary Examiner* — Alma Pipic
(74) *Attorney, Agent, or Firm* — Wolf, Greenfield & Sacks, P.C.

(57) ABSTRACT

Provided is a polymer including a repeating unit (I) represented by Formula (I) and a repeating unit (II) represented by Formula (II) (in the formulae, m represents 1 or 2, L represents a divalent aromatic hydrocarbon group or a divalent aliphatic hydrocarbon group, $R^1$ represents a hydrogen atom, an aliphatic hydrocarbon group, or an aromatic hydrocarbon group, X represents $OR^x$, $SR^x$, or $NR^{x1}R^{x2}$, $R^x$ represents a hydrogen atom, an aliphatic hydrocarbon group, or an aromatic hydrocarbon group, $R^{x1}$ and $R^{x2}$ each independently represent a hydrogen atom, an aliphatic hydrocarbon group, or an aromatic hydrocarbon group).

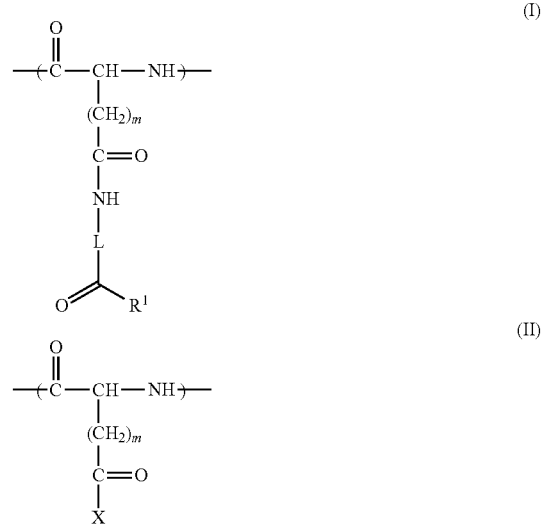

12 Claims, 44 Drawing Sheets

FIG. 42

| Name | % | Name | % | Name | % |
|---|---|---|---|---|---|
| AXL (R499C) | 24.82 | FGFR2 (K526E) | 27.97 | RET (E762Q) | 20.04 |
| | | FGFR2 (K659N) | 29.64 | RET (G691S) | 26.22 |
| CHK2 (I157T) | 14.78 | FGFR2 (V564F) | 17.86 | RET (L790F) | 23.19 |
| | | FLT3 (D835Y) | 3.04 | RET (M918T) | 25.50 |
| c-Kit (A829P) | 15.61 | FLT3 (F594_R595insR) | -1.84 | RET (R749T) | 6.58 |
| c-Kit (d557-558) | 22.96 | FLT3 (F594_R595insREY) | -0.36 | RET (R813Q) | 25.66 |
| c-Kit (D816E) | 17.55 | FLT3 (ITD) | 2.56 | RET (S891A) | 12.82 |
| c-Kit (D816F) | 18.24 | FLT3 (ITD)-NPOS | -0.47 | RET (S904A) | 18.29 |
| c-Kit (D816H) | 11.35 | FLT3 (ITD)-W51 | -1.19 | RET (S904F) | 15.33 |
| c-Kit (D816I) | 9.82 | FLT3 (R595_E596insEY) | 0.62 | RET (V778I) | 20.28 |
| c-Kit (D816V) | 7.87 | FLT3 (Y591-V592insVDFREYEYD) | 0.57 | RET (V804L) | 24.33 |
| c-Kit (D816Y) | 11.63 | JAK2 (V617F) | 8.17 | RET (V804M) | 5.76 |
| c-Kit (D820Y) | 17.00 | LRRK2 (G2019S) | -0.84 | RET (Y791F) | 11.95 |
| c-Kit (V559A) | 15.34 | LRRK2 (I2020T) | -0.40 | RET-BCR | 21.03 |
| c-Kit (V559D/T670I) | 16.92 | LRRK2 (R1441C) | -0.22 | RET-CCDC6 (PTC1) | 16.59 |
| c-Kit (V560G) | 27.15 | MELK (T460M) | 6.03 | RET-NCOA4 (PTC3) | 19.00 |
| c-Kit (V560G/D816V) | 10.85 | PDGFRa (D842V) | 22.65 | RET-PRKAR1A (PTC2) | 18.59 |
| c-Kit (V560G/N822K) | 15.63 | PDGFRa (T674I) | 6.24 | ROS1-GOPC | 1.68 |
| DDR2 (T654M) | 8.53 | PKD2 (G870E) | 0.55 | ROS1-TPM3 | 22.55 |
| | | | | RSK2 (I416V) | 5.07 |
| EGFR (d746-750/T790M/C797S) | 28.88 | | | RSK2 (L608F) | 8.20 |
| | | | | TRKA (G667C) | -1.16 |
| FGFR2 (K526E) | 27.97 | | | TRKA-TFG (TRK-T3) | -3.68 |
| | | | | TRKA-TPM3 | -0.70 |
| | | | | TRKA-TPR | -2.66 |

POLYMER, METHOD FOR PRODUCING POLYMER, AND DRUG CONJUGATE

CROSS-REFERENCE TO RELATED APPLICATIONS

This Application is a National Stage filing under 35 U.S.C. 371 of International Patent Application Serial No. PCT/JP2017/030150, filed Aug. 23, 2017, which claims foreign priority benefits under 35 U.S.C. § 119(a)-(d) or 35 U.S.C. § 365(b) of Japanese Application Number 2016-163134, filed Aug. 23, 2016. The entire contents of these applications are incorporated herein by reference in their entirety.

TECHNICAL FIELD

The present invention relates to a polymer, a method for producing a polymer, and a drug conjugate.

BACKGROUND ART

A polymer containing an aldehyde group or a ketone group (hereinafter, also referred to as an "aldehyde/ketone-containing polymer") can be used for bonding a bioactive molecule containing a functional group such as an amino group, an imino group, or a hydrazide group by forming a pH sensitive Schiff base.

Further, the aldehyde group-containing polymer can also be used for core crosslinking of cationic polypeptides. Therefore, the aldehyde/ketone-containing polymer has been attracting attention particularly in the pharmaceutical field as a carrier that delivers a drug.

A method of introducing an aldehyde to a polymer, a method of performing RAFT polymerization on 4-vinylbenzaldehyde to obtain an aldehyde-introduced polymer has been known (for example, NPLs 1 to 4).

CITATION LIST

Non-Patent Literature

[NPL 1] Synthesis of Aldehyde functionalized and degradable block copolymer and their bioconjugation. Jianbing Huang, Zhong-peng Xiao, Hui Liang, Jiang Lu, Acta Polymerica SInica, 2015, issue 4, 459 to 465

[NPL 2] Synthesis of Functional Core, Star Polymers via RAFT Polymerization for Drug Delivery Applications. Jinna Liu, Hien Duong, Michael R. Whittaker, Thomas P. Davis, Cyrille Boyer, Macromolecular Rapid Communications, Volume 33, Issue 9 Pages, 760 to 766

[NPL 3] A Well-Defined Novel Aldehyde-Functionalized Glycopolymer: Synthesis, Micelle Formation, and Its Protein Immobilization. Nai-Yu Xiao, An-Long Li, Hui Liang, and Jiang Lu, Macromolecules, 2008, 41, 2374 to 2380.

[NPL 4] Well-defined polymers with activated ester and protected aldehyde side chains for bio-functionalization. Jungyeon Hwang, Ronald C. Li, Heather D. Maynard, Journal of Controlled Release 122 (2007) 279 to 286

SUMMARY OF INVENTION

Technical Problem

However, in the methods of NPLs 1 to 4, there is a problem in that an aliphatic aldehyde, an aromatic aldehyde, an aliphatic ketone, and an aromatic ketone cannot be selectively introduced because only an aromatic aldehyde can be introduced. Further, in the methods of NPLs 1 to 4, there is also another problem in that a reaction step becomes complicated in a case where other functional groups are introduced because only a homopolymer can be obtained due to the RAFT polymerization.

In NPL 4, acetal group-introduced methacrylate is used. However, since the acetal group-introduced methacrylate is bonded to a base polymer through an ester bond, dissociation from the base polymer occurs at a physiological pH (pH of 7.4). Accordingly, the acetal group-introduced methacrylate is not suitable for drug delivery.

The present invention has been made in consideration of the above-described circumstances, and an object thereof is to provide a novel polymer, a method for producing the polymer, and a drug conjugate containing the polymer.

Solution to Problem

In order to solve the above-described problems, the present invention employs the following configurations.

(1) A polymer including: a repeating unit (I) represented by Formula (I); and a repeating unit (II) represented by Formula (II).

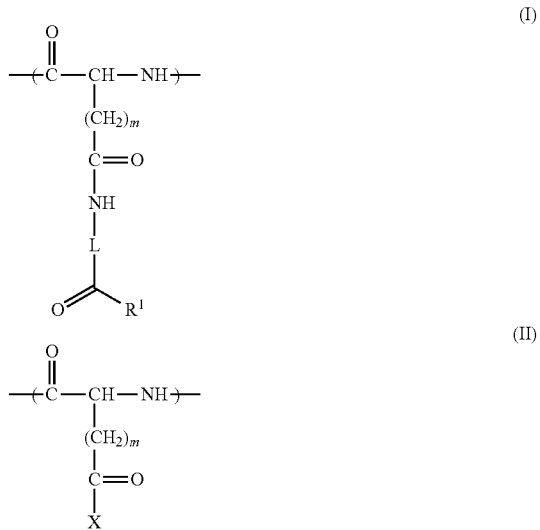

[In the formulae, m represents 1 or 2, L represents a divalent aromatic hydrocarbon group or a divalent aliphatic hydrocarbon group, $R^1$ represents a hydrogen atom, an aliphatic hydrocarbon group, or an aromatic hydrocarbon group, X represents $OR^x$, $SR^x$, or $NR^{x1}R^{x2}$, $R^x$ represents a hydrogen atom, an aliphatic hydrocarbon group, or an aromatic hydrocarbon group, $R^{x1}$ and $R^{x2}$ each independently represent a hydrogen atom, an aliphatic hydrocarbon group, or an aromatic hydrocarbon group.]

(2) A method for producing a polymer, including: a step (1) of reacting a polymer (P1) which has a repeating unit (II') represented by Formula (II') with a compound (1a) represented by Formula (1a) to obtain a polymer (P2) which has a repeating unit represented by Formula (I') and the repeating unit (II'); and a step (2) of hydrolyzing the polymer (P2) under a neutral condition or a weakly acidic condition to obtain a polymer which has a repeating unit (I) represented by Formula (I) and a repeating unit (II-1) represented by Formula (II-1).

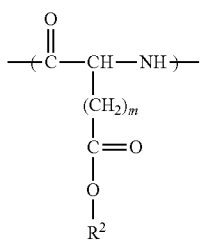
(II')

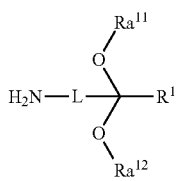
(1a)

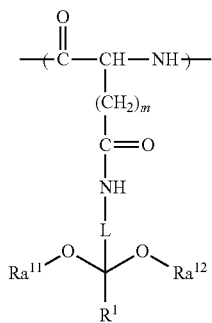
(I')

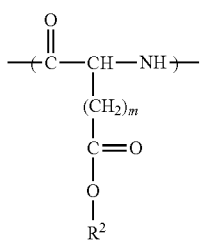
(II')

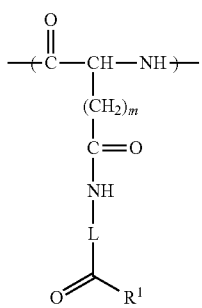
(II-1)

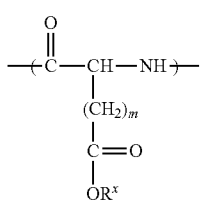

[In the formulae, m represents 1 or 2, $R^2$ represents a hydrogen atom, an aliphatic hydrocarbon group, or an aromatic hydrocarbon group, L represents a divalent aromatic hydrocarbon group, or a divalent aliphatic hydrocarbon group, $R^1$ represents a hydrogen atom, an aliphatic hydrocarbon group, or an aromatic hydrocarbon group, $Ra^{11}$ and $Ra^{12}$ each independently represent a methyl group or an ethyl group or $Ra^{11}$ and $Ra^{12}$ are bonded to each other and represent an ethylene group or a propylene group, and $R^x$ represents a hydrogen atom, an aliphatic hydrocarbon group, or an aromatic hydrocarbon group.]

(3) A method for producing a polymer, including: a step (1) of reacting a polymer (P1) which has a repeating unit (II') represented by Formula (II') with a compound (1a) represented by Formula (1a) to obtain a polymer (P2) which has a repeating unit represented by Formula (I') and the repeating unit (II'); a step (2a) of applying at least one treatment selected from the group consisting of hydrolysis under an alkaline condition, a transesterification reaction, aminolysis, and hydrolysis and amide coupling under an alkaline condition to the polymer (P2) to obtain a polymer (P3) which has a repeating unit (I') represented by Formula (I') and a repeating unit (II') represented by Formula (II'); and a step (2b) of hydrolyzing the polymer (P3) under a neutral condition or a weakly acidic condition to obtain a polymer which has a repeating unit (I) represented by Formula (I) and a repeating unit (II) represented by Formula (II).

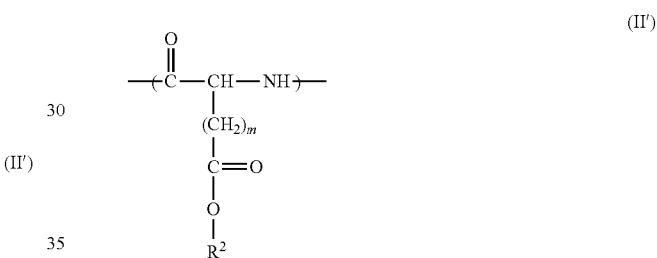
(II')

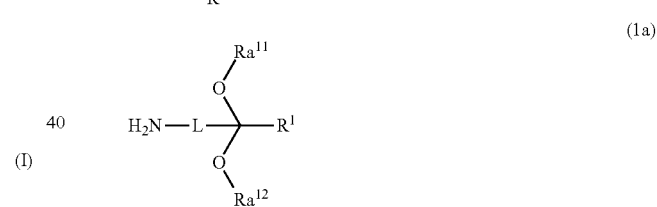
(1a)

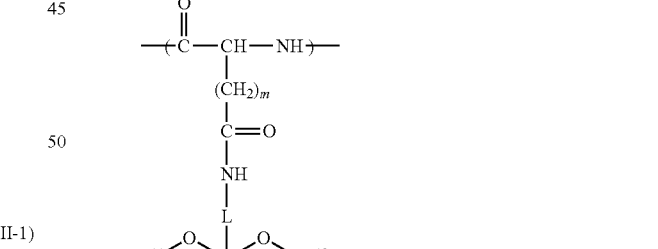
(I')

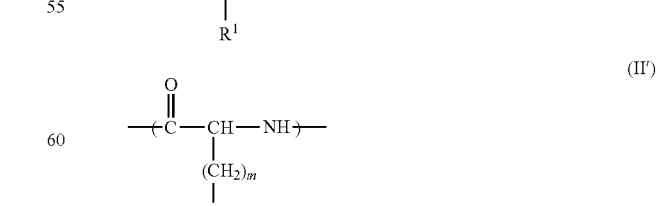
(II')

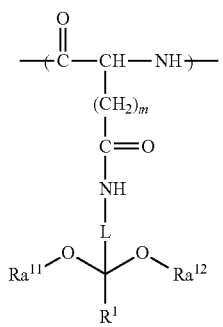

(I')

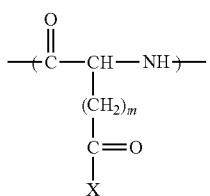

(II)

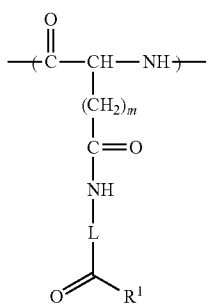

(I)

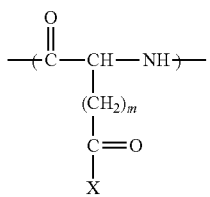

(II)

[In the formulae, m represents 1 or 2, $R^2$ represents a hydrogen atom, an aliphatic hydrocarbon group, or an aromatic hydrocarbon group, L represents a divalent aromatic hydrocarbon group, or a divalent aliphatic hydrocarbon group, $R^1$ represents a hydrogen atom, an aliphatic hydrocarbon group, or an aromatic hydrocarbon group, $Ra^{11}$ and $Ra^{12}$ each independently represent a methyl group or an ethyl group or $Ra^{11}$ and $Ra^{12}$ are bonded to each other and represent an ethylene group or a propylene group, X represents $OR^x$, $SR^x$, or $NR^{x1}R^{x2}$, $R^x$ represents a hydrogen atom, an aliphatic hydrocarbon group, or an aromatic hydrocarbon group, and $R^{x1}$ and $R^{x2}$ each independently represent a hydrogen atom, an aliphatic hydrocarbon group, or an aromatic hydrocarbon group.]

(4) A drug conjugate including: the polymer according to (1); and at least one drug bonded to the polymer.

(5) The drug conjugate according to (4), further including: a polymer which includes a repeating unit (Ia) represented by Formula (Ia) and a repeating unit (II) represented by Formula (II).

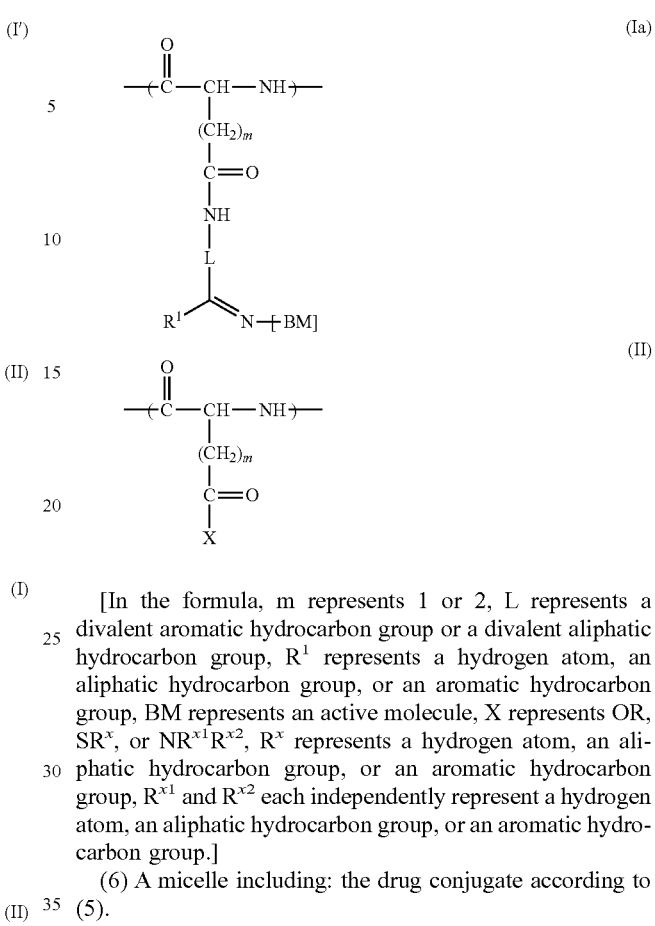

[In the formula, m represents 1 or 2, L represents a divalent aromatic hydrocarbon group or a divalent aliphatic hydrocarbon group, $R^1$ represents a hydrogen atom, an aliphatic hydrocarbon group, or an aromatic hydrocarbon group, BM represents an active molecule, X represents OR, $SR^x$, or $NR^{x1}R^{x2}$, $R^x$ represents a hydrogen atom, an aliphatic hydrocarbon group, or an aromatic hydrocarbon group, $R^{x1}$ and $R^{x2}$ each independently represent a hydrogen atom, an aliphatic hydrocarbon group, or an aromatic hydrocarbon group.]

(6) A micelle including: the drug conjugate according to (5).

Advantageous Effects of Invention

According to the present invention, it is possible to provide a novel polymer to which an aliphatic aldehyde and an aromatic aldehyde have been selectively introduced, a method for producing the polymer, and a drug conjugate obtained by bonding a drug to the polymer.

BRIEF DESCRIPTION OF DRAWINGS

FIG. 42 shows a list of mutant kinases obtained by suppressing the kinase activity to less than or equal to 30% using K252a-H.

DESCRIPTION OF EMBODIMENTS

Figure 1:
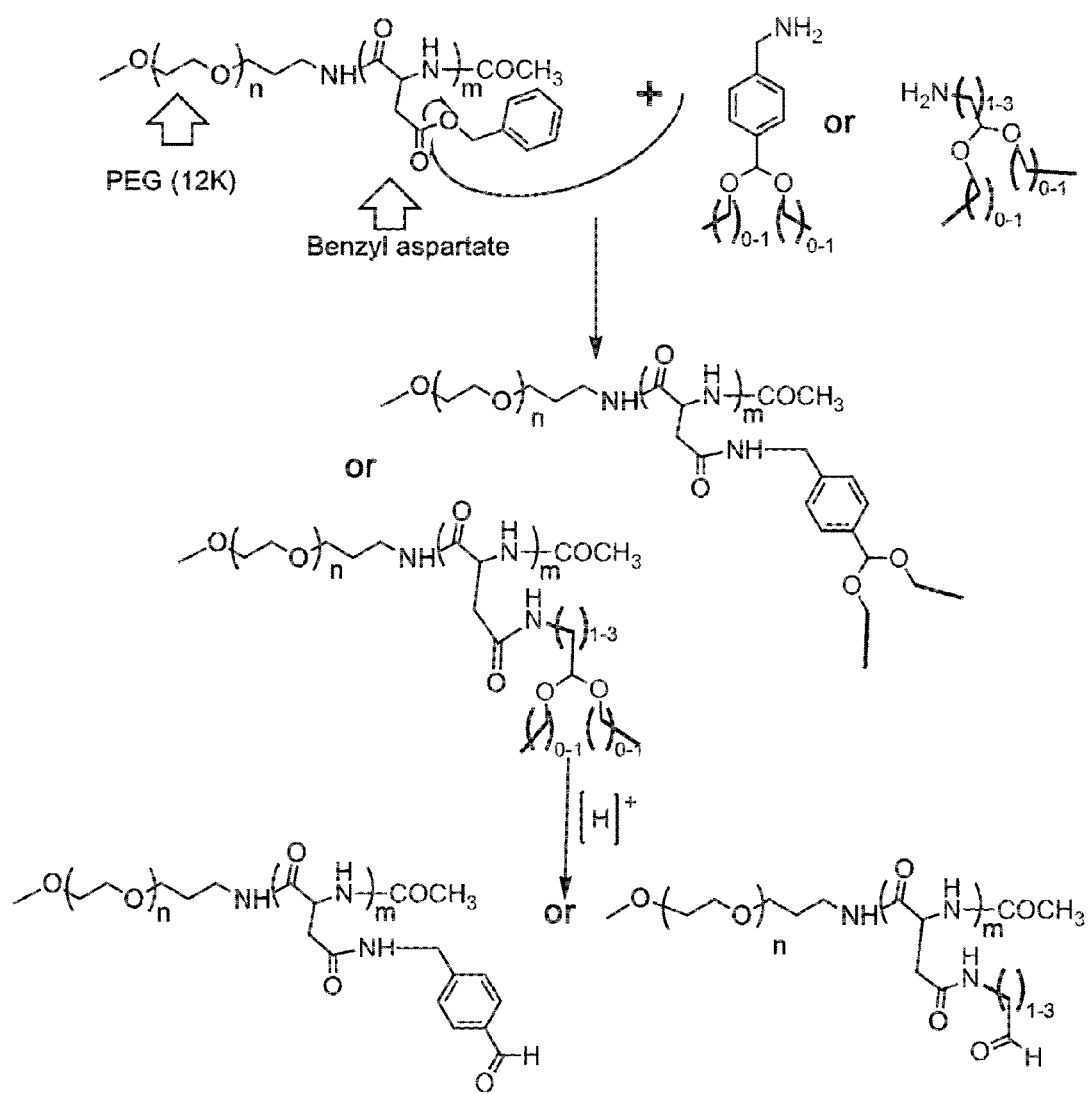
FIG. 1 shows a scheme for synthesizing an aromatic aldehyde group-containing polymer and an aliphatic aldehyde group-containing polymer according to an embodiment of the present invention.

[First Embodiment]
<Polymer>

A polymer according to the present embodiment has a repeating unit (I) represented by Formula (I) and a repeating unit (II) represented by Formula (II).

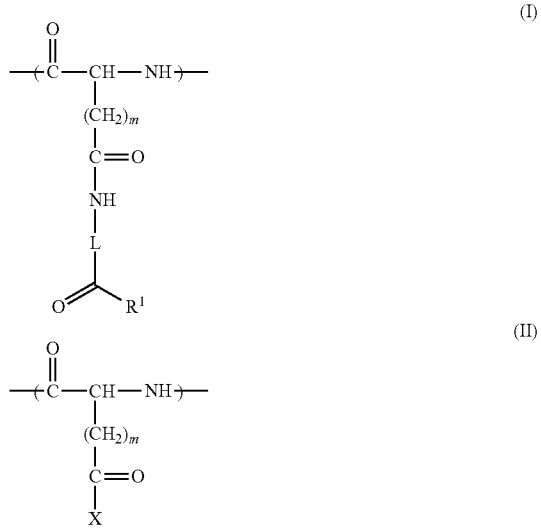

[In the formulae, m represents 1 or 2. L represents a divalent aromatic hydrocarbon group or a divalent aliphatic hydrocarbon group. $R^1$ represents a hydrogen atom, an aliphatic hydrocarbon group, or an aromatic hydrocarbon group. X represents $OR^x$, $SR^x$, or $NR^{x1}R^{x2}$. $R^x$ represents a hydrogen atom, an aliphatic hydrocarbon group, or an aromatic hydrocarbon group. $R^{x1}$ and $R^{x2}$ each independently represent a hydrogen atom, an aliphatic hydrocarbon group, or an aromatic hydrocarbon group.]

In Formulae (I) and (II), m represents 1 or 2 and preferably 1.

In Formula (I), L represents a divalent aromatic hydrocarbon group or a divalent aliphatic hydrocarbon group.

Examples of the divalent aromatic hydrocarbon group as L include a phenylene group and a benzylene group.

The divalent aromatic hydrocarbon group as L may have a substituent.

Examples of the substituent include a methyl group, an ethyl group, a propyl group, an isopropyl group, a tert-butyl group, a nitro group, and a halide.

Examples of the divalent aliphatic hydrocarbon group as L include an ethylene group, a propylene group, a butylene group, and a pentylene group. The divalent aliphatic hydrocarbon group as L may include a substituent.

Examples of the substituent include a methyl group, an ethyl group, a propyl group, an isopropyl group, a butyl group, a tert-butyl group, a nitro group, and a halide.

Among these, L represents preferably a methylene group, an ethylene group, a propylene group, or a benzylene group and more preferably a methylene group, an ethylene group, or a benzylene group.

In Formula (I), $R^1$ represents a hydrogen atom, an aliphatic hydrocarbon group, or an aromatic hydrocarbon group.

Examples of the aliphatic hydrocarbon group as $R^1$ include an ethyl group, a propyl group, a butyl group, and a pentyl group. The aliphatic hydrocarbon group as $R^1$ may have a substituent. Examples of the substituent include a methyl group, an ethyl group, a propyl group, an isopropyl group, a butyl group, an isobutyl group, a tert-butyl group, a pentyl group, an isopentyl group, a tert-pentyl group, a cyclohexyl group, and a trihalomethyl group.

Examples of the aromatic hydrocarbon group as $R^1$ include a phenyl group, a benzyl group, a pyridyl group, a naphthyl group, a hydroxyphenyl group, a methoxyphenyl group, an ethoxyphenyl group, a xylyl group, a methylphenyl group, a nitrophenyl group, a chlorophenyl group, a fluorophenyl group, an iodophenyl group, and a bromophenyl group.

Among these, $R^1$ represents preferably a hydrogen atom or an aliphatic hydrocarbon group and more preferably a hydrogen atom or a methyl group.

In Formula (I), X represents $OR^x$, $SR^x$, or $NR^{x1}R^{x2}$.

In Formula (I), Rx represents a hydrogen atom, an aliphatic hydrocarbon group, or an aromatic hydrocarbon group. Examples of the aliphatic hydrocarbon group as $R^x$ include a methyl group, an ethyl group, a propyl group, an isopropyl group, a butyl group, an isobutyl group, a tert-butyl group, a pentyl group, an isopentyl group, a tert-pentyl group, a cyclohexyl group, and a trifluoromethyl group.

Examples of the aromatic hydrocarbon group as Rx include a phenyl group, a benzyl group, a pyridyl group, a naphthyl group, a hydroxyphenyl group, a methoxyphenyl group, an ethoxyphenyl group, a xylyl group, a methylphenyl group, a nitrophenyl group, a chlorophenyl group, a fluorophenyl group, an iodophenyl group, and a bromophenyl group.

$R^{x1}$ and $R^{x2}$ each independently represent a hydrogen atom, an aliphatic hydrocarbon group, or an aromatic hydrocarbon group.

Examples of the aliphatic hydrocarbon group as $R^{x1}$ and $R^{x2}$ include a methyl group, an ethyl group, an isopropyl group, a butyl group, an isobutyl group, a tert-butyl group, a pentyl group, an isopentyl group, a tert-pentyl group, a cyclohexyl group, and a trihalomethyl group.

Examples of the aromatic hydrocarbon group as $R^{x1}$ and $R^{x2}$ include a phenyl group, a benzyl group, a pyridyl group, a naphthyl group, a hydroxyphenyl group, a methoxyphenyl group, an ethoxyphenyl group, a xylyl group, a methylphenyl group, a nitrophenyl group, a chlorophenyl group, a fluorophenyl group, an iodophenyl group, and a bromophenyl group.

Among these, X represents preferably OR$^x$ and more preferably OH (a hydroxy group).

The polymer according to the present embodiment may have repeating units (hereinafter, also referred to as a "repeating unit (III)") other than the repeating units (I) and (II).

As the repeating unit (III), a hydrophilic repeating unit is preferable, and examples thereof include a repeating unit derived from polyethylene glycol, a repeating unit derived from poly(ethylethylenephosphate), a repeating unit derived from polyvinyl alcohol, a repeating unit derived from polyvinylpyrrolidone, a repeating unit derived from poly(oxazoline), and a repeating unit derived from poly(N-(2-hydroxypropyl)methacrylamide) (PHPMA). Among these, as the repeating unit (III), a repeating unit derived from polyethylene glycol is preferable.

In the present embodiment, the content of the repeating units (I) to (III) is not particularly limited.

The content of the repeating unit (I) is preferably in a range of 5% to 100% by mole, more preferably in a range of 10% to 80% by mole, and still more preferably in a range of 20% to 50% by mole with respect to the total amount (100% by mole) of all repeating units constituting the polymer.

The content of the repeating unit (II) is preferably in a range of 0% to 80% by mole, more preferably in a range of 10% to 60% by mole, and still more preferably in a range of 20% to 40% by mole with respect to the total amount (100% by mole) of all repeating units constituting the polymer.

The content of the repeating unit (III) is preferably in a range of 0% to 95% by mole, more preferably in a range of 20% to 90% by mole, and still more preferably in a range of 50% to 80% by mole with respect to the total amount (100% by mole) of all repeating units constituting the polymer.

The molecular weight of the polymer according to the present embodiment is preferably in a range of 2000 to 1000000 D, more preferably in a range of 5000 to 100000 D, and still more preferably in a range of 10000 to 40000 D.

<Method (1) of Producing Polymer>

A method of producing the polymer according to the present embodiment (hereinafter, also referred to as a "production method (1)") includes a step (1) of reacting a polymer (P1) which has a repeating unit (II') represented by Formula (II') with a compound (1a) represented by Formula (1a) to obtain a polymer (P2) which has a repeating unit represented by Formula (I') and the repeating unit (II'); and a step (2) of hydrolyzing the polymer (P2) under a weakly acidic condition to obtain a polymer which has a repeating unit (I) represented by Formula (I) and a repeating unit (II-1) represented by Formula (II-1).

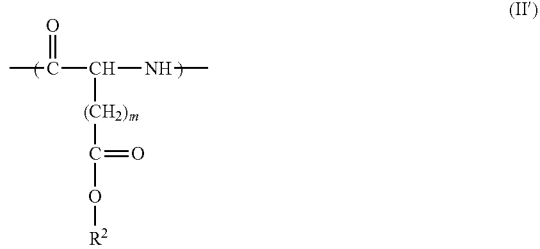

(II')

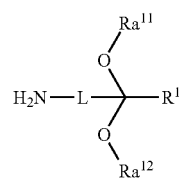

(1a)

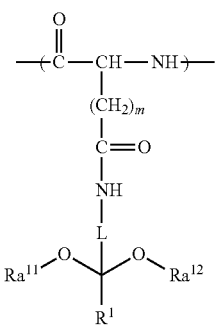

(I')

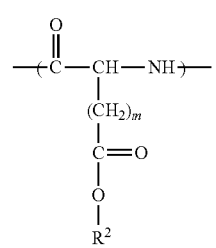

(II')

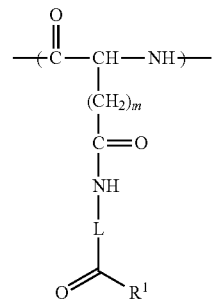

(I)

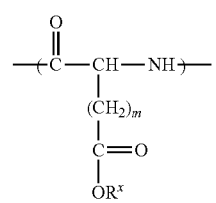

(II-1)

[In the formulae, m represents 1 or 2. $R^2$ represents a hydrogen atom, an aliphatic hydrocarbon group, or an aromatic hydrocarbon group. L represents a divalent aromatic hydrocarbon group, or a divalent aliphatic hydrocarbon group. $R^1$ represents a hydrogen atom, an aliphatic hydrocarbon group, or an aromatic hydrocarbon group. $Ra^{11}$ and $Ra^{12}$ each independently represent a methyl group or an ethyl group or $Ra^{11}$ and $Ra^{12}$ are bonded to each other and represent an ethylene group or a propylene group. $R^x$ represents a hydrogen atom, an aliphatic hydrocarbon group, or an aromatic hydrocarbon group.]

In Formulae (I'), (II'), (I), and (II-1), m, L, $R^1$, and $R^x$ each have the same definition as that for m, L, $R^1$, and $R^x$ in Formulae (I) and (II).

In Formulae (1a) and (1'), $Ra^{11}$ and $Ra^{12}$ each independently represent a methyl group or an ethyl group or $Ra^{11}$ and $Ra^{12}$ are bonded to each other and represent an ethylene group or a propylene group. In a case where $Ra^{11}$ and $Ra^{12}$ are bonded to each other and represent an ethylene group or a propylene group, the compound (1a) becomes a cyclic acetal or a cyclic ketal.

In Formula (1a), n1 and n2 each independently represent 0 or 1 and preferably 1.

(Step (1))

The step (1) of the production method (1) is an aminolysis reaction between the polymer (P1) and the compound (1a). By performing the step (1), an acetal structure or a ketal structure of the compound (1a) is introduced to a side chain of the polymer (P1).

The reaction temperature in the step (1) is not particularly limited as long as the reaction is carried out under a condition in which an acetal structure or a ketal structure of the compound (1a) is introduced to a side chain of the polymer (P1), but is typically in a range of 4° C. to 100° C. and preferably in a range of room temperature to 40° C.

The reaction time in the step (1) is not particularly limited as long as the reaction is carried out under a condition in which an acetal structure or a ketal structure of the compound (1a) is introduced to a side chain of the polymer (P1), and the reaction time can be selected depending on the amount or the kind of the compound (1a) and is typically in a range of 4 hours to 5 days.

(Step (2))

In the step (2) of the production method (1), the polymer (P2) is hydrolyzed under a neutral condition or a weakly acidic condition, and the acetal structure of the repeating unit (I') of the polymer (P2) is converted to an aldehyde or the ketal structure thereof is converted to a ketone.

The hydrolysis is not particularly limited as long as the hydrolysis is carried out under a condition in which the acetal structure of the repeating unit (I') of the polymer (P2) can be converted to an aldehyde or the ketal structure thereof can be converted to a ketone. Examples of the hydrolysis include known methods such as (i) method of performing the treatment for 30 minutes using 0.1 N hydrochloric acid, (ii) method of performing the treatment in the presence of acetone and indium (III) trifluoromethanesulfonate (catalyst), (iii) method of using a catalytic amount of sodium tetrakis(3,5-trifluoromethylphenyl)borate in water at 30° C., (iv) method of using 1% to 5% by mole of $Er(OTf)_3$ in wet nitromethane at room temperature, and (v) method of using a catalytic amount of cerium (III) triflate in wet nitromethane at room temperature under a substantially neutral pH condition.

<Method (2) of Producing Polymer>

A method of producing the polymer according to the present embodiment (hereinafter, also referred to as a "production method (2)") includes a step (1) of reacting a polymer (P1) which has a repeating unit (II') represented by Formula (II') with a compound (1a) represented by Formula (1a) to obtain a polymer (P2) which has a repeating unit represented by Formula (I') and the repeating unit (II'); a step (2a) of applying at least one treatment selected from the group consisting of hydrolysis, a transesterification reaction, and aminolysis under an alkaline condition and hydrolysis and amide coupling under an alkaline condition to the polymer (P2) to obtain a polymer (P3) which has a repeating unit (I') represented by Formula (I') and a repeating unit (II') represented by Formula (II'); and a step (2b) of hydrolyzing the polymer (P3) under a neutral condition or a weakly acidic condition to obtain a polymer which has a repeating unit (I) represented by Formula (I) and a repeating unit (II) represented by Formula (II).

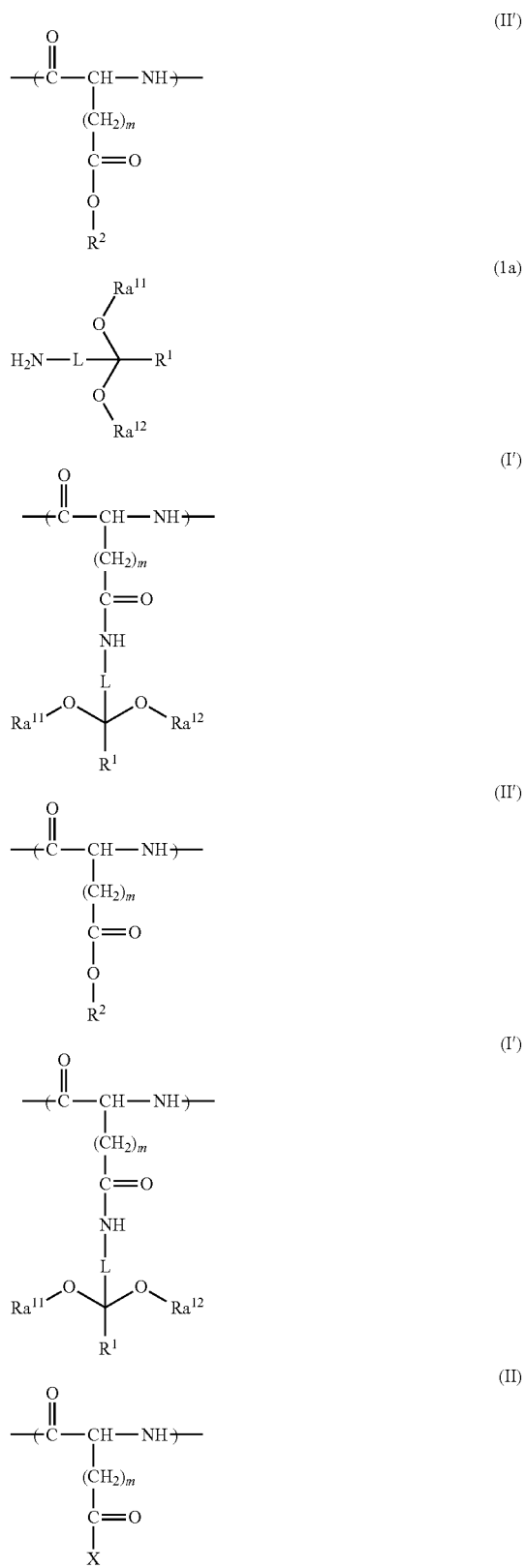

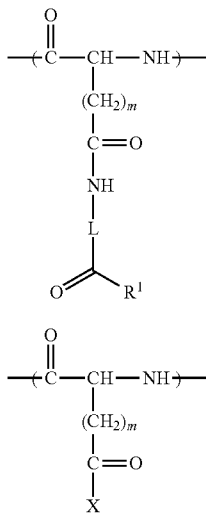

(I)

(II)

[In the formulae, m represents 1 or 2. $R^2$ represents a hydrogen atom, an aliphatic hydrocarbon group, or an aromatic hydrocarbon group. L represents a divalent aromatic hydrocarbon group, or a divalent aliphatic hydrocarbon group. $R^1$ represents a hydrogen atom, an aliphatic hydrocarbon group, or an aromatic hydrocarbon group. $Ra^{11}$ and $Ra^{12}$ each independently represent a methyl group or an ethyl group or $Ra^{11}$ and $Ra^{12}$ are bonded to each other and represent an ethylene group or a propylene group. X represents $OR^x$, $SR^x$, or $NR^{x1}R^{x2}$. $R^x$ represents a hydrogen atom, an aliphatic hydrocarbon group, or an aromatic hydrocarbon group. $R^{x1}$ and $R^{x2}$ each independently represent a hydrogen atom, an aliphatic hydrocarbon group, or an aromatic hydrocarbon group.]

In Formulae (I'), (II'), (I), and (II), m, L, X, $R^x$, $R^{x1}$, and $R^{x2}$ each have the same definition as that for m, L, X, $R^x$, $R^{x1}$, and $R^{x2}$ in Formulae (I) and (II).

In Formulae (1a) and (I'), $R^1$, $Ra^{11}$, and $Ra^{12}$ each have the same definition as described above.

(Step (1))

The step (1) of the production method (2) is the same as the step (1) of the production method (1).

(Step (2a))

In the step (2a) of the production method (2), a desired functional group can be introduced to a side chain of the repeating unit (II') in a state in which the repeating unit (I') is protected by the acetal structure by applying a predetermined treatment to the polymer (P2).

Examples of the hydrolysis under an alkaline condition include a method of performing the treatment in a mixture of a 0.5 N NaOH solution and DMSO (volume ratio: 50/50) at room temperature for 30 minutes, a method of performing the treatment in DMSO using trimethylamine at room temperature for 1 hour, and a method of performing the treatment in DMSO using diisopropylethylamine at room temperature for 1 hour. A carboxylic acid residue obtained by the hydrolysis under the alkaline condition attracts protons in the core of a micelle described below, facilitate hydrolysis of a hydrazone bond, and enables release of a biomaterial under a low pH condition.

The aminolysis can cleave an ester using ethylenediamine or diaminopropane to introduce an amino functional group. By introducing an amino group, the amino group can be bonded to a fluorescent dye. Further, known amino coupling can be applied to the amino group and an image diagnostic agent containing other carboxylic acid groups. Since the acetal structure and the ketal structure are stable under such an amino group-introduced condition, these structures can be provided for polyfunctional nanocarrier design of a polymer.

By performing the hydrolysis under the alkaline condition or the amide coupling, for example, after an ester residue is treated by the hydrolysis under the alkaline condition, the generated carboxylic acid can be subjected to an ester transesterification reaction or amide coupling using a known coupling agent. A suitable structural motif using a hydroxyamine functional group enables the balance between the hydrophilicity and the hydrophobicity of a polymer to be desirable and contributes to self-organization in a polar or non-polar solvent.

(Step (2b))

In the step (2b) of the production method (2), the polymer (P3) is hydrolyzed under a weakly acidic condition, and the acetal structure of the repeating unit (I') of the polymer (P3) is converted to an aldehyde. The conditions for hydrolysis are the same as those in the step (2) of the production method (1).

<Drug Conjugate>

The drug conjugate according to the present embodiment contains the polymer and at least one drug bonded to the polymer.

The drug is not particularly limited and can allow a drug having a desired activity to be bonded to. In the present specification, the drug can also be noted as an "active molecule". Here, the active molecule indicates a molecule having any physiological or chemical activity. The kind of physiological activity or chemical activity of the active molecule is not particularly limited, and the physiological activity of a known compound as an active component of a pharmaceutical product or the chemical or physiological activity of a diagnostic agent used by being administered into the body may be exemplified. Examples of the drug (active molecule) include an anticancer drug, a signal transduction inhibitor, an antimetabolite, an analgesic drug, an anti-inflammatory agent, and a contrast medium, but the present invention is not limited to these. Examples of the anticancer drug include vinca alkaloid such as vinblastine; a COX-2 selective non-steroidal anti-inflammatory agent such as OSU-03012; a BET bromo domain inhibitor such as (+)-JQ1; a staurosporine analogue such as K252A, a demethylating agent such as hydralazine; an alkylating agent such as bendamustine or chlorambucil; a farnesyl transferase inhibitor such as AZD39; and a non-steroidal anti-inflammatory agent such as flurbiprofen. By using a drug conjugate containing the polymer and a drug, alleviation of side effects can be expected even in a case where a drug such as an anticancer drug whose dose is limited due to the side effects is used. Therefore, such a drug is a suitable example of the drug to be bonded to the polymer. Examples of such a drug include a vinca alkaloid-based compound such as vinblastine.

Among these, as the drug, vinca alkaloid such as vinblastine, a staurosporine analogue such as K252A, or a BET bromo domain inhibitor such as (+)-JQ1 is preferable.

In a case where a nitrogen atom-containing group (hereinafter, also referred to as a Schiff base-forming group") capable of forming an aldehyde group and a Schiff base in the drug is present, the polymer and the drug can be bonded to each other by reacting the Schiff base-forming group with an aldehyde group contained in the repeating unit (I) of the polymer. Examples of such a Schiff base include an amino group, an imino group, and a hydrazide group. Further, in a case where the drug does not contain a Schiff base-forming group, the Schiff base-forming group may be introduced to the drug. The introduction of the Schiff base-forming group can be performed according to a known method.

For example, since a Schiff base-forming group is not present in vinblastine, a hydrazide group is introduced to vinblastine to obtain desacetyl vinblastine hydrazide (DAVBNH) so that the drug can be bonded to the polymer. Further, a Schiff base-forming group can be introduced to a staurosporine analogue such as K252A or a BET bromo domain inhibitor (+)-JQ1 according to the same method as described above.

It is preferable that the drug conjugate according to the present embodiment is a polymer having a repeating unit (Ia) represented by Formula (Ia) and having a repeating unit (II) represented by Formula (II).

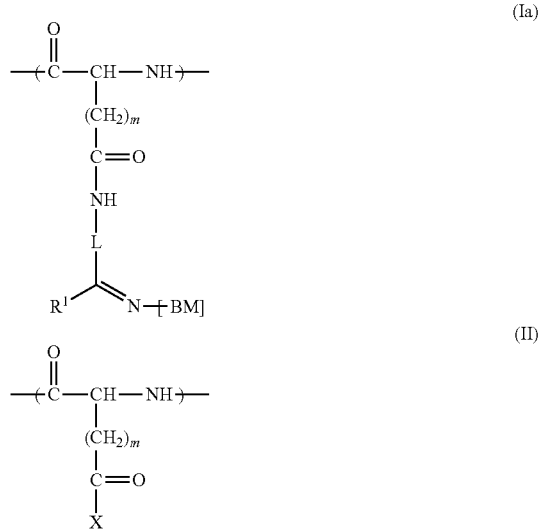

[In the formulae, m represents 1 or 2. L represents a divalent aromatic hydrocarbon group, or a divalent aliphatic hydrocarbon group. $R^1$ represents a hydrogen atom, an aliphatic hydrocarbon group, or an aromatic hydrocarbon group. BM represents an active molecule. X represents $OR^x$, $SR^x$, or $NR^{x1}R^{x2}$. $R^x$ represents a hydrogen atom, an aliphatic hydrocarbon group, or an aromatic hydrocarbon group. $R^{x1}$ and $R^{x2}$ each independently represent a hydrogen atom, an aliphatic hydrocarbon group, or an aromatic hydrocarbon group.]

In Formulae (Ia), and (II), m, L, $R^1$, X, $R^x$, $R^{x1}$, and $R^{x2}$ each have the same definition as that for m, L, $R^1$, X, $R^x$, $R^{x1}$, and $R^{x2}$ in Formulae (I) and (II).

In Formula (Ia), BM represents an active molecule. Examples of the active molecule include the compounds exemplified in the section of the drug.

According to the drug conjugate of the present embodiment, various drugs can be transported into a living body by being carried on a polymer. In the polymer, the amount of the aldehyde group or ketone group to be introduced can be controlled so that the amount of the drugs to be bonded to the aldehyde group or ketone group can be controlled. Therefore, the drug dose can be appropriately controlled.

Further, in the polymer, the aldehyde group or ketone group to be introduced can be selected from an aromatic aldehyde group, an aliphatic aldehyde group, an aromatic ketone group, and an aliphatic ketone group.

Since the Schiff base of an aromatic aldehyde group or an aromatic ketone group is more stable than the Schiff base of an aliphatic aldehyde group or an aliphatic ketone group, the drug is more stably held in a case where an aromatic aldehyde group has been introduced. Therefore, the sustained release of the drug can be controlled by selecting the kind of an aldehyde group or ketone group to be introduced based on the state of the disease or the kind of drug. Further, in the drug conjugate according to the present embodiment, since the drug is stably maintained and the toxicity is alleviated while the drug is held by the polymer, the side effects can be reduced to increase the therapeutic effects.

The drug conjugate can be administered to a living body as it is, but may be formulated by being mixed with other components as appropriate according to a known method. Therefore, the present invention also provides a pharmaceutical composition containing the drug conjugate. In a case where the drug conjugate is formulated, the dosage form is not particularly limited. Examples of the dosage form include an emulsion, an emulsion agent, a liquid drug, a gel-like agent, a capsule, an ointment, a patch, a cataplasm, a granule, a tablet, and a contrast medium. Further, the drug conjugate may be in the form of a micelle. The micelle containing the drug conjugate can be prepared according to a known technique. For example, a micelle containing the drug conjugate can be prepared by dissolving or suspending the drug conjugate in a lipophilic or hydrophilic solvent, adding the dissolved solution or suspension dropwise to a hydrophilic or lipophilic solvent, and stirring the solution.

The pharmaceutical composition containing the drug conjugate may optionally contain other components of the drug conjugate. As other components, components typically used in the pharmaceutical field can be used without particular limitation. For example, the pharmaceutical composition may be obtained by dissolving or suspending the drug conjugate in a pharmaceutically acceptable carrier. As the pharmaceutically acceptable carrier, those typically used in the pharmaceutical field can be used without particular limitation, and examples thereof include water, physiological saline, a phosphate buffer, DMSO, dimethylacetamide, ethanol, glycerol, and mineral oil. In addition, other examples of other components include a solvent, a solubilizing agent, a suspending agent, an isotonizing agent, a buffer agent, a pH regulator, an excipient, a stabilizer, an antioxidant, an osmotic pressure regulator, a preservative, a colorant, and a flavoring agent.

The route of administration of the pharmaceutical composition is not particularly limited, and the pharmaceutical composition can be administered using an oral route or a parenteral route. Further, the parenteral routes include all administration routes other than the oral route, and examples thereof include intravenous administration, intramuscular administration, subcutaneous administration, intranasal administration, intradermal administration, instillation administration, intracerebral administration, intrarectal administration, intravaginal administration, and intraperitoneal administration. The administration may be local administration or systemic administration. The pharmaceutical composition can be administered once or multiple times, and the administration period and the interval can be appropriately selected based on the kind of the drug, the kind and the state of the disease, the administration route, and the age, the weight, and the sexuality of the target to be administered.

The dose of the pharmaceutical composition can be appropriately selected based on the kind of the drug, the kind and the state of the disease, the administration route, and the age, the weight, and the sexuality of the target to be administered. The dose of the pharmaceutical composition can be set as a therapeutically effective amount. For example, the dose thereof can be set to be in a range of 0.01 to 1000 mg per kg body weight for each time.

Particularly in a case where the drug conjugate of the present embodiment is in the form of a micelle, the drug conjugate exhibits pH sensitive drug release characteristics. Particularly, in consideration of the environment in the living body, a drug conjugate to which an aliphatic aldehyde group or aliphatic ketone group has been introduced is excellent in drug release in the environment (pH of 6.6) surrounding acidifying cancer and endosomes (pH of 5) after the drug has been incorporated into the cytoplasm.

Accordingly, in a case where a drug having high toxicity such as vinblastine is used, a drug conjugate whose drug release at a pH of 5 to 6.6 is moderate and to which an aromatic aldehyde group or aromatic ketone group has been introduced is preferable. Meanwhile, in a case where a drug having relatively low toxicity such as K252a or JQ-1 is used, a drug conjugate whose drug release at a pH of 5 to 6.6 is fast and to which an aliphatic aldehyde group or aliphatic ketone group has been introduced is preferable.

Further, particularly in a case where the drug conjugate of the present embodiment is in the form of a micelle, since the drug is stably maintained and the toxicity is alleviated while the drug is held by the polymer, the side effects can be reduced. Therefore, the maximum tolerated dose (MTD) of the micelle of the drug conjugate according to the present embodiment is further increased compared to a case of a drug alone.

[Second Embodiment]
<Compound>

A compound (hereinafter, also referred to as a "compound (K)") according to a second embodiment of the present invention is a compound represented by Formula (k1).

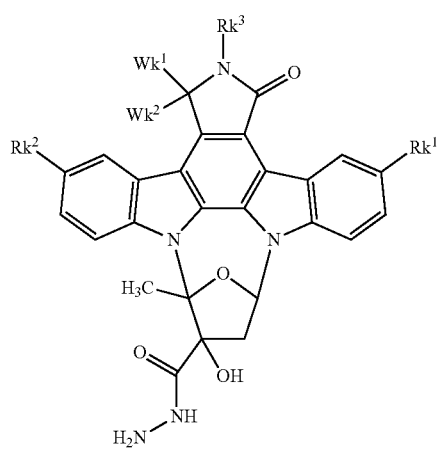

(k1)

[In the formula, $Rk^1$ and $Rk^2$ are residues which may be the same as or different from each other and are each independently selected from the group consisting of (a) hydrogen, halogen, substituted or unsubstituted lower alkyl, substituted or unsubstituted lower alkenyl, substituted or unsubstituted lower alkynyl, hydroxy, lower alkoxy, carboxy, lower alkoxycarbonyl, acyl, nitro, carbamoyl, lower alkylaminocarbonyl, and —$NR^5R^6$ [here, $R^5$ and $R^6$ are each independently selected from hydrogen, substituted or unsubstituted lower alkyl, substituted or unsubstituted lower alkenyl, substituted or unsubstituted lower alkynyl, substituted or unsubstituted aryl, substituted or unsubstituted heteroaryl, substituted or unsubstituted aralkyl, substituted or unsubstituted lower alkylaminocarbonyl, substituted or unsubstituted lower arylaminocarbonyl, alkoxycarbonyl, carbamoyl, and acyl or R5 and R6 are bonded to a nitrogen atom derived from a heterocyclic group]; (b) —$CO(CH_2)_jR^4$ [here, j represents 1 or 6, and $R^4$ is selected from the group consisting of (i) hydrogen, halogen, and —$N_3$, (ii) —$NR^5R^6$ (here, $R^5$ and $R^6$ each have the same definition as described above), (iii) —$SR^7$ (here, $R^7$ is selected from the group consisting of hydrogen, substituted or unsubstituted lower alkyl, substituted or unsubstituted lower alkenyl, substituted or unsubstituted lower alkynyl, substituted or unsubstituted aryl, substituted or unsubstituted heteroaryl, substituted or unsubstituted aralkyl, —$(CH_2)_aCO_2R^{10}$ (here, a represents 1 or 2, and $R^{10}$ is selected from the group consisting of hydrogen and substituted or unsubstituted lower alkyl) and —$(CH_2)_aCO_2NR^5R^6$, and (iv) —$OR^8$ and —$OCOR^8$ (here, $R^8$ is selected from hydrogen, substituted or unsubstituted lower alkyl, substituted or unsubstituted lower alkenyl, substituted or unsubstituted lower alkynyl, substituted or unsubstituted aryl, and substituted or unsubstituted heteroaryl)]; (c) —$CH(OH)(CH_2)_jR^4$ (here, j and $R^4$ each have the same definition as described above); (d) —$(CH_2)_d CHR^{11}CO_2R^{12}$ or —$(CH_2)_dCHR^{11}CONR^5R^6$ (here, d represents 0 to 5, R11 represents hydrogen, —$CONR^5R^6$, or —$CO_2R^{13}$, $R^{13}$ represents hydrogen or substituted or unsubstituted lower alkyl, and $R^{12}$ represents hydrogen or substituted or unsubstituted lower alkyl); (e) —$(CH_2)_kR^{14}$ [here, k represents 2 to 6, and $R^{14}$ represents halogen, substituted or unsubstituted aryl, substituted or unsubstituted heteroaryl, —$COOR^{15}$, —$OR^{15}$ (here, $R^{15}$ represents hydrogen, substituted or unsubstituted lower alkyl, substituted or unsubstituted lower alkenyl, substituted or unsubstituted lower alkynyl, substituted or unsubstituted aryl, substituted or unsubstituted heteroaryl, or acyl), —$SR^7$ (here, $R^7$ has the same definition as described above), —$CONR^5R^6$, —$NR^5R^6$ (here, $R^5$ and $R^6$ each have the same definition as described above), or —$N_3$]; (f) —$CH=CH(CH_2)_{m1}R^{16}$ [here, m1 represent 0 to 4, and $R^{16}$ represents hydrogen, substituted or unsubstituted lower alkyl, substituted or unsubstituted lower alkenyl, substituted or unsubstituted lower alkynyl, substituted or unsubstituted aryl, substituted or unsubstituted heteroaryl, —$COOR^{15}$, —$OR^{15}$ (here, $R^{15}$ has the same definition as described above), —$CONR^5R^6$, or —$NR^5R^6$ (here, $R^5$ and $R^6$ each have the same definition as described above); (g) —$CH=C(CO_2R^{12})_2$ (here, $R^{12}$ has the same definition as described above); (h) —$C\equiv C(CH_2)_nR^{16}$ (here, n represents 0 to 4, and $R^{16}$ has the same definition as described above); (i) —$CH_2OR^{22}$ (here, $R^{22}$ represents tri-lower alkylsilyl in which three lower alkyl groups are the same as or different from one another or $R^{22}$ has the same definition as that for $R^8$); and (j) —$CH(SR^{23})_2$ and —$CH_2$—$SR^7$ (here, $R^{23}$ represents lower alkyl, lower alkenyl, or lower alkynyl, and $R^7$ has the same definition as described above), $Rk^3$ represents hydrogen, halogen, acyl, carbamoyl, substituted or unsubstituted lower alkyl, substituted or unsubstituted alkenyl, substituted or unsubstituted lower alkynyl, or amino, and $Wk^1$ and $Wk^2$ each represent hydrogen or hydroxy or both of $Wk^1$ and $Wk^2$ represent oxygen.]

In a case where the term "lower alkyl" is used alone or in combination with another group, the term "lower alkyl" indicates a linear or branched lower alkyl group having 1 to 6 carbon atoms, preferably 1 to 5 carbon atoms, more preferably 1 to 4 carbon atoms, and particularly preferably 1 to 3 carbon atoms or 1 or 2 carbon atoms. Examples of these groups include methyl, ethyl, propyl, isopropyl, butyl, isobutyl, sec-butyl, tert-butyl, pentyl, amyl, isoamyl, neopentyl, 1-ethylpropyl, and hexyl. The lower alkyl moieties in "lower alkoxy", "lower alkoxycarbonyl", "lower alkylaminocarbonyl", "lower hydroxyalkyl", and "tri-lower alkylsilyl" each have the same definition as that for the "lower alkyl" described above.

The "lower alkenyl" group may be linear or branched and is defined as a $C_2$ to $C_6$ alkenyl group which is of a Z type or an E type. Examples of such a group include vinyl, propenyl, 1-butenyl, isobutenyl, 2-butenyl, 1-pentenyl, (Z)-2-pentenyl, (E)-2-pentenyl, (Z)-4-methyl-2-pentenyl, (E)-4-methyl-2-pentenyl, and pentadienyl such as 1,3-pentadienyl or 2,4-pentadienyl. As the $C_2$ to $C_6$ alkenyl group, a $C_2$ to $C_5$ alkenyl group or a $C_2$ to $C_4$ alkenyl group is more preferable, and a $C_2$ or $C_3$ alkenyl group is still more preferable.

The term "lower alkynyl" group indicates a $C_2$ to $C_6$ alkynyl group which may be linear or branched, and examples thereof include ethynyl, propynyl, 1-butynyl, 2-butynyl, 1-pentynyl, 2-pentynyl, 3-methyl-1-pentynyl, 3-pentynyl, 1-hexynyl, 2-hexynyl, and 3-hexynyl. As the $C_2$ to $C_6$ alkynyl group, a $C_2$ to $C_5$ alkynyl group or a $C_2$ to $C_4$ alkynyl group is more preferable, and a $C_2$ or $C_3$ alkynyl group is still more preferable.

The term "aryl" group indicates a $C_6$ to $C_{14}$ aryl group having 6 to 14 cyclic carbon atoms. These groups may be monocyclic, bicyclic, or tricyclic and are fused rings. Preferred examples of the aryl group include phenyl, biphenyl, naphthyl, anthracenyl, and phenanthrenyl. The aryl moieties in an "arylcarbonyl" group and an "arylaminocarbonyl" group each have the same definition as described above.

The term "heteroaryl" group indicates a C3 to C13 heteroaryl group which may having 1 to 3 heteroatoms independently selected from nitrogen, sulfur, and oxygen. These groups may be monocyclic, bicyclic, or tricyclic. Examples of the $C_3$ to $C_{13}$ heteroaryl group of the present invention include a heteroaromatic group and a saturated or partially saturated heterocyclic group. These heterocycles may be a monocyclic, bicyclic, or tricyclic. Preferred examples of a 5- or 6-membered heterocyclic group include thienyl, furyl, pyrrolyl, pyridyl, pyranyl, monopholinyl, pyrazinyl, methylpyrrolyl, and pyridazinyl. The $C_3$ to $C_{13}$ heteroaryl may be a bicyclic heterocyclic group. Preferred examples of the bicyclic heterocyclic group include benzofuryl, benzothienyl, indolyl, imidazolyl, and pyrimidinyl. Most preferred examples of the $C_3$ to $C_{13}$ heteroaryl include furyl and pyridyl.

As the term "lower alkoxy", an alkoxy group having 1 to 6 carbon atoms, preferably 1 to 5 carbon atoms, more preferably 1 to 4 carbon atoms, and particularly preferably 1 to 3 carbon atoms or 1 or 2 carbon atoms is exemplified, and the alkoxy group may be linear or branched. Examples of these groups include methoxy, ethoxy, propoxy, butoxy, isopropoxy, tert-butoxy, pentoxy, and hexoxy.

As the term "acyl", lower alkanoyl having 1 to 6 carbon atoms and preferably 1 to 5 carbon atoms, 1 to 4 carbon atoms, 1 to 3 carbon atoms, or 1 or 2 carbon atoms is exemplified, and the alkanoyl may be linear or branched. Preferred examples of these groups include formyl, acetyl, propionyl, butyryl, isobutyryl, tert-butyryl, pentanoyl, and hexanoyl. The acyl moiety in an "acyloxy" group has the same definition as described above.

Examples of the term "halogen" include fluoro, chloro, bromo, and iodo.

The term "aralkyl" group indicates $C_7$ to $C_{15}$ aralkyl formed by an alkyl group being substituted with aryl. The alkyl group and aryl can be selected from the $C_1$ to $C_6$ alkyl group and the $C_6$ to $C_{14}$ aryl group defined above and the total number of carbon atoms is in a range of 7 to 15. Preferred examples of the $C_7$ to $C_{15}$ aralkyl group include benzyl, phenylethyl, phenylpropyl, phenylisopropyl, phenylbutyl, diphenylmethyl, 1,1-diphenylethyl, and 1,2-diphenylethyl. The aralkyl moiety in an "aralkyloxy" group has the same definition as described above.

A substituted lower alkyl group, a substituted lower alkenyl group, and a substituted lower alkynyl group each have one to three substituents independently selected from lower alkyl, hydroxy, lower alkoxy, carboxyl, lower alkoxycarbonyl, nitro, halogen, amino, mono- or di-lower alkylamino, dioxolane, dioxane, dithiolane, and dithione. The lower alkyl-substituted moiety in the substituted lower alkyl group, the substituted lower alkenyl group, and the substituted lower alkynyl group and the lower alkyl moiety in the lower alkoxy substituent, the lower alkoxycarbonyl substituent, and the mono- or di-lower alkylamino substituent of the substituted lower alkyl group, the substituted lower alkenyl group, and the substituted lower alkynyl group each have the same definition as that for the "lower alkyl" described above.

A substituted aryl group, a substituted heteroaryl group, and a substituted aralkyl group each have one to three substituents independently selected from lower alkyl, hydroxy, lower alkoxy, carboxy, lower alkoxycarbonyl, nitro, amino, mono- or di-lower alkylamino, and halogen.

Examples of the heterocyclic group to be formed by $R^5$ and $R^6$ bonded to a nitrogen atom include pyrrolidinyl, piperidinyl, piperidino, morpholinyl, morpholino, thiomorpholino, N-methylpiperazinyl, indolyl, and isoindolyl.

Examples of the α-amino acid group include glycine, alanine, proline, glutamic acid, and lysine, and the α-amino acid group may be of an L-type, a D-type, or a racemate type.

It is preferable that $Rk^1$ and $Rk^2$ are independently selected from the group consisting of hydrogen, halogen, nitro, $-CH_2OH$, $-(CH_2)_kR^{14}$, $-CH=CH(CH_2)_mR^{16}$, $-C\equiv C(CH_2)_nR^{15}$, $-CO(CH_2)_jR^4$ (here, $R^4$ represents $-SR^7$), $CH_2O$-(substituted or unsubstituted) lower alkyl (here, it is preferable that substituted lower alkyl is methoxymethyl, methoxyethyl, or ethoxymethyl), $-NR^5R^6$. It is more preferable that both of $Rk^1$ and $Rk^2$ represent hydrogen.

In the preferred definition of $Rk^1$ and $Rk^2$, it is preferable that the residue $R^{14}$ is selected from phenyl, pyridyl, imidazolyl, thiazolyl, tetrazolyl, $-COOR^{15}$, $-OR^{15}$ (here, it is preferable that $R^{15}$ is selected from hydrogen, methyl, ethyl, phenyl, and acyl), $SR^7$ (here, it is preferable that $R^7$ substituted or unsubstituted lower alkyl, 2-thiazoline, and pyridyl), and $-NR^5R^6$ (here, it is preferable that $R^5$ and $R^6$ are selected from hydrogen, methyl, ethyl, phenyl, carbamoyl, and lower alkylaminocarbonyl). Further, it is preferable that the residue $R^{16}$ is selected from hydrogen, methyl, ethyl, phenyl, imidazole, thiazole, tetrazole, $-COOR^{15}$, $-OR^{15}$, and $-NR^5R^6$ (here, the residues $R^{15}$, $R^5$, and $R^6$ each have the preferred definition described above). In the preferred definition of $Rk^1$ and $Rk^2$, it is preferable that the residue $R^7$ is selected from the group consisting of substituted or unsubstituted lower alkyl, substituted or unsubstituted phenyl, pyridyl, pyrimidinyl, thiazole, and tetrazole. Further, it is preferable that k represents 2, 3, or 4, j represents 1 or 2, and m1 and n each independently represent 0 or 1.

$Rk^3$ represents hydrogen or acetyl and most preferably hydrogen.

It is preferable that Wk1 and Wk2 each represent hydrogen.

It is preferable that the compound (K) is represented by Formula (K1-1).

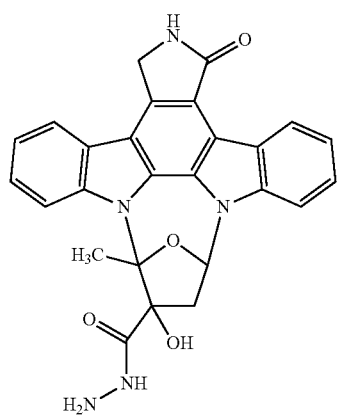

(k1-1)

<Method of Producing Compound (K)>

A compound (I) can be produced by, for example, refluxing a compound represented by Formula (k0) in the presence of anhydrous hydrazine or a hydrazine hydrate and in the absence of a solvent. Further, for example, the compound (K) can be produced by dissolving a compound represented by Formula (k0) in a solvent such as methanol, ethanol, propanol, isopropanol, butanol, tert-butanol, N,N-dimethylformamide (DMF), dimethyl sulfoxide (DMSO), tetrahydrofuran (THF), dioxane, acetonitrile, or toluene, and adding anhydrous hydrazine for a reaction. The reaction temperature and the reaction time are not particularly limited. For example, the reaction can be carried out at room temperature to 50° C. for 30 minutes to 15 hours.

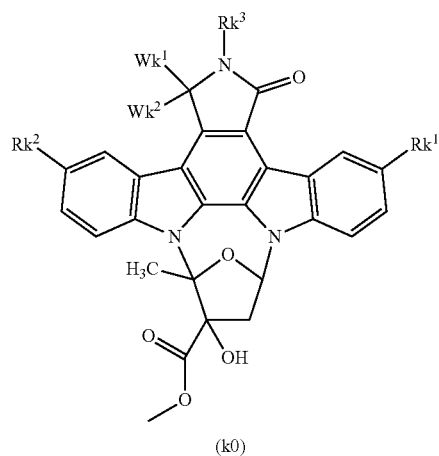

(k0) $\xrightarrow{\text{Anhydrous hydrazine}}$

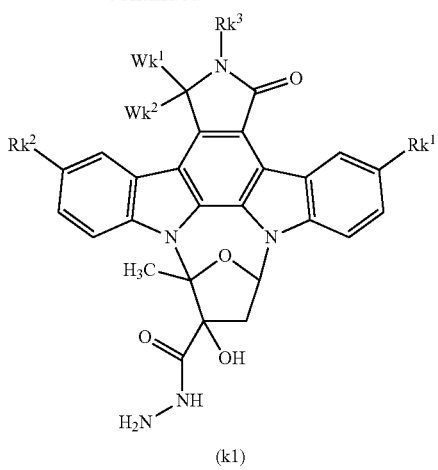

(k1)

<Drug Conjugate>

The second embodiment of the present invention relates to a drug conjugate (hereinafter, also referred to as a "drug conjugate (K)") which contains a polymer having a repeating unit (ka) represented by Formula (ka) and a repeating unit (II) represented by Formula (II).

(ka)

(II)

[In Formula (ka), m, L, and $R^1$ each have the same definition as that for m, L, and $R^1$ in Formula (I). $Rk^1$, $Rk^2$, $Rk^3$, $Wk^1$, and $Wk^2$ each have the same definition as that for $Rk^1$, $Rk^2$, $Rk^3$, $Wk^1$, and $Wk^2$ in Formula (k1). In Formula (II), X and m each have the same definition as that for X and m in Formula (II).]

In Formula (ka), it is preferable that m represents 1.

In Formula (ka), L represents preferably a methylene group, an ethylene group, a propylene group, or a benzylene group and more preferably a methylene group, an ethylene group, or a benzylene group.

In Formula (ka), $R^1$ represents preferably a hydrogen atom or an aliphatic hydrocarbon group and more preferably a hydrogen atom or a methyl group.

In Formula (ka), it is preferable that $Rk^1$ and $Rk^2$ each independently represent hydrogen, halogen, nitro, —$CH_2OH$, —$(CH_2)_kR^{14}$, —$CH=CH(CH_2)_mR^{16}$, —$C\equiv C(CH_2)_nR^{15}$, —$CO(CH_2)_jR^4$ (here, $R^4$ represents —$SR^7$), $CH_2O$-(substituted or unsubstituted) lower alkyl (here, it is preferable that substituted lower alkyl is methoxymethyl, methoxyethyl, or ethoxymethyl), —$NR^5R^6$ and more preferable that $Rk^1$ and $Rk^2$ represent hydrogen.

In formula (ka), $Rk^3$ represents preferably hydrogen or acetyl and more preferably hydrogen.

In Formula (ka), it is preferable that $Wk^1$ and $Wk^2$ represent hydrogen.

In Formula (II), it is preferable that m represents 1.

In Formula (II), X represents preferably $OR^x$ and more preferably OH (hydroxy group).

It is preferable that the drug conjugate (K) contains a polymer having a repeating unit (ka-1) represented by Formula (ka-1) and a repeating unit (II) represented by Formula (II).

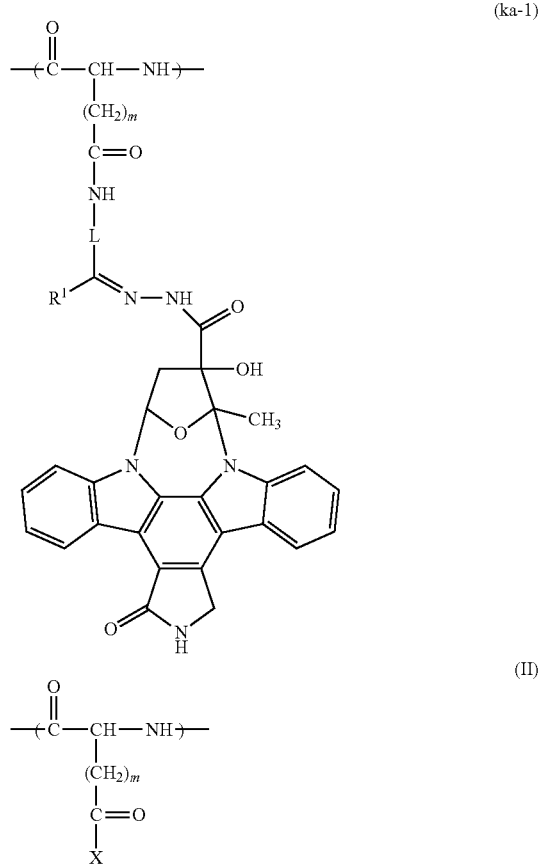

[In Formula (ka-1), m, L, and $R^1$ each have the same definition as that for m, L, and $R^1$ in Formula (I). In Formula (II), X and m each have the same definition as that for X and m in Formula (II).]

In Formula (ka-1), it is preferable that m represents 1.

In Formula (ka-1), L represents preferably a methylene group, an ethylene group, a propylene group, or a benzylene group and more preferably a methylene group, an ethylene group, or a benzylene group.

In Formula (ka-1), $R^1$ represents preferably a hydrogen atom or an aliphatic hydrocarbon group and more preferably a hydrogen atom or a methyl group.

In Formula (II), X represents preferably $OR^x$ and more preferably OH (hydroxy group).

The compound (K) or the drug conjugate (K) exhibits effectiveness on malignant cancer or metastatic cancer in which cancer treatment drugs of the related art do not exhibit effectiveness. Therefore, the compound (K) and the drug conjugate (K) are useful as treatment drugs for cancer having resistance to the cancer treatment drugs of the related art.

Similar to the drug conjugate according to the first embodiment, the sustained release of the compound (K) can be controlled by obtaining the drug conjugate (K) from the compound (K). Further, since the compound (K) is stably maintained and the toxicity is alleviated while the compound (K) is held by the polymer, the side effects can be reduced to increase the therapeutic effects.

Further, similar to the micelle according to the first embodiment, the release of the compound (K) from the drug conjugate (K) can be controlled depending on the pH environment in a living body by preparing a micelle containing the drug conjugate (K). A micelle containing the drug conjugate (K) can be prepared according to a known method similar to the micelle of the drug conjugate according to the first embodiment. For example, a micelle containing the drug conjugate (K) can be prepared by dissolving or suspending the drug conjugate (K) in a lipophilic or hydrophilic solvent, adding the dissolved solution or suspension dropwise to a hydrophilic or lipophilic solvent, and stirring the solution.

In addition, the drug conjugate (K) corresponds to the embodiment in which the drug is the compound (K) in the drug conjugate according to the first embodiment and is included in the drug conjugate according to the first embodiment. Further, the drug conjugate may correspond to the embodiment in which BM represents the compound (K) in Formula (Ia) according to the first embodiment.

<Pharmaceutical Composition>

The compound (K) or the drug conjugate (K) can be administered to a living body as it is, but may be formulated by being mixed with other components as appropriate according to a known method. Therefore, the present invention also provides a pharmaceutical composition containing the compound (K) or the drug conjugate (K). In a case where the compound (K) or the drug conjugate (K) is formulated, the dosage form is not particularly limited. Examples of the dosage form include an emulsion, an emulsion agent, a liquid drug, a gel-like agent, a capsule, an ointment, a patch, a cataplasm, a granule, a tablet, and a contrast medium. Further, the drug conjugate may be in the form of a micelle.

The pharmaceutical composition containing the compound (K) or the drug conjugate (K) may optionally contain other components of the compound (K) or the drug conjugate (K). As other components, components typically used in the pharmaceutical field can be used without particular limitation. For example, the pharmaceutical composition may be obtained by dissolving or suspending the compound (K) or the drug conjugate (K) in a pharmaceutically acceptable carrier. As the pharmaceutically acceptable carrier, those typically used in the pharmaceutical field can be used without particular limitation, and examples thereof include water, physiological saline, a phosphoric acid buffer, DMSO, dimethylacetamide, ethanol, glycerol, and mineral oil. In addition, other examples of other components include a solvent, a solubilizing agent, a suspending agent, an isotonizing agent, a buffer agent, a pH regulator, an excipient, a stabilizer, an antioxidant, an osmotic pressure regulator, a preservative, a colorant, and a flavoring agent.

The route of administration of the pharmaceutical composition is not particularly limited, and the pharmaceutical composition can be administered using an oral route or a parenteral route. Further, the parenteral routes include all administration routes other than the oral route, and examples thereof include intravenous administration, intramuscular administration, subcutaneous administration, intranasal administration, intradermal administration, instillation administration, intracerebral administration, intrarectal administration, intravaginal administration, and intraperitoneal administration. The administration may be local administration or systemic administration.

The pharmaceutical composition can be administered once or multiple times, and the administration period and the interval can be appropriately selected based on the kind of the drug, the kind and the state of the disease, the administration route, and the age, the weight, and the sexuality of the target to be administered.

The dose of the pharmaceutical composition can be appropriately selected based on the kind of the drug, the kind and the state of the disease, the administration route, and the age, the weight, and the sexuality of the target to be administered. The dose of the pharmaceutical composition can be set as a therapeutically effective amount. For example, the dose thereof can be set to be in a range of 0.01 to 1000 mg per kg body weight for each time.

The pharmaceutical composition can be applied to a disease, to which K252a or an analogue thereof can be applied, without particularly limitation. The pharmaceutical composition can be suitably used as a pharmaceutical composition particularly for treating or preventing a tumor. The tumor to which the pharmaceutical composition can be applied is not particularly limited, and suitable examples thereof include lung cancer, pancreatic cancer, head and neck cancer, and mesothelioma.

Further, the compound (K), the drug conjugate (K), or the micelle of the drug conjugate (K) exhibits excellent cytotoxic activity against tumor cells having a gatekeeper mutation of EGFR (d746-750/T790M, d746-750/T790M/C797S, L858R, T790M, or the like) and tumor cells having a mutation in c-Kit, FLT3, or RET. Therefore, the pharmaceutical composition can be particularly suitably used as a pharmaceutical composition for treating or preventing the tumors having such mutations. For example, the pharmaceutical composition can be suitably used as a pharmaceutical composition for treating or preventing tumors having mutations shown in FIG. 42. Since cancers having these mutations are resistant to tumor treating drugs of the related art in many cases, the pharmaceutical composition is extremely useful. Accordingly, the present invention also provides the pharmaceutical composition for treating or preventing tumors which are resistant to the tumor treating drugs of the related art. The tumor treating drugs of the related art are not particularly limited, and examples thereof include Gefitinib, Afatinib, Osimertinib, Midosutaurin, Erlotinib, AG1478, Gemcitabine, Cisplatin, and Pemetrexed. As a suitable mode for the pharmaceutical composition to be used, a combination of tumor treating drugs of the related art may be exemplified. Therefore, the present invention also provides a pharmaceutical composition for treating or preventing a tumor which contains the compound (K) or the drug conjugate (K) and at least one other tumor treating drug.

Further, according to another embodiment, the present invention provides 1) use of the compound (K), the drug conjugate (K), or the micelle thereof in the production of the pharmaceutical composition for treating or preventing tumors; 2) method of treating or preventing tumors, including administering the compound (K), the drug conjugate (K), or the micelle thereof to a target (for example, a patient having a tumor with mutations shown in FIG. 42); 3) the compound (K), the drug conjugate (K), or the micelle thereof used for treating or preventing tumors; and 4) use of the compound (K), the drug conjugate (K), or the micelle thereof for treating or preventing tumors.

EXAMPLES

The present invention will be described in detail based on the following examples. However, the embodiments of the present invention is not limited to the description of these examples.

Synthesis Example 1

Synthesis of methoxy-poly(ethylene glycol)-b-poly(β-benzyl-aspartamide)

A methoxy-poly(ethylene glycol)-b-poly(β-benzyl-aspartamide) (MeO-PEG-PBLA; PEG molecular weight=12 kDa; degree of polymerization=PBLA=40) copolymer was synthesized by carrying out ring-opening polymerization of β-benzylaspartic acid N-carboxaldehyde which was initiated by the terminal primary amino group of α-methoxy-ω-amino poly(ethylene glycol). The ω-amine group was blocked by acetylation.

Synthesis Example 2

Synthesis of Aromatic Acetal Group-Introduced Polymer

A PEG-PBLA polymer (220 mg, 0.011 mmol) was dissolved in DMF (2 mL), {[4-(dimethoxymethyl)phenyl]methanamine} (100 μL, 0.58 mmol) was added to the solution, the temperature thereof was gradually increased, and the resulting solution was stirred at 40° C. for 4 days. For the purpose of character analysis, some of the reaction mixture was ether-precipitated, and the aromatic acetal group-introduced polymer was recovered.

Figure 2:
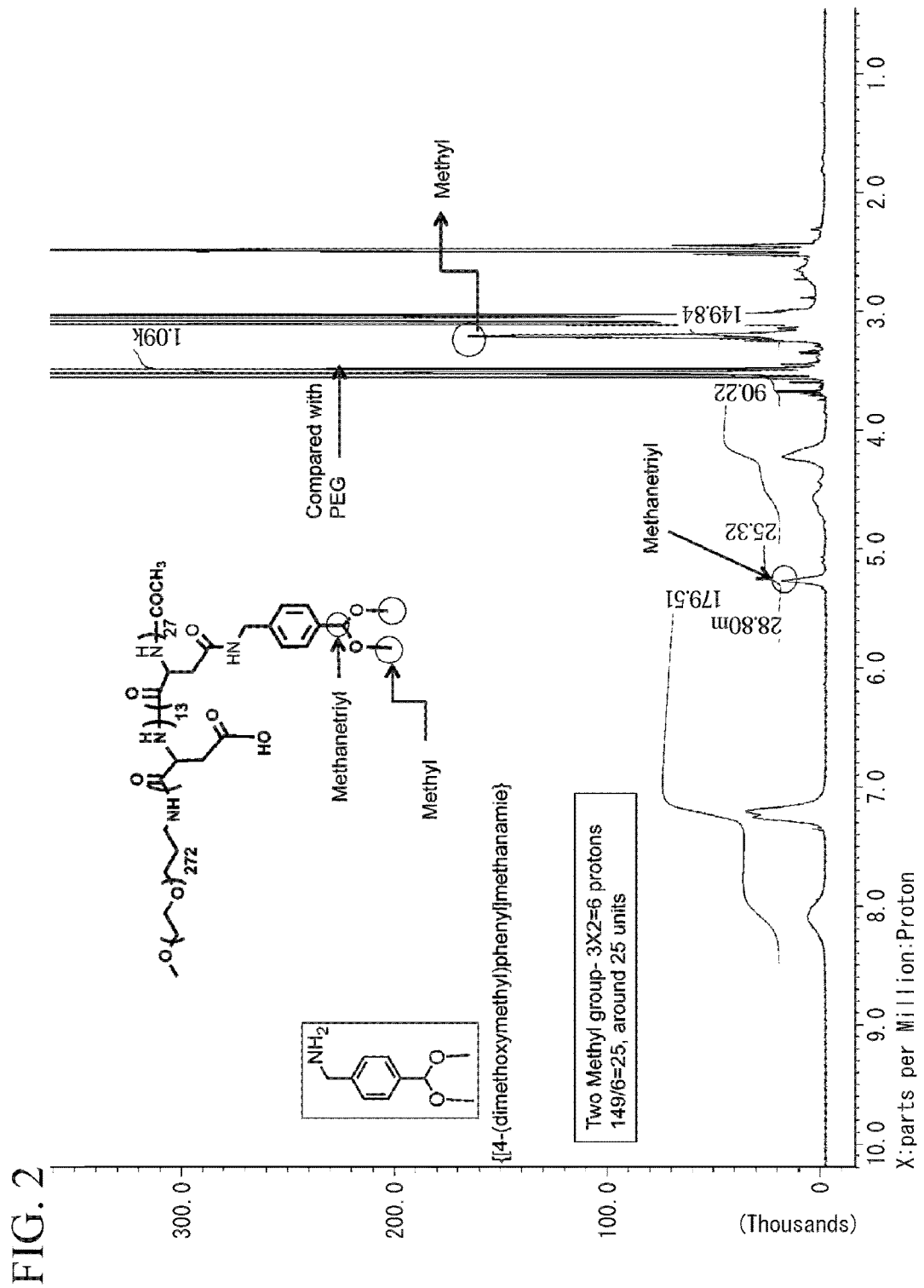
FIG. 2 shows a $^1$H-NMR spectrum of an acetal group-containing polymer serving as an intermediate of an aromatic aldehyde group-containing polymer according to an embodiment of the present invention.

The reaction scheme is shown in FIG. 1. Further, $^1$H-NMR analysis results of the obtained aromatic acetal group-introduced polymer are shown in FIG. 2.

Based on the $^1$H-NMR analysis, substitution of 25 benzyl ester units with amides was confirmed. The remaining benzyl esters (40−25=15) were hydrolyzed presumably during the ether precipitation operation.

Synthesis Example 3

Synthesis of Aromatic Aldehyde Group-Containing Polymer

Figure 3:
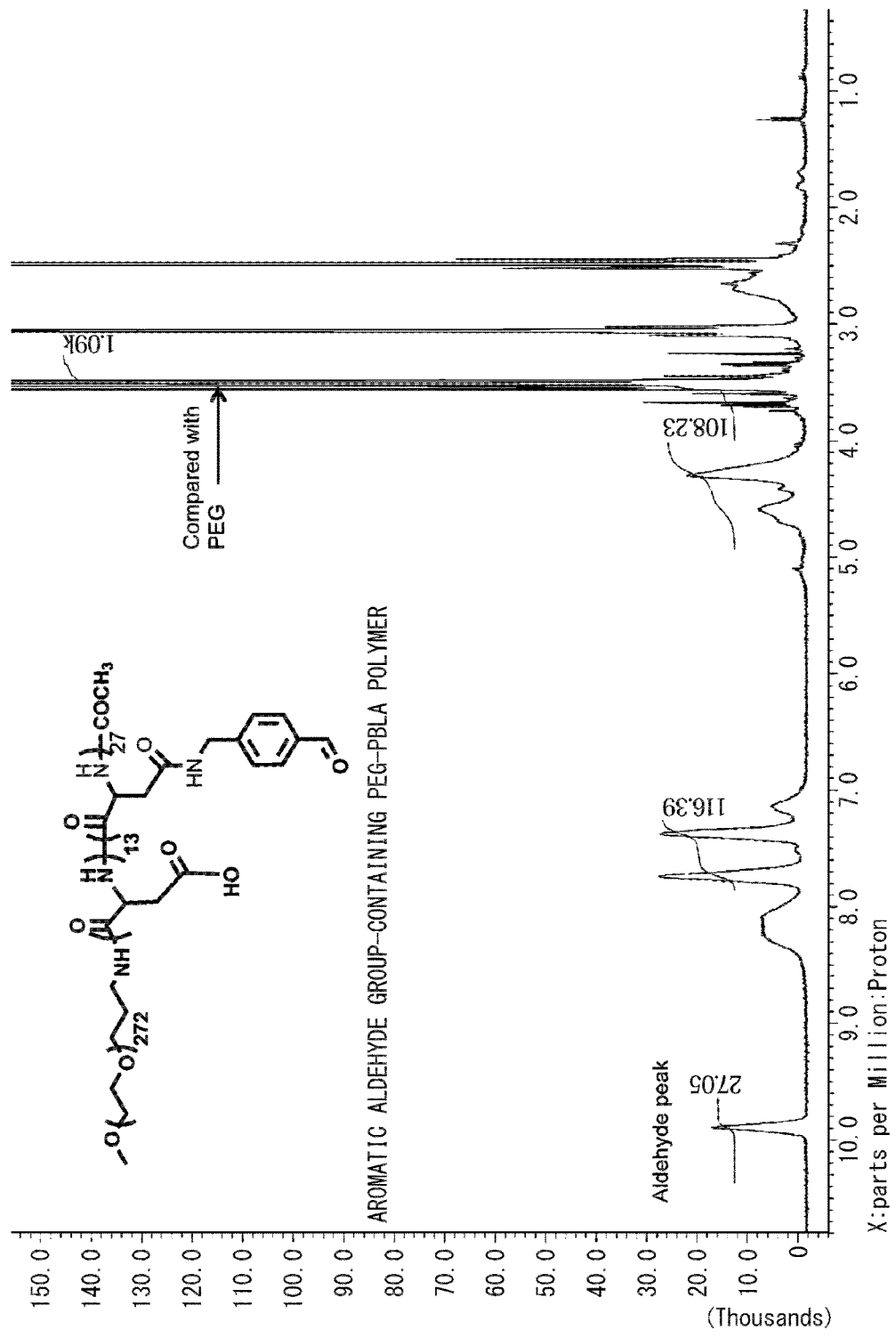
FIG. 3 shows a $^1$H-NMR spectrum of an aromatic aldehyde group-containing polymer according to an embodiment of the present invention.

After the aminolysis reaction, the reaction mixture was acidified (0.1 N HCl, 100 μL, 30 minutes) and dialyzed with water, and the polymer was freeze-dried so that the aldehyde group-introduced polymer was recovered from a dialysis bag. The reaction scheme is shown in FIG. 1. Further, ¹H-NMR analysis results of the obtained aromatic aldehyde group-containing polymer are shown in FIG. 3. Based on ¹H-NMR spectrum, 27 aldehyde units were confirmed.

Synthesis Example 4

Synthesis of Aliphatic Aldehyde Group-Containing Polymer

Figure 4:
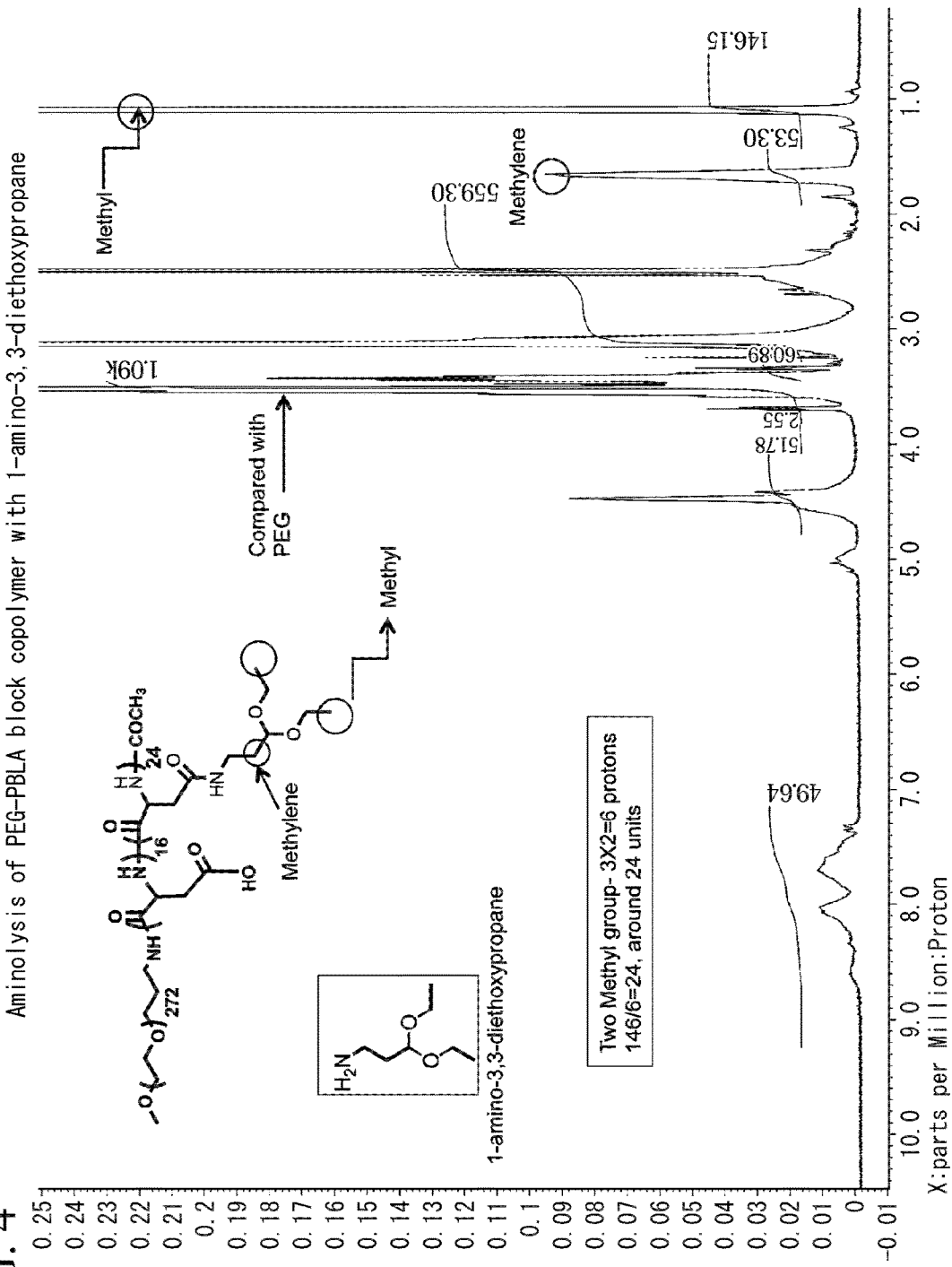
FIG. 4 shows a $^1$H-NMR spectrum of an acetal group-containing polymer serving as an intermediate of an aliphatic aldehyde group-containing polymer according to an embodiment of the present invention.
Figure 5:
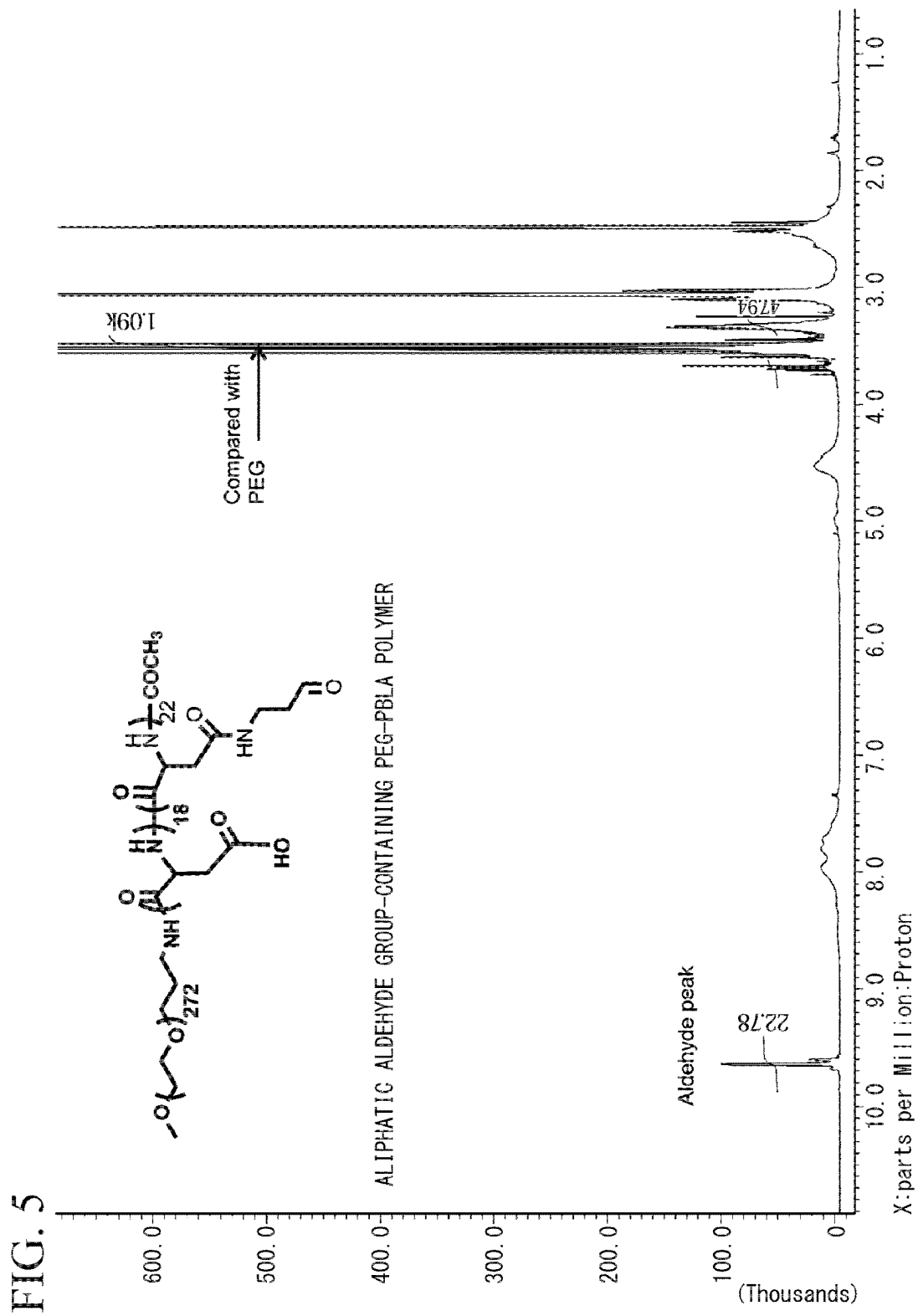
FIG. 5 shows a $^1$H-NMR spectrum of an aliphatic aldehyde group-containing polymer according to an embodiment of the present invention.

An aliphatic aldehyde group-containing polymer was synthesized using the same method as the method used for the synthesis of the aromatic aldehyde group-containing polymer except that 1-amino-3,3-diethoxypropane was used in place of the {[4-(dimethoxymethyl)phenyl]methanamine}. The reaction scheme is shown in FIG. 1. Further, ¹H-NMR analysis results of the aliphatic acetal group-containing polymer serving as an intermediate are shown in FIG. 4. Further, ¹H-NMR analysis results of the obtained aromatic aldehyde group-containing polymer are shown in FIG. 5. Based on ¹H-NMR spectrum, 23 aldehyde units were confirmed.

Example 1

Preparation (1) of Drug Conjugate

<Synthesis of DAVBNH>

Vinblastine sulfate was purchased from BOC Science (US). The vinblastine sulfate was converted to vinblastine by performning an alkali treatment. The vinblastine sulfate (200 mg) was dissolved in water (3 mL), and a sodium hydroxide solution (5 N) was added dropwise thereto.

In this manner, a white suspension was obtained. Free vinblastine was extracted from this suspension using dichloromethane (DCM). The DCM phase was dried over anhydrous sodium sulfate and evaporated to obtain approximately 150 mg of free vinblastine.

Figure 6A:
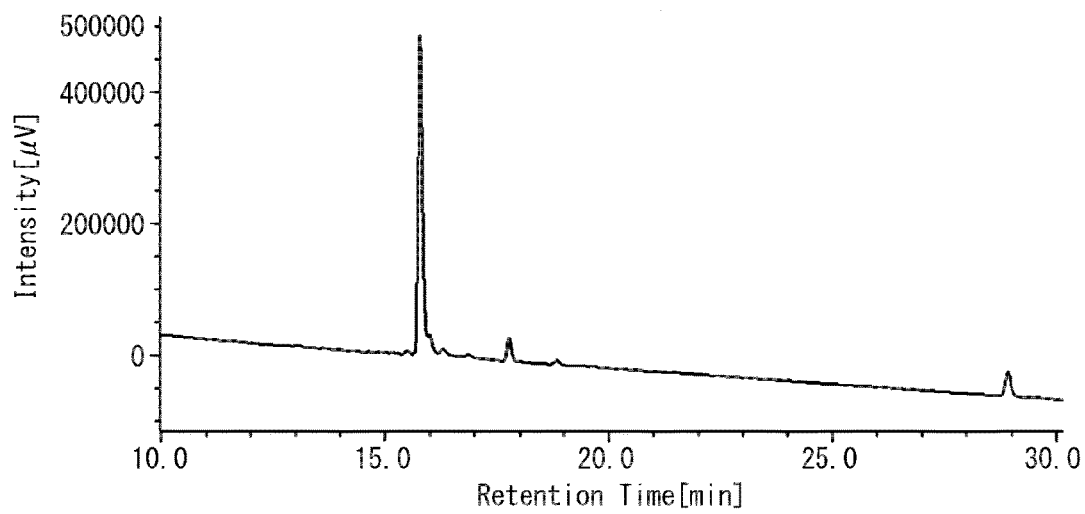
FIG. 6A shows HPLC analysis results for synthesized desacetyl vinblastine hydrazide (DAVBNH).
Figure 6B:
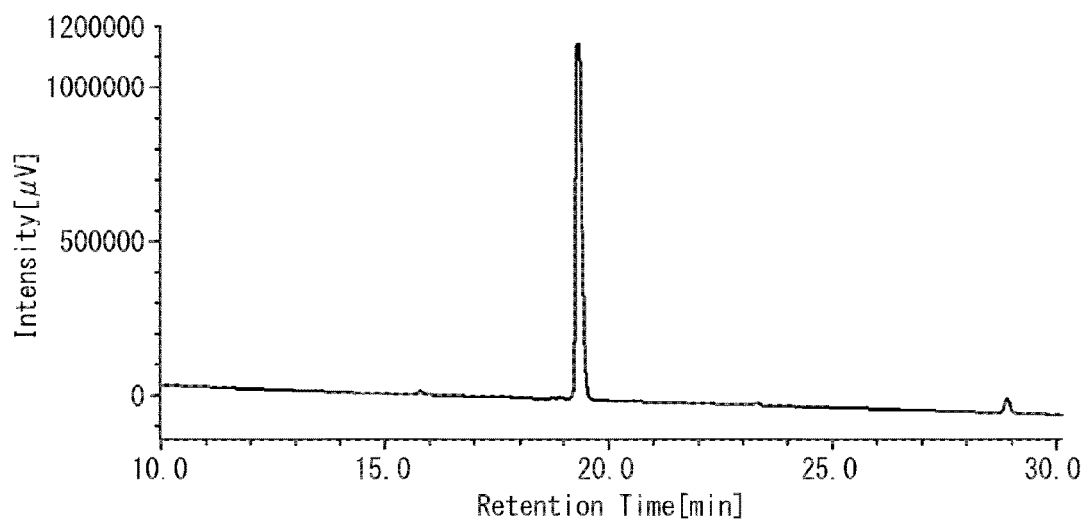
FIG. 6B shows HPLC analysis results for vinblastine.

The vinblastine (150 mg) was dissolved in anhydrous methanol (1 mL), and the solution was added to anhydrous hydrazine (1 mL). The reaction mixture was stirred at 55° C. for 22 hours. The reaction mixture was evaporated to obtain a dried product. In the evaporation, toluene was used as a co-evaporation solvent. The obtained product was used for preparation of a drug conjugate and a micelle without carrying out further purification. The product was analyzed by HPLC. The analysis results are shown in FIGS. 6A and 6B. The conditions for HPLC analysis are as follows.

GE's Inert Sustain C18 column 4.6×250 nm
Solvent A: 0.1% trifluoroacetic acid, pH: 2.0
Solvent B: acetonitrile
Gradient of 5% B to 80B %
Flow rate: 1 mL/min, 30 minutes
UV detection: wavelength of 220 nm Further, the synthesis scheme for DAVBNH from vinblastine is shown below.

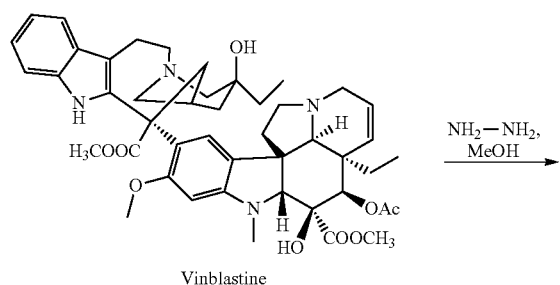

Vinblastine

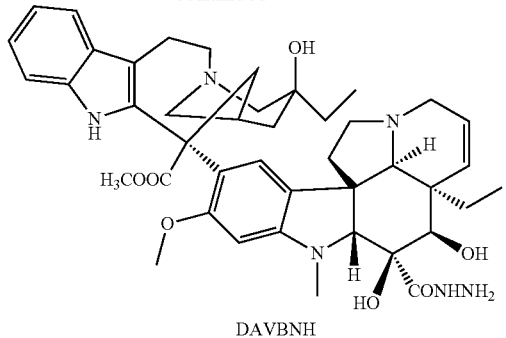

DAVBNH

<Preparation of Drug Conjugate>

Figure 7:
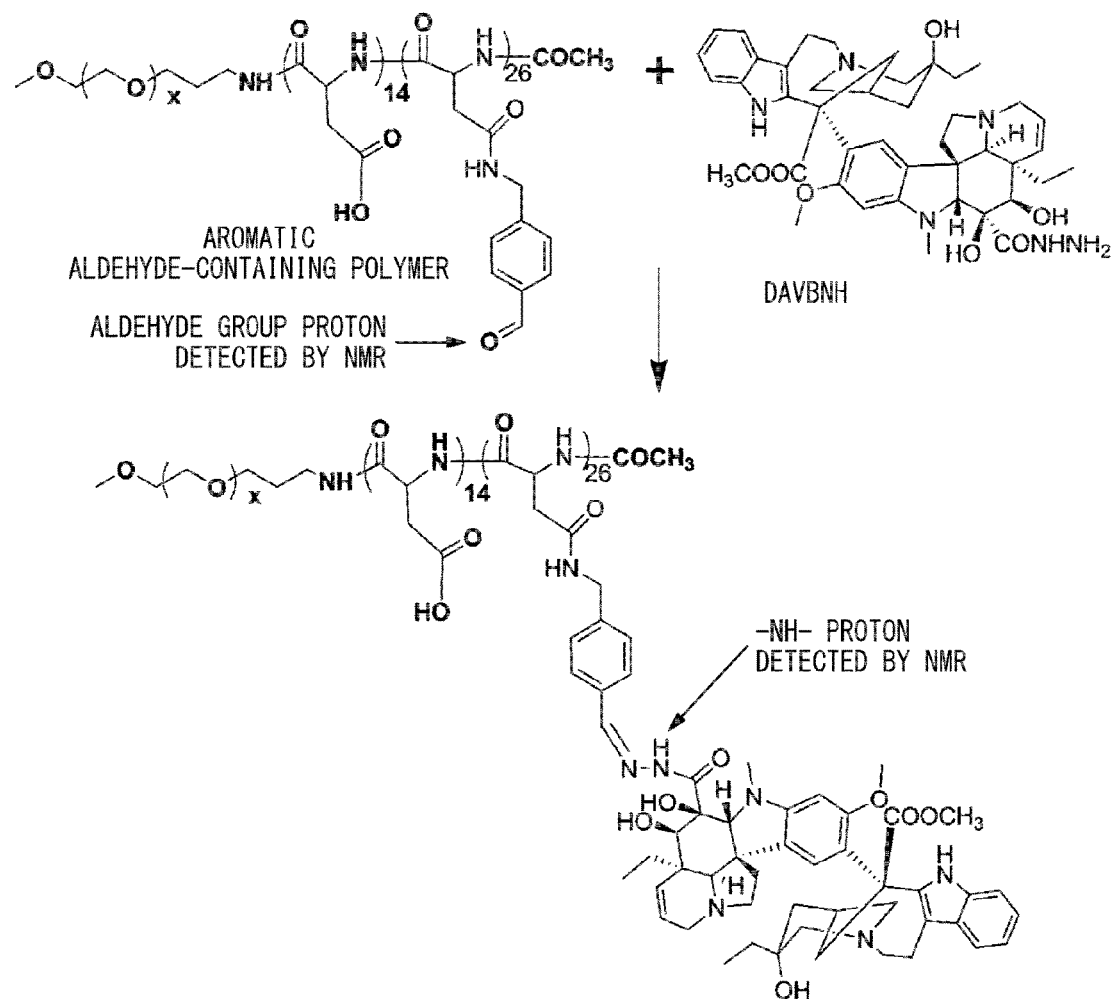
FIG. 7 is a scheme diagram showing a reaction caused by bonding desacetyl vinblastine hydrazide (DAVLBH) to a polymer according to an embodiment of the present invention.

The reaction between the product (DAVLBH) and the aromatic aldehyde group-containing polymer, obtained in the above-described manner, was carried out in a DMSO solution in a temperature range of 35° C. to 40° C. for 72 hours, and the solvent was exchanged for dimethylacetamide (DMAc) by dialysis (dialysis for 4 hours, the dialysis solvent was exchanged once). A transparent DMAc solution was generated due to this solvent exchange. Further, the reaction scheme for bonding the aromatic aldehyde group-introduced polymer and DAVBNH to each other is shown in FIG. 7.

<Preparation of DAVBNH Bonded Polymer Micelle>

The DMAc solution obtained in the above-described manner was used for preparation of a micelle. The DMAc solution of the drug conjugate was added dropwise to water such that the volume ratio of the solution to water was set to 1 to 10 and vortexed to prepare a micelle. This solution was dialyzed with water in a dialysis bag having a molecular cutoff (MWCO) of 3500 Da for 24 hours. The dialysis solvent was exchanged five times during the dialysis. The solution in the dialysis bag was filtered with a filter (0.22 μm) and concentrated by ultrafiltration using a 100 kDa MWCO filter membrane.

Figure 8A:
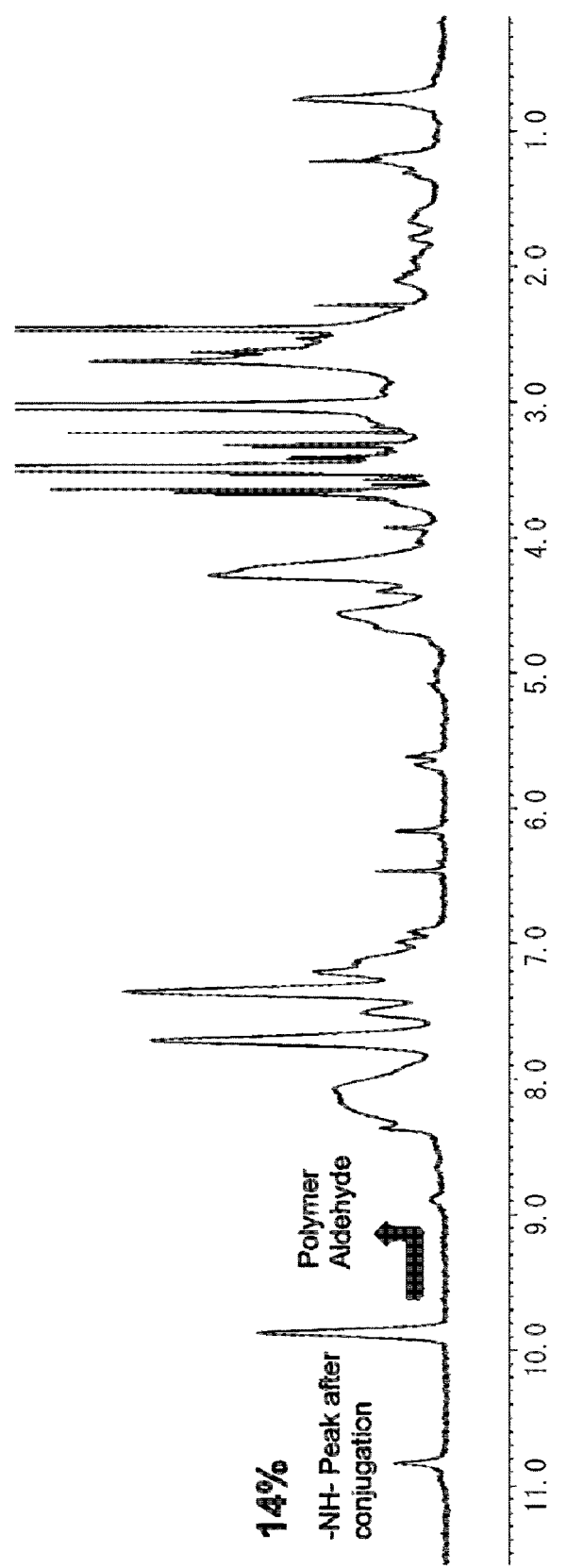
FIG. 8A shows a $^1$H-NMR spectrum of a drug conjugate (DAVBNH load amount of 14%) obtained by bonding DAVBNH to a polymer according to an embodiment of the present invention.
Figure 8B:
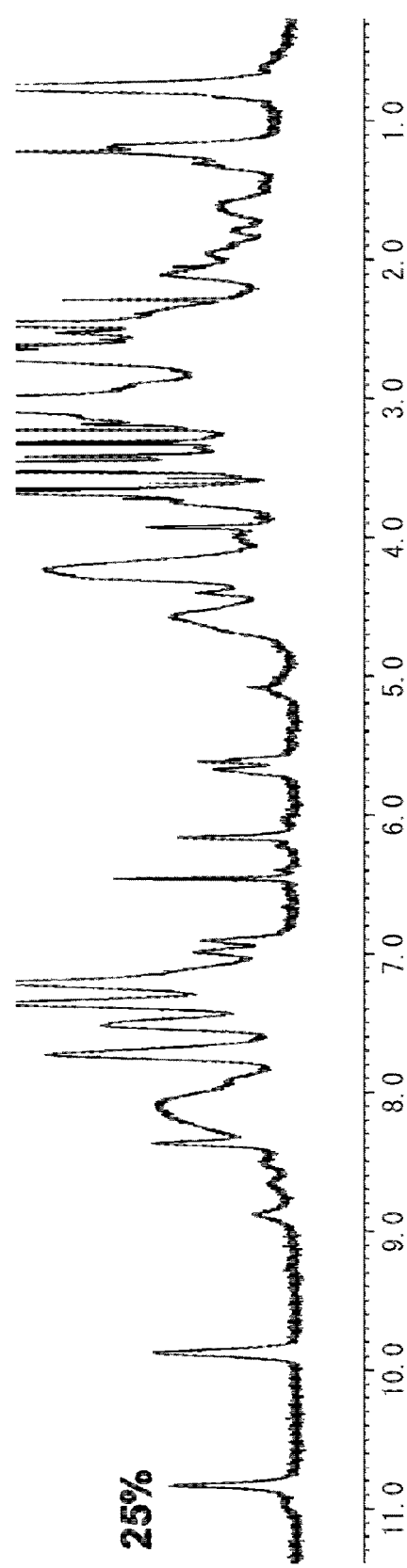
FIG. 8B shows a $^1$H-NMR spectrum of a drug conjugate (DAVBNH load amount of 25%) obtained by bonding DAVBNH to a polymer according to an embodiment of the present invention.
Figure 8C:
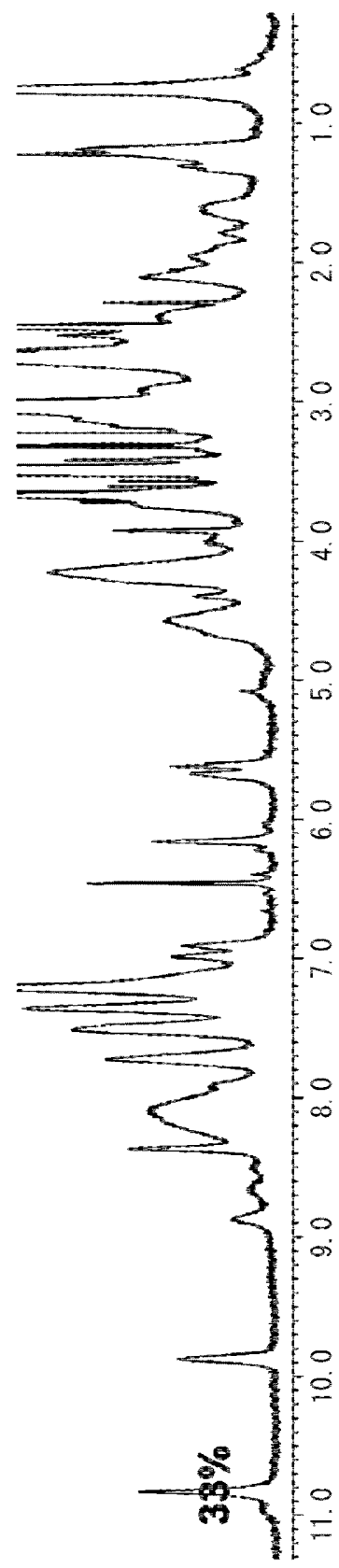
FIG. 8C shows a $^1$H-NMR spectrum of a drug conjugate (DAVBNH load amount of 33%) obtained by bonding DAVBNH to a polymer according to an embodiment of the present invention.

Three kinds of micelles having different DAVBNH load amounts (14%, 25%, and 33%) were prepared according to the above-described method. Further, the mass ratio of DAVLBH, which had been added to the polymer, to the polymer in the drug bonding reaction was set as the load amount of DAVBNH. The results of the drug bonding reaction and the difference in drug load amount were confirmed by ¹H NMR analysis. The micelle aqueous solution was freeze-dried and re-dissolved in d₆ DMSO for NMR analysis. The results of ¹H NMR analysis are shown in FIGS. 8A, 8B, and 8C. FIGS. 8A, 8B, and 8C each show the analysis results of micelles having DAVBNH load amounts of 14%, 25%, and 33%.

Based on the ¹H NMR analysis, it was confirmed that the amount of DAVBNH bonded to the polymer was able to be controlled by changing the DAVBNH load amount of during the drug bonding reaction.

Figure 9A:
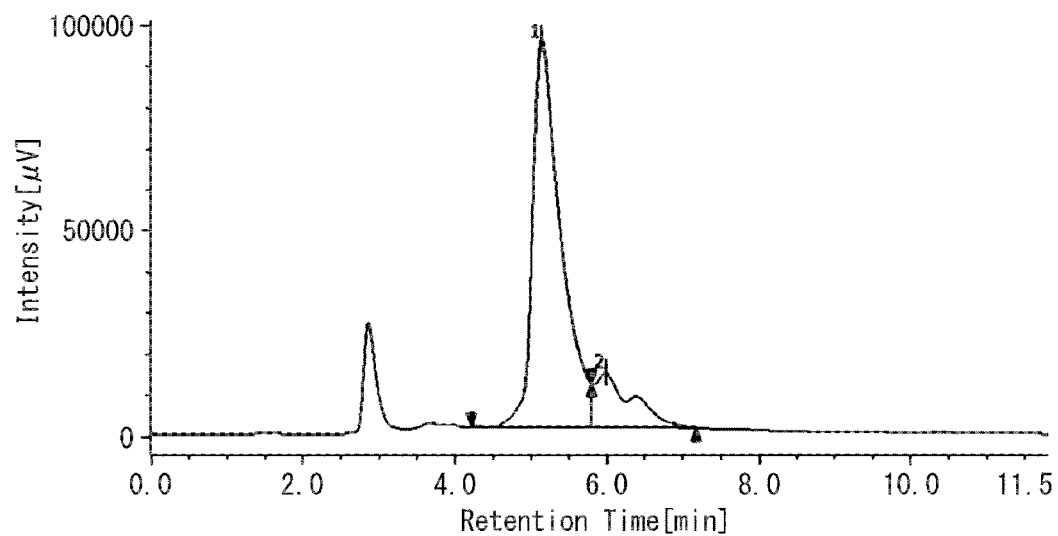
FIG. 9A shows HPLC analysis results for an 82.5 µg/mL DAVBNH standard solution.
Figure 9B:
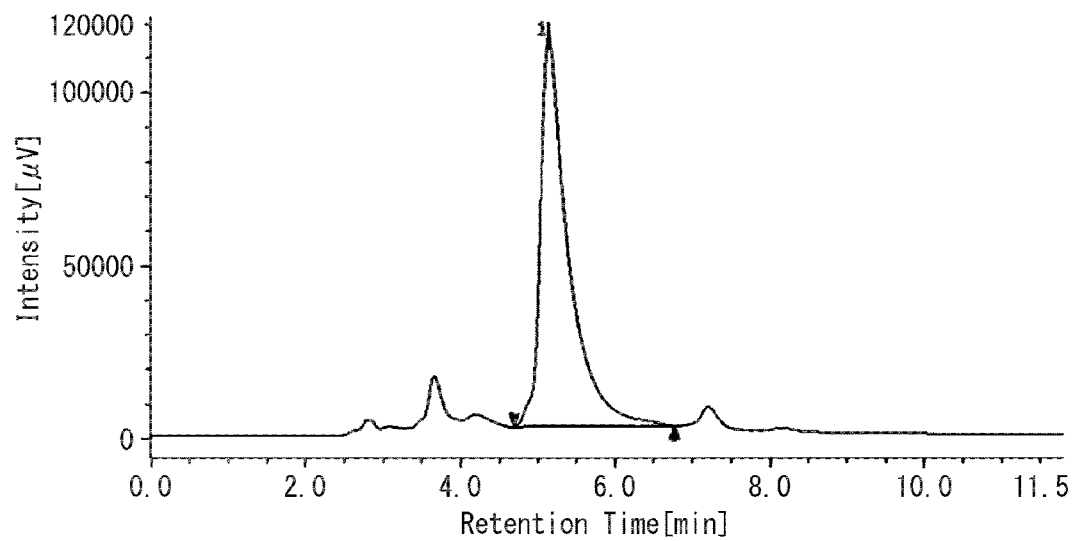
FIG. 9B shows HPLC analysis results for DAVBNH released from a drug conjugate according to an embodiment of the present invention after the drug conjugate is acid-treated under a condition of performing dilution 20 times.

Next, the concentration of DAVBNH in the micelle was measured by HPLC. The micelle solution was incubated in a 0.1 N HCl solution for 2 hours, and the released drug was measured by HPLC using a UV detector having a wavelength of 220 nm. The free DAVBNH solution was used as a standard solution. The analysis results for HPLC are shown in FIGS. 9A and 9B. The conditions for HPLC analysis are as follows.

TOSOH's TSKgel ODS-80Tm column 4.6×150 mm

Figure 10A:
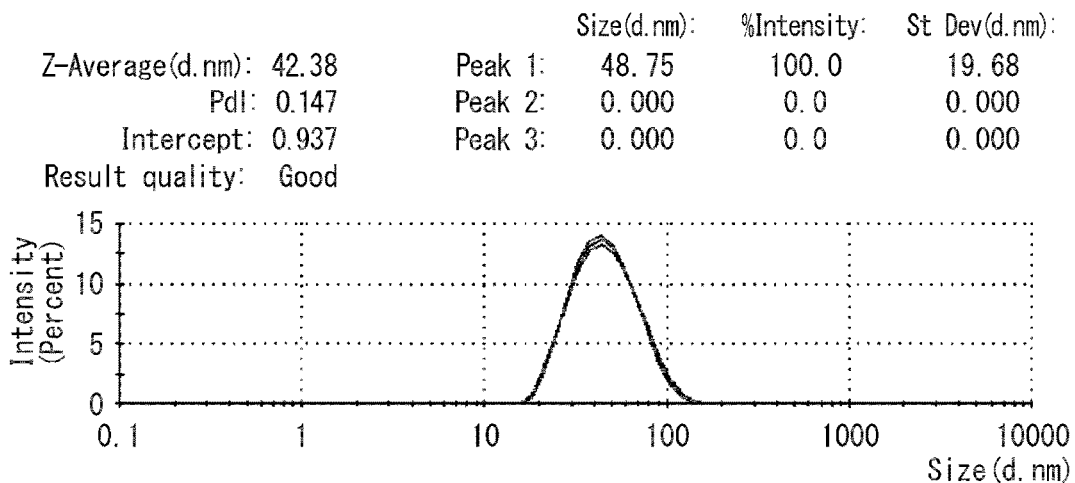
FIG. 10A shows analysis results for the polydispersion index (PDI) and the micelle size of a drug conjugate (DAVBNH load amount of 14%) according to an embodiment of the present invention.
Figure 10B:
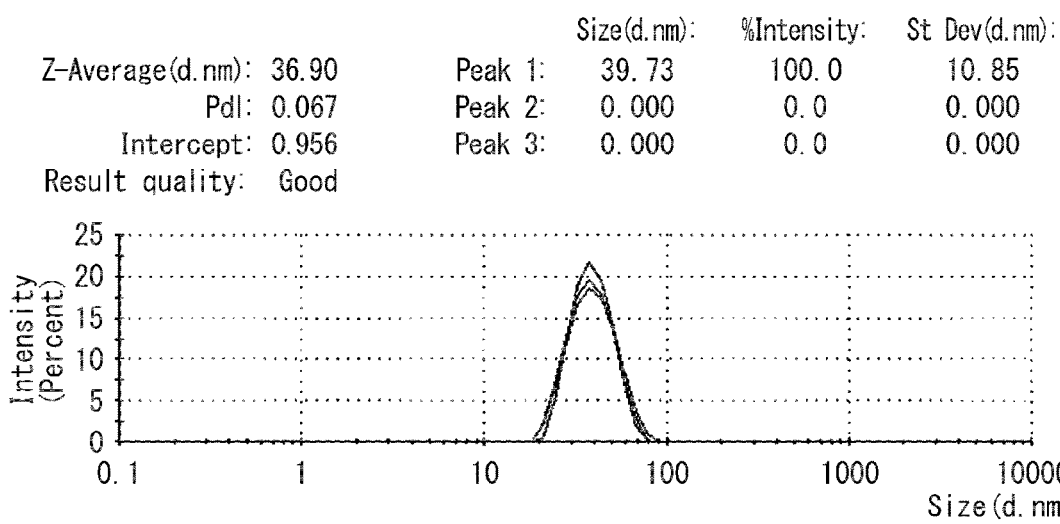
FIG. 10B shows analysis results for the polydispersion index (PDI) and the micelle size of a drug conjugate (DAVBNH load amount of 25%) according to an embodiment of the present invention.
Figure 10C:
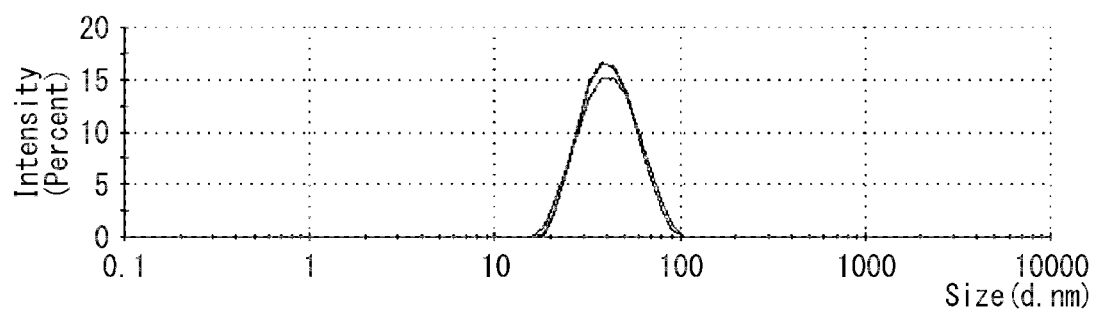
FIG. 10C shows analysis results for the polydispersion index (PDI) and the micelle size of a drug conjugate (DAVBNH load amount of 33%) according to an embodiment of the present invention.

Uniform concentration between 20 mM phosphoric acid buffer (pH of 2.5) and methanol (1:1)
Flow rate: 0.6 mL/min
UV detection: wavelength of 220 nm
<Measurement of Micelle Size and PDI>
The micelle size and the polydispersion index (PDI) were acquired using a dynamic light scattering (DLS) technique.
The measurement was performed using a green laser (532 nm) as an incident beam and Zetasizer nano ZS (Malvern instruments, UK) at a detection angle of 173° under a temperature condition of 25° C. The results are shown in Table 1 and FIG. 10. Further, each indicator in FIG. 10 is listed in Table 2. In Table 1, the value of % drug conjugation was calculated by the following equation.

% Drug conjugation=mass of DAVBNH/(mass of DAVBNH+mass of polymer)×100

TABLE 1

| % Drug conjugation | Drug unit (amount added (mg)) *1 | Drug unit ($^1$H NMR) *2 |
|---|---|---|
| 14 | 4 | 5 |
| 25 | 8 | 11 |
| 33 | 12 | 15 |

*1: amount added (mg) of DAVBNH (molecular weight of 769 g/mol) to be added to 12 mg of polymer (molecular weight of 18300 g/mol)
*2: ratio of —NH-proton (see FIG. 7) peak to proton peak of PEG detected by $^1$H NMR

TABLE 2

| | |
|---|---|
| Z-Average (d. nm) | The cumulant of strength based on the measurement of the particle size (diameter) in the nanometer (nm) unit |
| PdI | The polydispersion index (PDI) of particle size distribution in a sample solution |
| Intercept | The value of the intersection of the correlation curve on the y axis. This value is used for evaluation of the signal/noise ratio of a measurement sample and quality evaluation of data. The ideal value is 1. The value is desirably greater than 0.6 and most preferably greater than 0.9. |
| Result quality | The quality evaluation based on the results using Zetasizer software |
| Peak 1~3 | Three peaks in the polydispersion samples measured by Zetasizer software. All samples used in the present test are monodisperse samples, and only one particle distribution type expressed as Peak 1 was measured (the values of Peak 2 and Peak 3 are 0). |

Example 2

Cytotoxicity Test (1) of Drug Conjugate Against Brain Tumor Cells

The in vitro cytotoxicity of the vinblastine sulfate and the drug conjugate (DAVBNH bonded polymer micelle of Example 1) was evaluated using cell-counting kit-8 with respect to U87MG serving as a glioma cell strain. The U87MG cells (3000 cells/well) were cultured in a DMEM medium containing 10% FBS using a 96-well plate. Thereafter, the U87MG cells were exposed to the vinblastine sulfate or the drug conjugate whose dose was different from that of the vinblastine sulfate. The cell survival rates after 48 hours and 72 hours from the exposure were acquired by measuring the formazan absorbance 450 nm at 450 nm.

Figure 11:
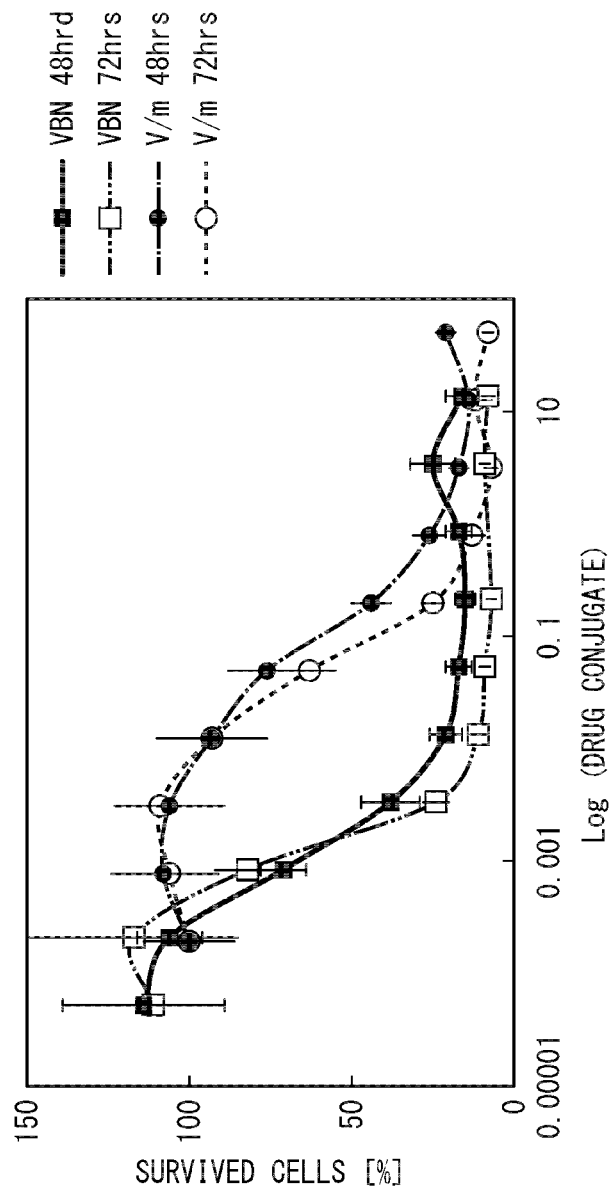
FIG. 11 shows results obtained by performing a cytotoxicity test of a drug conjugate according to an embodiment of the present invention against brain tumor cells.

The results of the cytotoxicity test are shown in FIG. 11. In FIG. 11, "VBN" indicates vinblastine sulfate, and "V/m" indicates a DAVBNH bonded polymer micelle. In the DAVBNH bonded polymer micelle, the value of IC50 was greater than that of the vinblastine sulfate, but the dose dependence characteristic of the cytotoxic activity was the same as that of the vinblastine sulfate.

This result indicates that the activity of DAVBNH is maintained in the micelle.

Example 3

Blood Kinetic Test of Drug Conjugate
<Preparation of Alexa-647 Labeled DAVBNH Bonded Polymer Micelle>
An aromatic aldehyde group-containing polymer (20 mg), DAVBNH (10 mg), and Alexa-647 hydrazide (0.5 mg) were dissolved in DMSO (1 mL), and the solution was stirred at 35° C. for 72 hours. The solvent was exchanged for DMAc to prepare a micelle as described in <Preparation of DAVBNH bonded polymer micelle> of Example 1.
<Blood Kinetic Test>
The blood kinetic test was performed using an in vivo laser scanning microscope. A Nikon A1R confocal laser scanning microscope system equipped with a Plan Apo VC 20× DIC N2 Nikon lens (numerical aperture: 0.75) installed in an upright ECLIPSE FN1 (manufactured by Nikon Corporation, Tokyo, Japan) was used. A laser having a wavelength of 640 nm was used to excite Alexa-647. The Alexa-647 labeled DAVBNH bonded polymer micelle (dose of vinblastine: approximately 30 mg/kg) was administered to a mouse (BALB/c Nude, female, 6 weeks old) using a tail vein catheter. The Alexa 647 labeled DAVBNH bonded polymer micelle was observed based on the blood flow in the earlobe area blood vessel of the mouse, and the blood kinetics were monitored for 20 hours from the administration. The obtained data was treated using Nikon NIS Elements (ver. 4.00.06).

Figure 12:
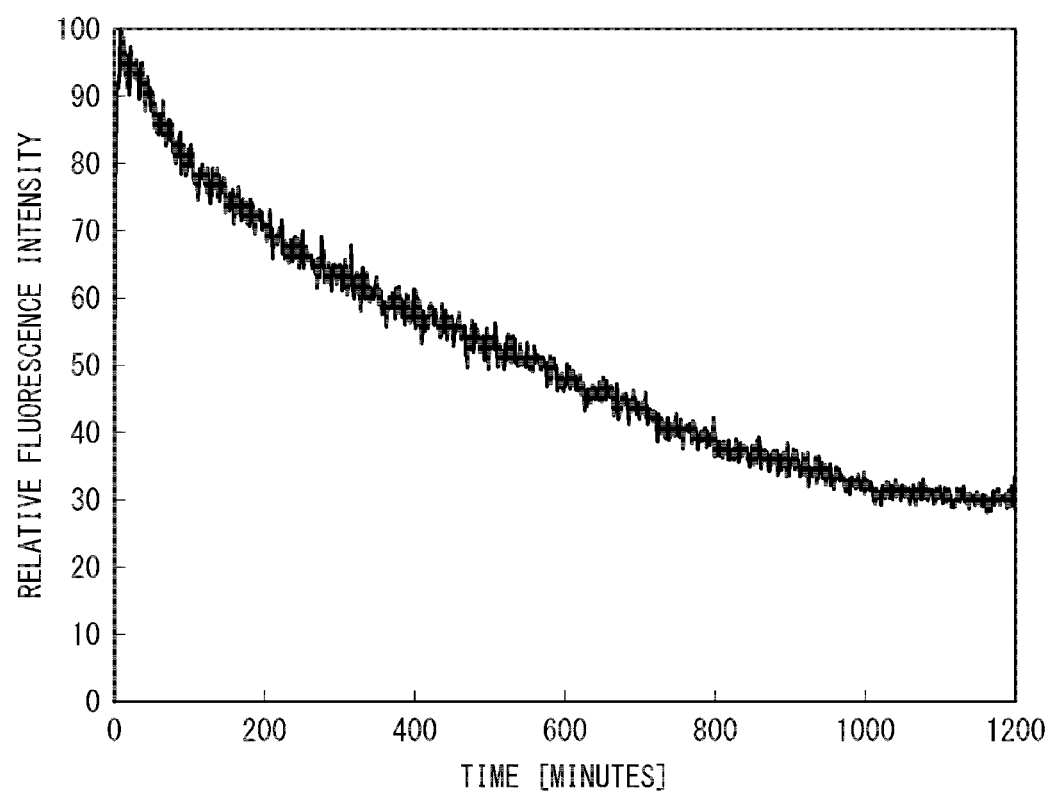
FIG. 12 shows results obtained by performing a blood kinetic test on a drug conjugate according to an embodiment of the present invention. The blood concentration is acquired by the fluorescence intensity of Alexa-647 used for labeling of the drug conjugate and expressed as the relative fluorescence intensity obtained by setting the fluorescence intensity at the time of administration to 100.

The results of the blood kinetic test are shown in FIG. 12. It was confirmed that the Alexa-647 labeled DAVBNH bonded polymer micelle was circulated in the blood for at least 20 hours.

Example 4

In Vivo Antitumor Test (IC50)-(1) of Drug Conjugate

5×10$^6$ U87MG cells in the DMEM medium were inoculated subcutaneously in mice (BALB/c Nude, female, 6 weeks old). After 5 days from the inoculation, a drug treatment was started. Intravenous injection of the drug was carried out four times every four days. The administration groups were prepared as follows, and the number of mice in each group was set to 5.
Administration group 1: PBS administration (PBS)
Administration group 2: 2 mg/kg of vinblastine sulfate (VBN)
Administration group 3: 2 mg/kg of DAVBNH (DAVBNH)
Administration group 4: 2 mg/kg of DAVBNH bonded polymer micelle (Example 1) (V/m 2)
Administration group 5: 4 mg/kg of DAVBNH bonded polymer micelle (Example 1) (V/m 4)
Administration group 6: 8 mg/kg of DAVBNH bonded polymer micelle (Example 1) (V/m 8)
Administration group 7: 16 mg/kg of DAVBNH bonded polymer micelle (Example 1) (V/m 16)

Figure 13A:
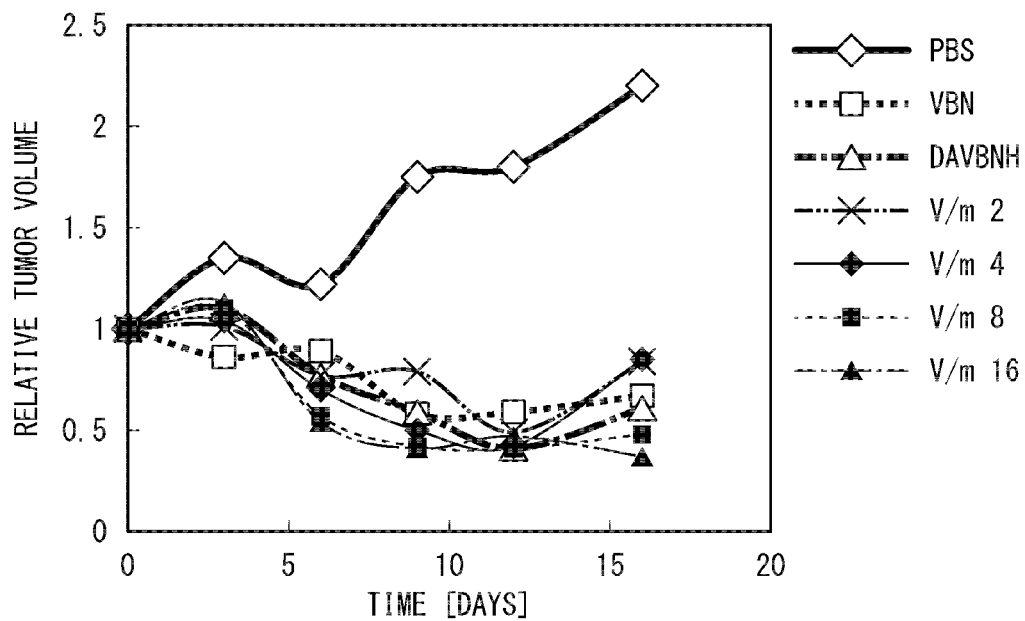
FIG. 13A is a graph (graph showing changes in tumor sizes with time) showing the results obtained by performing an in vivo antitumor test on a drug conjugate according to an embodiment of the present invention. The graph is shown using relative values obtained by setting the value at the time of administration to 1.
Figure 13B:
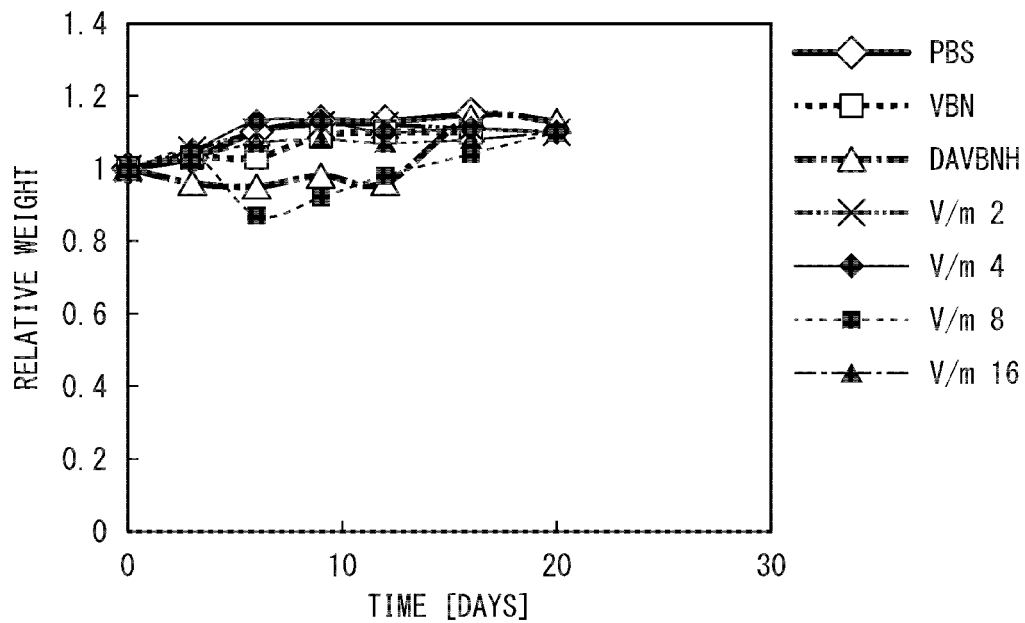
FIG. 13B is a graph (graph showing changes in weights with time) showing the results obtained by performing an in vivo antitumor test on a drug conjugate according to an embodiment of the present invention. The graph is shown using relative values obtained by setting the value at the time of administration to 1.

The results of the in vivo antitumor test are shown in FIG. 12. Further, the abbreviation of each administration group shown in FIGS. 13A and 13B is described in the parentheses of each administration group. FIG. 13A shows changes in antitumor sizes with time and FIG. 13B shows changes in weights of mice with time. The DAVBNH bonded polymer micelle administration group exhibits the same antitumor effects as those of the vinblastine sulfate administration group and the DAVBNH administration group. Further, in the DAVBNH bonded polymer micelle administration group, significant weight loss was not observed at any dose. Vinblastine has strong toxicity and the maximum tolerated dose thereof for a mouse is 2 mg/kg. In the present test, significant toxicity was not confirmed even in a case where 16 mg/kg of the DAVBNH bonded polymer micelle was administered. This result indicates that the toxicity of vinblastine can be alleviated while maintaining the antitumor activity by employing the DAVBNH bonded polymer micelle.

Synthesis Example 5

Synthesis of Aliphatic Ketone Group-Containing Polymer

A PEG-PBLA polymer (318 mg, 0.016 nmol) was dissolved in DMF (3 mL), and 3,3-dimethoxybutane (200 μL) was added to the obtained solution. The reaction solution was stirred at 40° C. for 72 hours, an HCl solution (100 μL, 0.1 N) was added to thereto, and the resulting solution was stirred for 1 hour. A polymer formed by introduction of an aliphatic ketone to a side chain was recovered by dialyzing the solution with water and freeze-drying the polymer.

Figure 14:
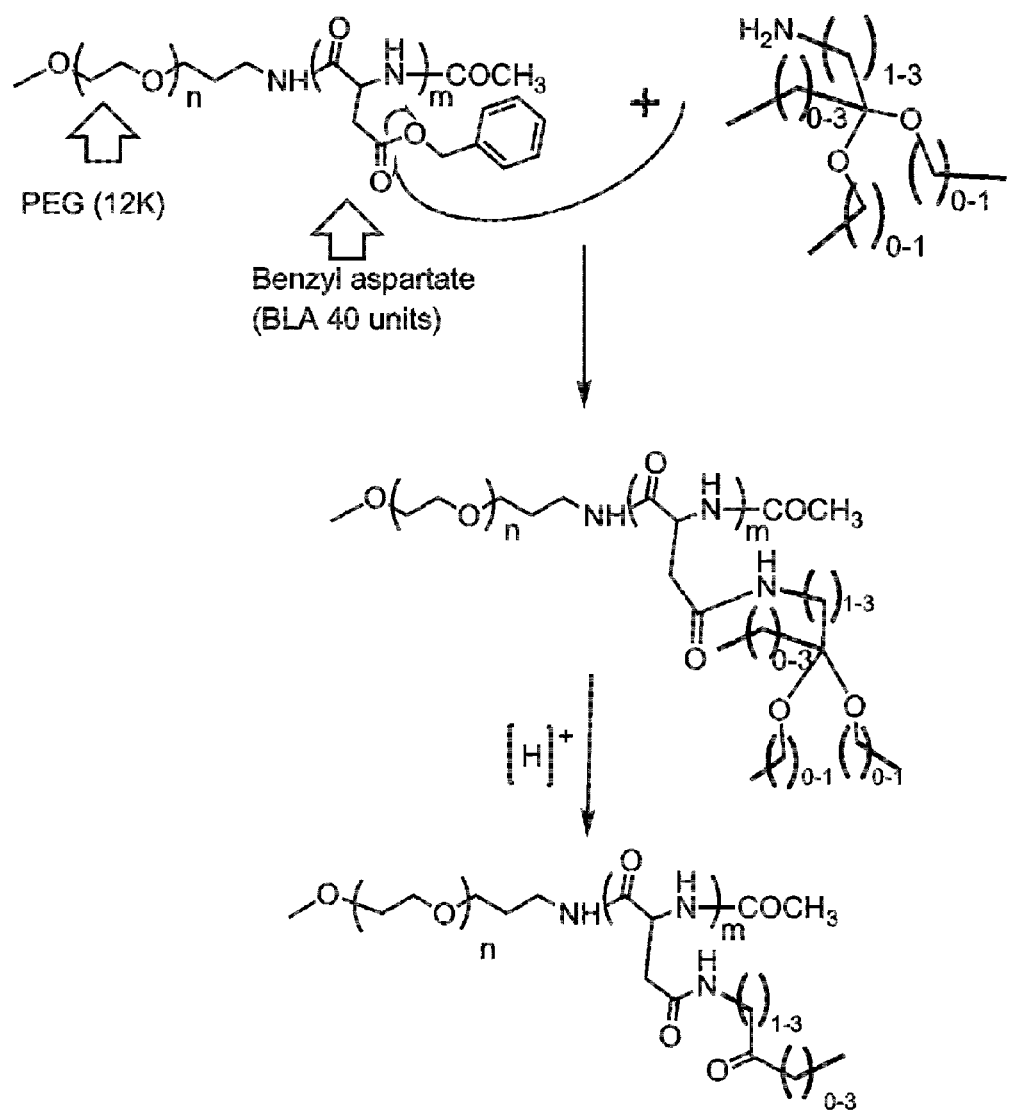
FIG. 14 shows a scheme for synthesizing an aromatic ketone group-containing polymer and an aliphatic ketone group-containing polymer according to an embodiment of the present invention.
Figure 15:
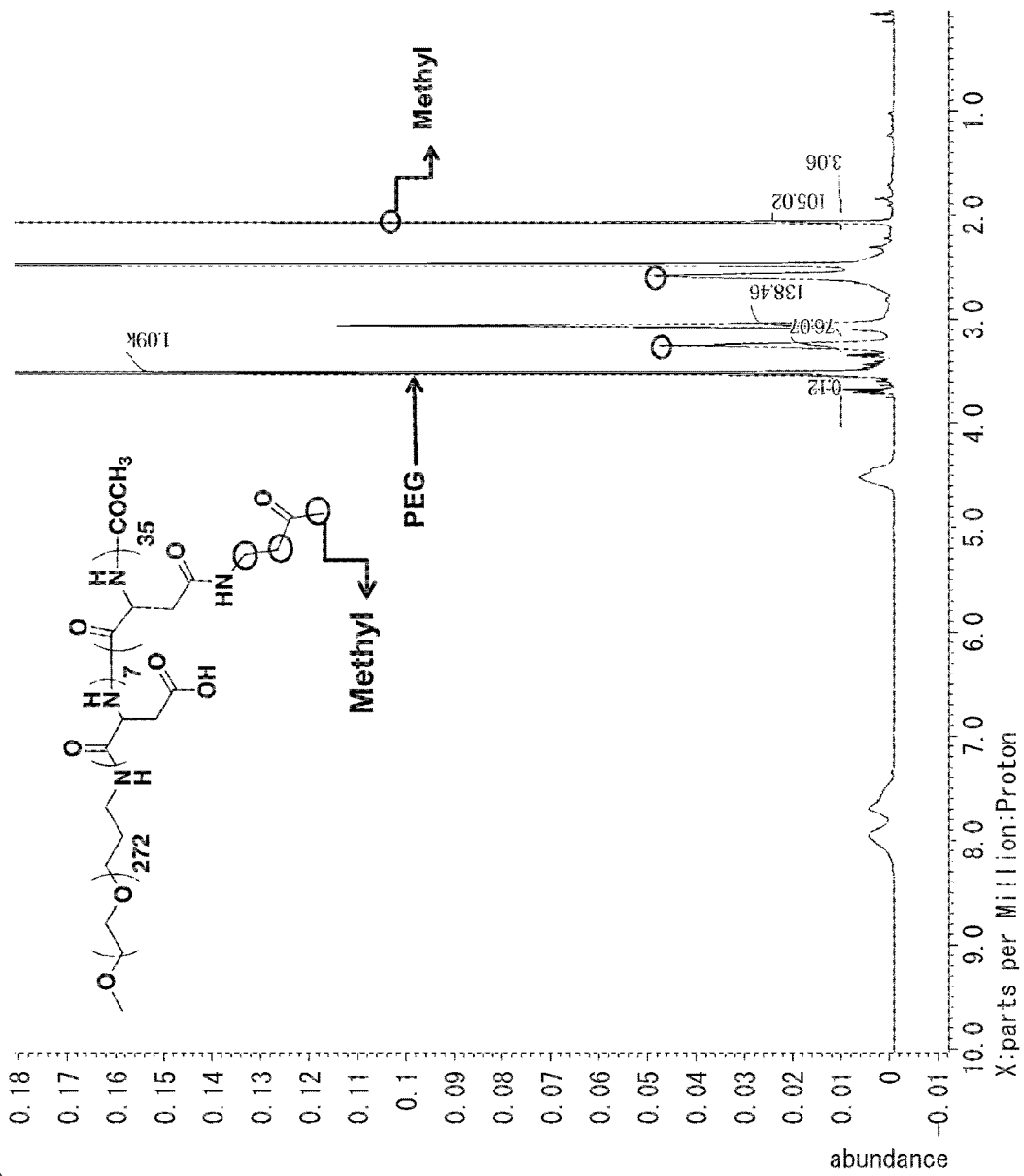
FIG. 15 shows a $^1$H-NMR spectrum of an aliphatic ketone group-containing polymer according to an embodiment of the present invention.

The reaction scheme is shown in FIG. 14. Further, the $^1$H-NMR analysis results for the obtained aliphatic ketone group-containing polymer are shown in FIG. 15. It was confirmed that 35 aliphatic ketone units were introduced to the polymer.

Example 5

Preparation (2) of Drug Conjugate

The reaction between DAVLBH obtained in Example 1 and the aliphatic ketone-containing polymer obtained in Synthesis Example 5 was carried out in a DMSO solution in a temperature range of 35° C. to 40° C. for 72 hours, and the solvent was exchanged for dimethylacetamide (DMAc) by dialysis (dialysis for 4 hours, the dialysis solvent was exchanged once). A transparent DMAc solution was generated due to this solvent exchange.

<Preparation of DAVBNH Bonded Polymer Micelle>

The DMAc solution obtained in the above-described manner was used for preparation of a micelle. The DMAc solution of the drug conjugate was added dropwise to water such that the volume ratio of the solution to water was set to 1 to 10 and vortexed to prepare a micelle. This solution was dialyzed with water in a dialysis bag having a molecular cutoff (MWCO) of 3500 Da for 24 hours. The dialysis solvent was exchanged five times during the dialysis. The solution in the dialysis bag was filtered with a filter (0.22 μm) and concentrated by ultrafiltration using a 100 kDa MWCO filter membrane. The load amount of DAVBNH was 33%.

<Measurement of Micelle Size and PDI>

Figure 16:
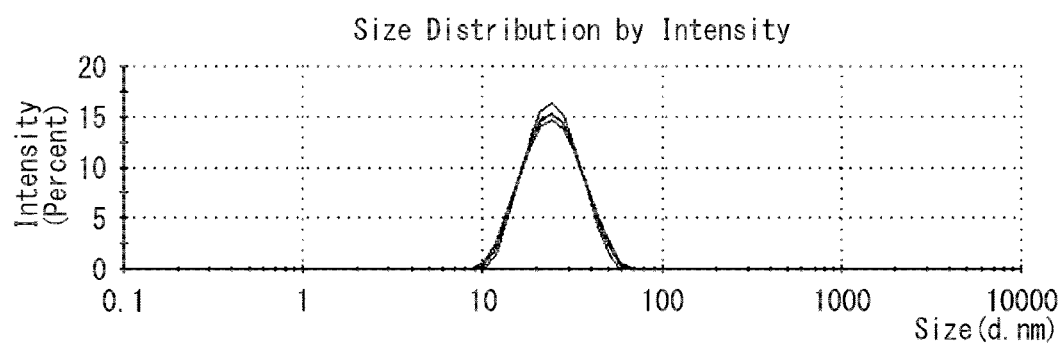
FIG. 16 shows analysis results for the polydispersion index (PDI) and the micelle size of a drug conjugate according to an embodiment of the present invention.

The micelle size and the polydispersion index (PDI) were acquired using a dynamic light scattering (DLS) technique in the same manner as in Example 1. The results are shown in FIG. 16.

<Evaluation of pH Sensitive Release>

The polymer micelle DMAc solutions of Examples 1 and 5 were respectively diluted with 975 μL of a phosphate butter at different pHs and cultured at 37° C. for 48 hours. The drug release from each polymer micelle DMAc solution at a predetermined time was measured. The conditions of HPLC analysis are as follows.

HPLC (TSKgel ODS-80Tm C18 column 4.6×150 mm, manufactured by Tosoh Corporation)

Solvent: mixed uniform solvent containing 20 mM phosphoric acid buffer (pH of 2.5) and methanol at mixing ratio of 1:1

Flow rate: 0.6 mL/min

UV detection: wavelength of 220 nm

Figure 17:
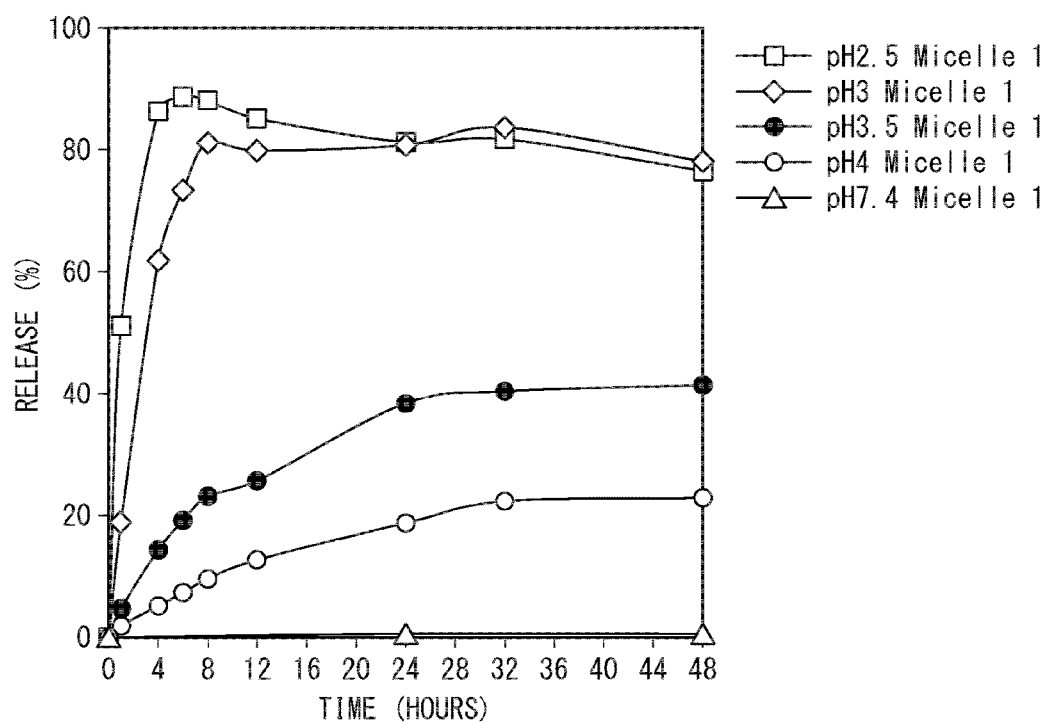
FIG. 17 is a graph showing a pH sensitive drug release profile of a drug conjugate according to an embodiment of the present invention.
Figure 18:
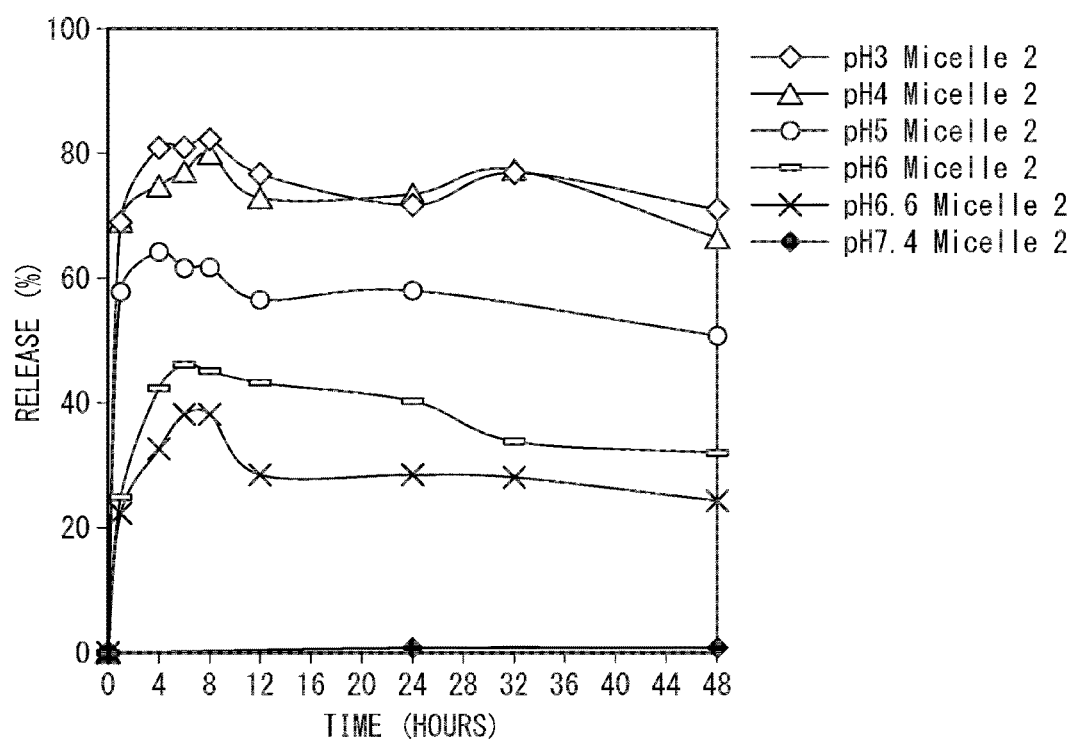
FIG. 18 is a graph showing a pH sensitive drug release profile of a drug conjugate according to an embodiment of the present invention.

The evaluation results for pH sensitive release are shown in FIGS. 17 and 18. FIG. 17 is a graph showing a pH sensitive drug release profile of the polymer micelle solution of Example 1. FIG. 18 is a graph showing a pH sensitive drug release profile of the polymer micelle solution of Example 5.

Based on the results shown in FIGS. 17 and 18, the pH sensitive drug release was confirmed from the polymer micelle solutions of Examples 1 and 5 to which the invention of the present application had been applied. Particularly, in consideration of the environment in the living body, it was confirmed that the aliphatic ketone-containing polymer of Example 5 was excellent in drug release in the environment (pH of 6.6) surrounding acidifying cancer and endosomes (pH of 5) after the drug had been incorporated into the cytoplasm.

Example 6

Cytotoxicity Test (2) of Drug Conjugate Against Brain Tumor Cells

The in vitro cytotoxicity of the DAVBNH bonded polymer micelle of Example 5 was evaluated using cell-counting kit-8 similar to Example 2 with respect to U87MG serving as a glioma cell strain. The results are listed in Table 3. Further, the results of FIG. 11 are also listed in Table 3 for reference.

TABLE 3

| | IC50 [nM] | |
|---|---|---|
| Sample name | 48 hours | 72 hours |
| Vinblastine sulfate | 1.4 | 1.7 |
| DAVBNH bonded polymer micelle (Example 1: aromatic aldehyde group-containing polymer) | 110 | 65 |
| DAVBNH bonded polymer micelle (Example 5: aliphatic ketone group-containing polymer) | 4.1 | 1.4 |

Reference Example 1

Evaluation of Maximum Tolerated Dose (MTD) of DAVBNH

DAVBNH was administered to mice (BALB/c Nude, female, 6 weeks old) four times (0 day, 3rd day, 6th day, 9th day) every four days, and the maximum tolerated dose (MTD) was evaluated. The administration groups were prepared as follows, and the number of mice in each group was set to 3. The results are shown in FIG. 19.

Figure 19:
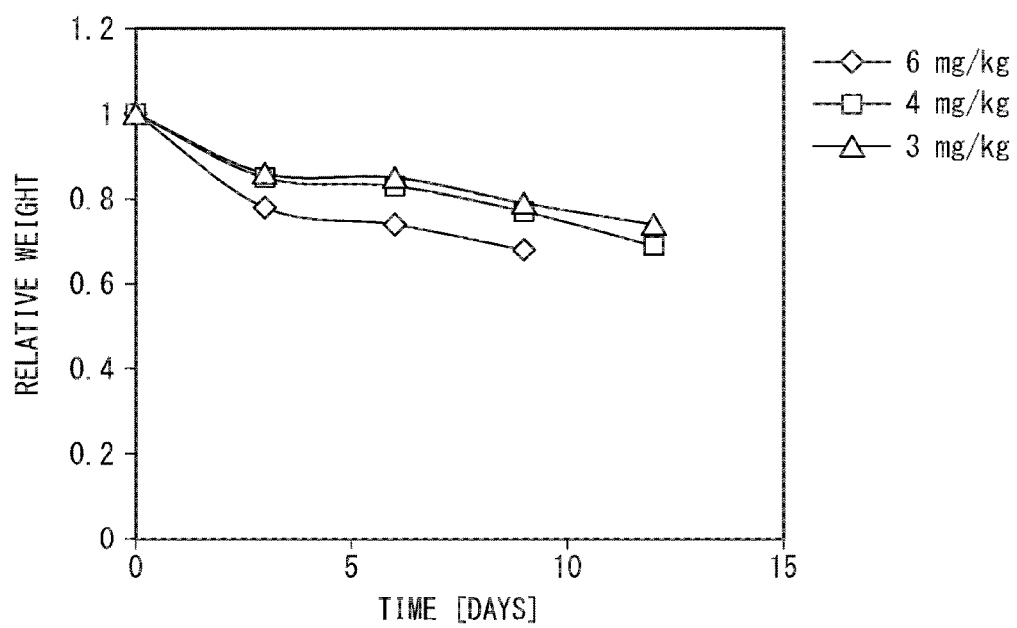
FIG. 19 is a graph showing changes in weights of mice with time in a case where DAVBNH is administered to the mice.

Administration group 1: 3 mg/kg of DAVBNH
Administration group 2: 4 mg/kg of DAVBNH
Administration group 3: 6 mg/kg of DAVBNH FIG. 19 is a graph showing changes in weights of mice with time in a case where DAVBNH is administered to the mice. As shown in FIG. 19, the lethal dose of DAVBNH was confirmed to be 6 mg/kg. Further, a significant weight loss was observed after only 25% of the treatment schedule with a dose of 3 mg/kg.

Example 7

Evaluation of Maximum Tolerated Dose (MTD) of Drug Conjugate

The drug was administered to mice (BALB/c Nude, female, 6 weeks old) four times (0 day, 3rd day, 6th day, 9th day) every four days, and the maximum tolerated dose (MTD) was evaluated. The administration groups were prepared as follows, and the number of mice in each group was set to 5. The results are shown in FIG. 20.

Administration group 1: PBS (control)
Administration group 2: 2 mg/kg of DAVBNH (VinHyd)
Administration group 3: 2 mg/kg of DAVBNH bonded polymer micelle (Example 1)
Administration group 4: 4 mg/kg of DAVBNH bonded polymer micelle (Example 1)
Administration group 5: 16 mg/kg of DAVBNH bonded polymer micelle (Example 1)

Figure 20:
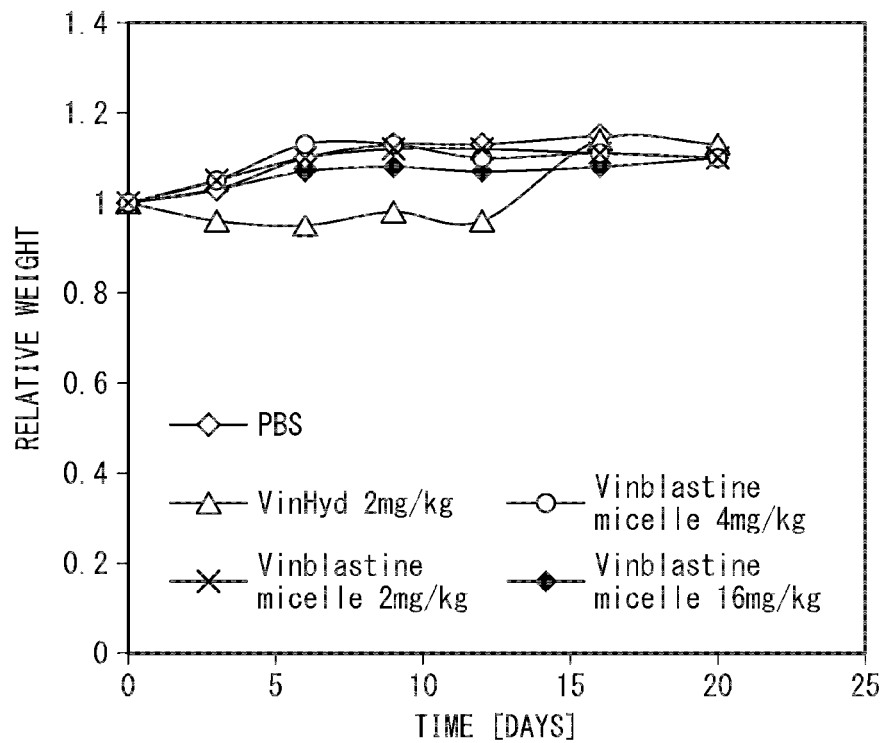
FIG. 20 is a graph showing changes in weights of mice with time in a case where a drug conjugate according to an embodiment of the present invention is administered to the mice.

FIG. 20 is a graph showing changes in weights of mice with time in Example 7. As shown in FIG. 20, a weight loss occurs even in a case where the dose of DAVBNH is 2 mg/kg. Meanwhile, a weight loss does not occur even in a case where the dose of the DAVBNH bonded polymer micelle is 16 mg/kg. Therefore, it was confirmed that the maximum tolerated dose of the DAVBNH bonded polymer micelle increased 8 times or greater the maximum tolerated dose of DAVBNH.

Example 8

Brain Tumor Orthotopic Model

U87MG-Luc2 ($1.0 \times 10^5$ cells in 2 μL) was transplanted into the skull at 1.0 mm fore part and 2.0 mm of the bregma and transplanted into a depth of 3.0 mm from the brain surface of each Balb/c nude mouse.

The tumors were allowed to grow for 5 to 6 days and antitumor activity assays started in three groups (n=6) of BALB/c nude mice.

The administration groups are prepared as follows.
Administration group 1: PBS as control
Administration group 2: 2 mg/kg (MTD) of DAVBNH
Administration group 3: 16 mg/kg (safely tolerated dose) of DAVBNH bonded polymer micelle (Example 1)

The treatment schedule was as follows.
First phase: set as four injections at intervals of two days (0 day, 3rd day, 6th day, and 9th day)
Second phase: set as seven injections every week, and the total treatment period was set to approximately 1.5 months In vivo imaging was performed using an IVIS Spectrum (Xenogen Corporation), and a D-luciferin potassium salt solution was used as a substrate of luciferase.

Figure 21A:
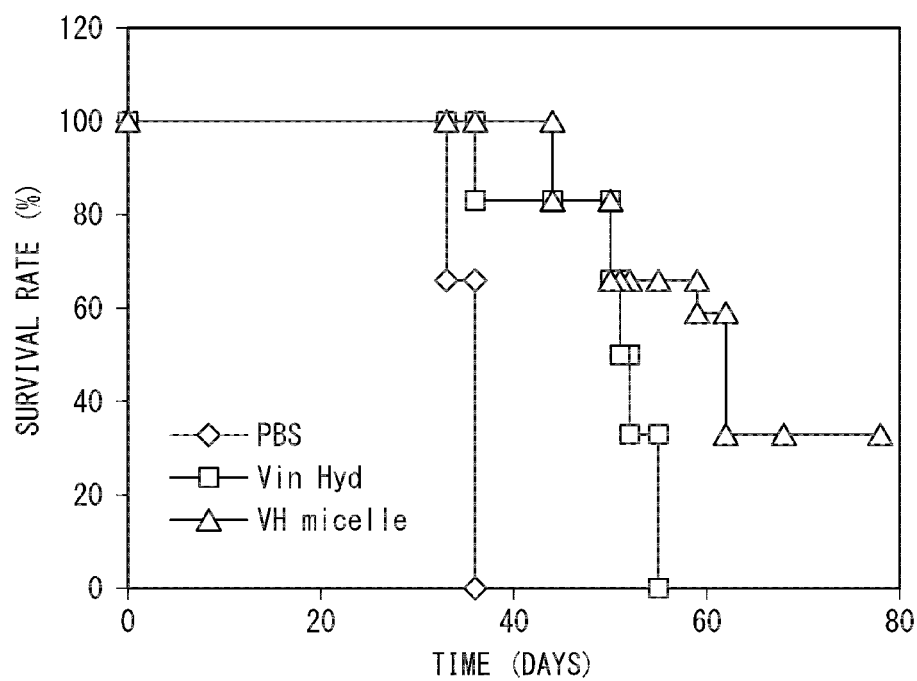
FIG. 21A is a graph showing changes in survival rates with time in a case where a drug conjugate according to an embodiment of the present invention is administered to mice.
Figure 21B:
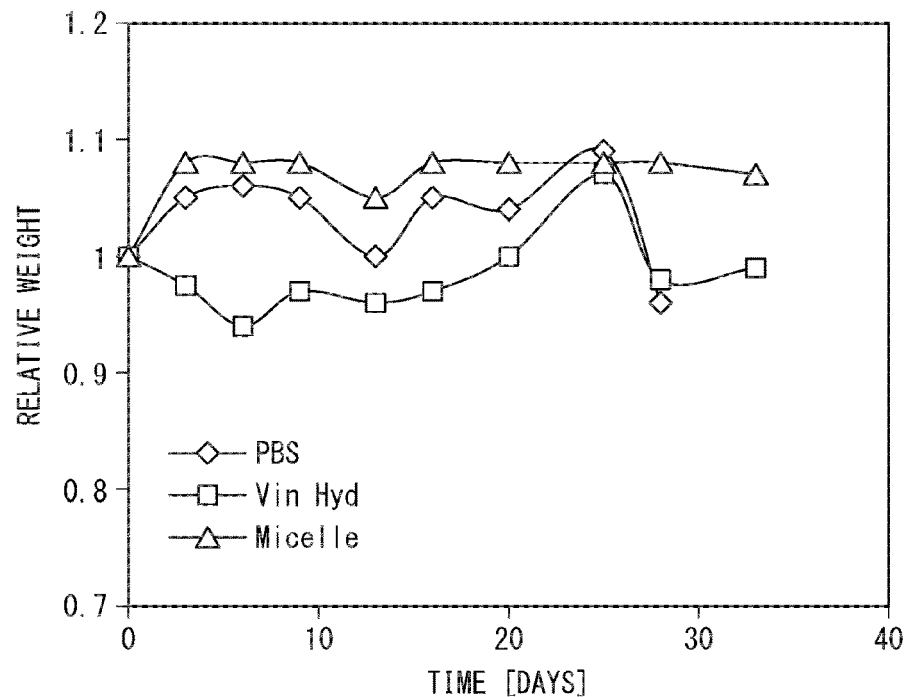
FIG. 21B is a graph showing changes in weights with time in a case where a drug conjugate according to an embodiment of the present invention is administered to mice.

FIG. 21A is a graph showing changes in survival rates with time in Example 8, and FIG. 21B is a graph showing changes in weights with time in Example 8.

Figure 22:
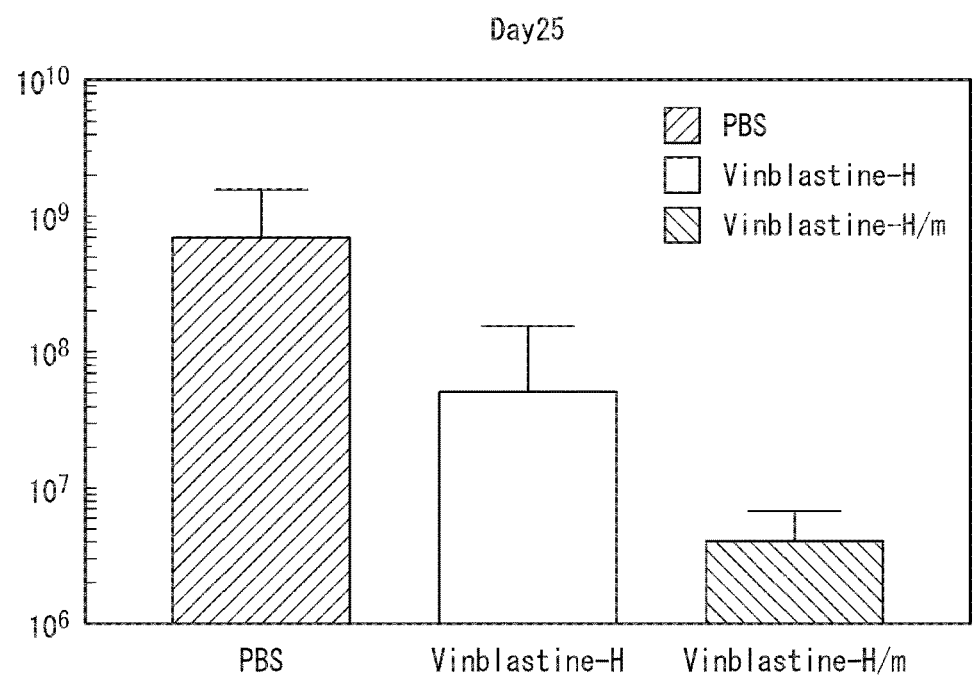
FIG. 22 shows results obtained by performing an in vivo antitumor test on a drug conjugate according to an embodiment of the present invention.

FIG. 22 is a graph showing the contrast of tumor growth on 25th day in each administration group of Example 8.

Figure 23:
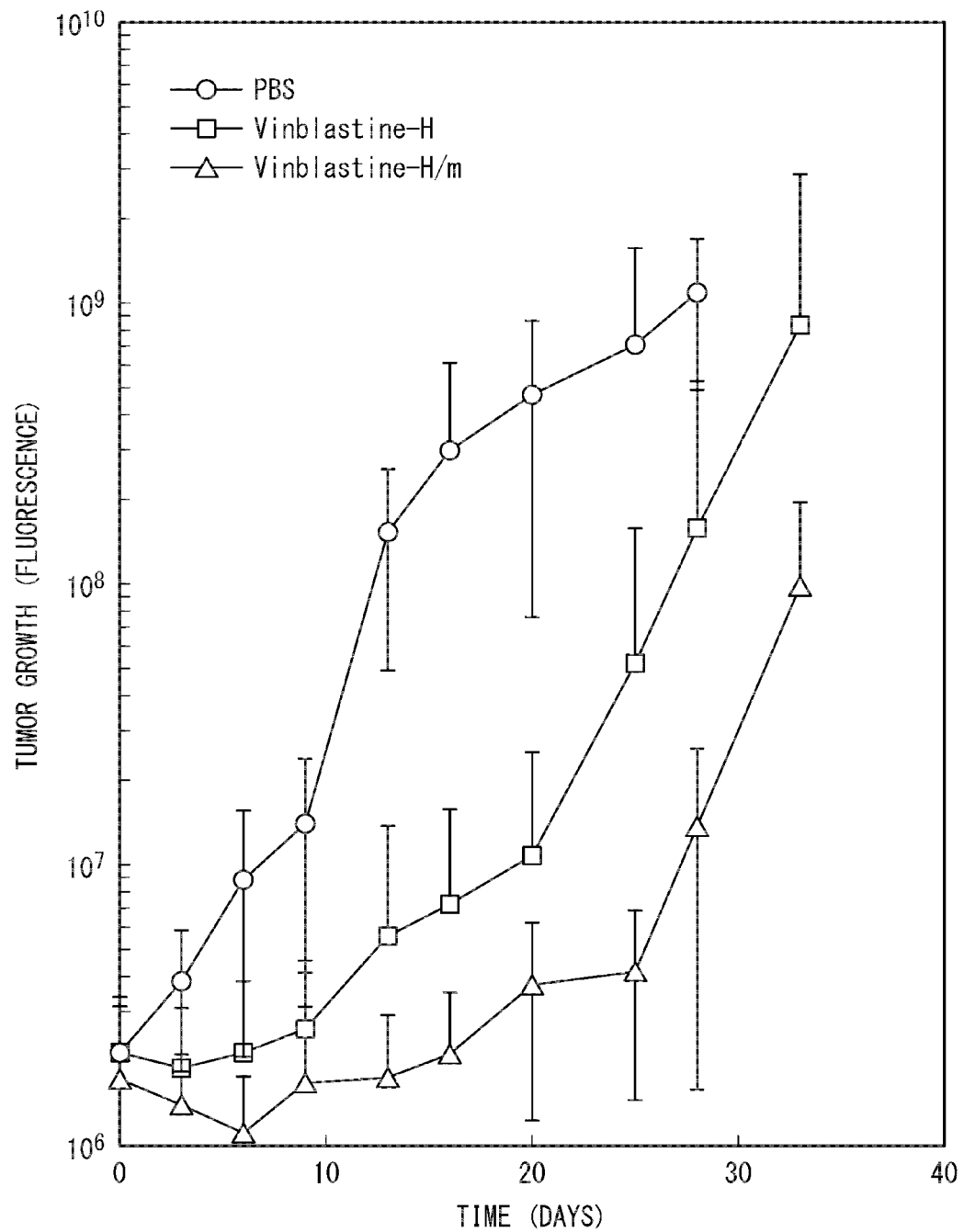
FIG. 23 shows results obtained by performing an in vivo antitumor test on a drug conjugate according to an embodiment of the present invention.

FIG. 23 is a graph showing the tumor growth curves in each administration group of Example 8.

Based on the results shown in FIGS. 21A, 21B, 22, and 23, it was confirmed that the DAVBNH bonded polymer micelle significantly reduced the brain tumor by carrying out tail vein injection in the brain tumor orthotopic transplant model and extended survival significantly.

In Example 8, DAVBNH (2 mg/kg) having a maximum tolerated dose and the DAVBNH bonded polymer micelle (16 mg/kg) having a safely tolerated dose were used. Therefore, it was confirmed that the treatment using DAVBNH has no room for improvement, but the treatment using DAVBNH bonded polymer micelle has room for improvement.

Example 9

Preparation of Drug Conjugate with K252a-Hydrazide (K252a-H)

<Synthesis of K252a-H>

Figure 24:
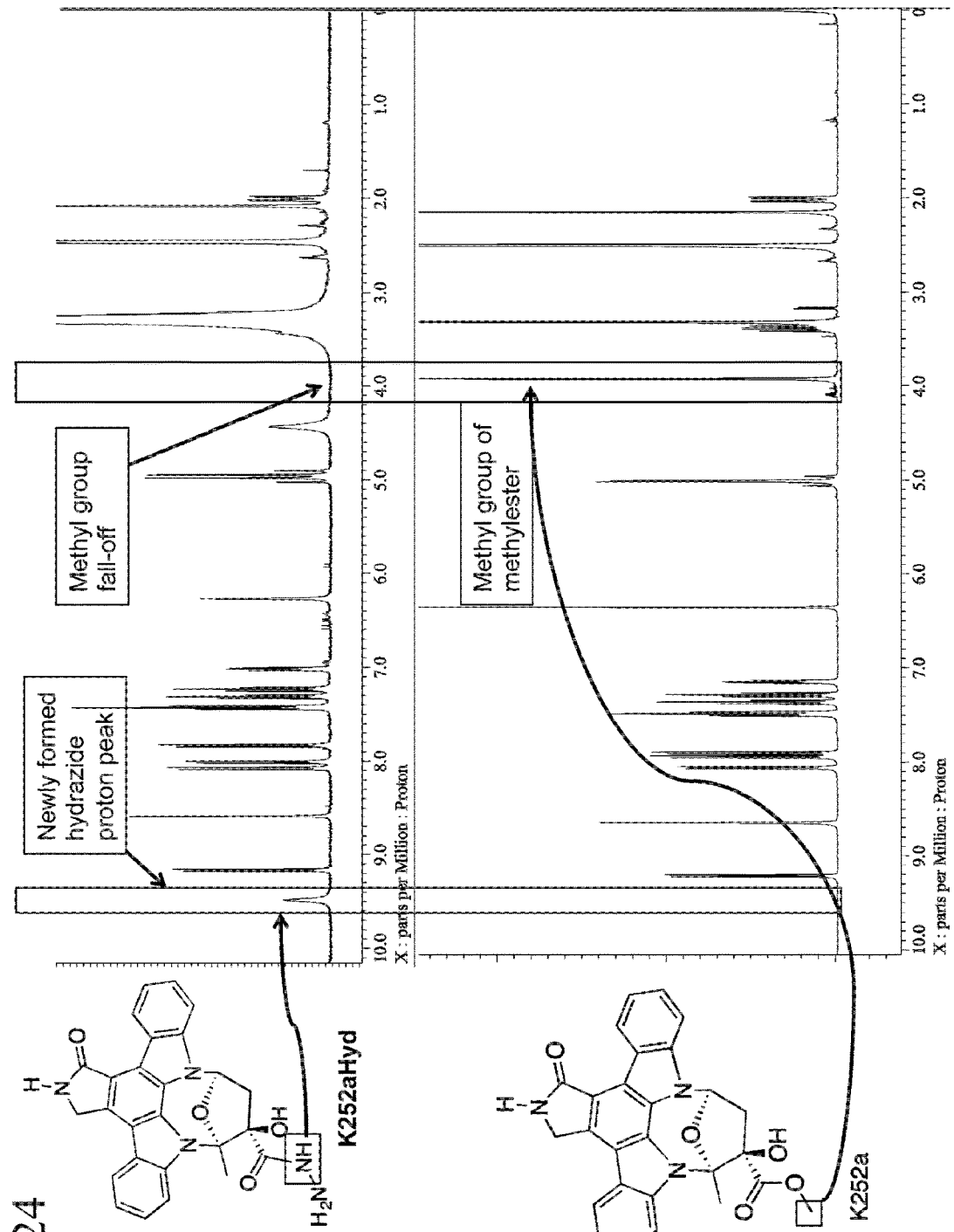
FIG. 24 shows a $^1$H-NMR spectrum of K252a and K252a hydrazide (K252a-H).
Figure 25:
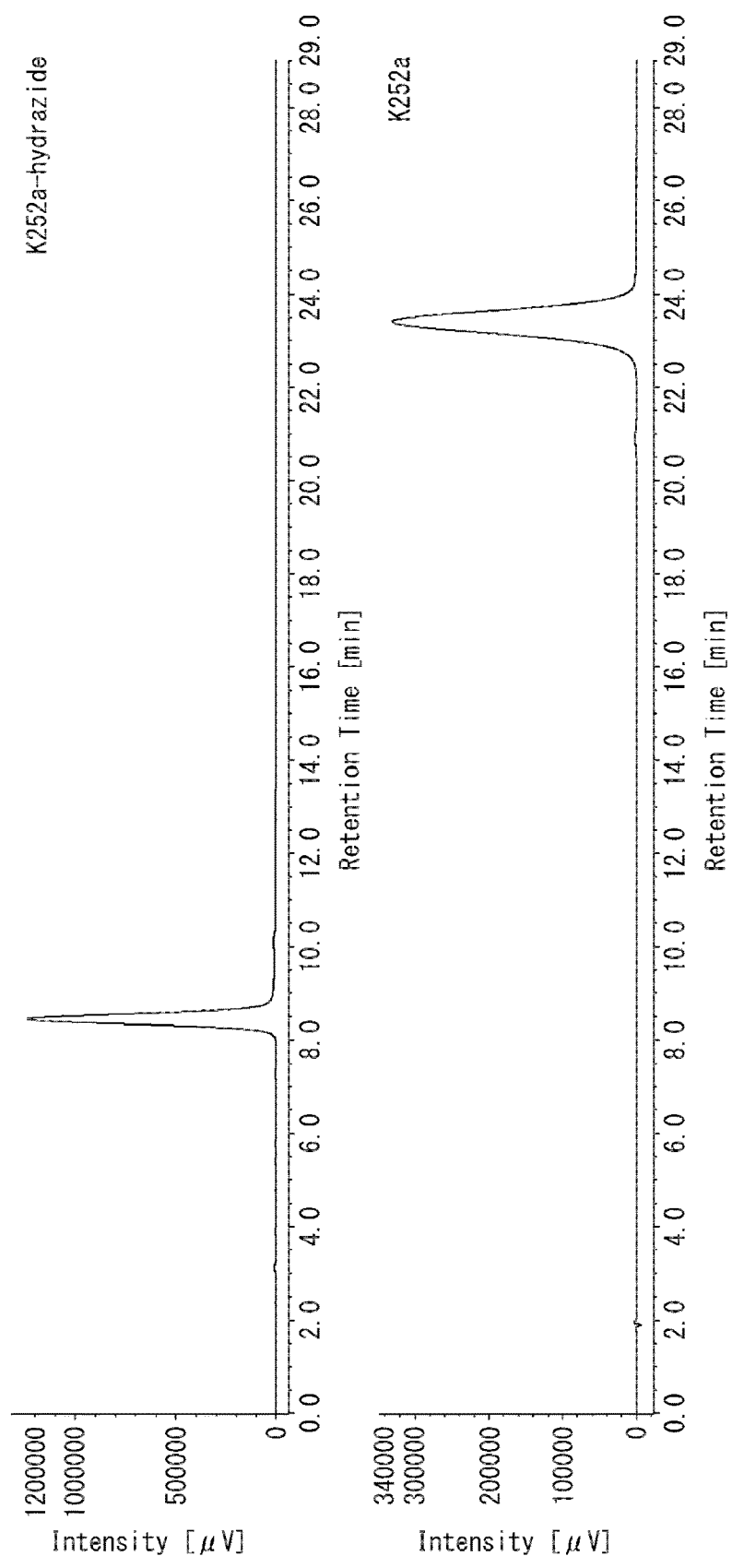
FIG. 25 shows HPLC analysis results for K252a and K252a-H.

K252a was purchased from BOC Science (US). The K252a (20 mg) was dissolved in anhydrous methanol (200 μL), and the solution was added to anhydrous hydrazine (300 μL). The reaction mixture was stirred at 40° C. for 15 hours. The reaction mixture was evaporated to obtain a dried product. In the evaporation, toluene was used as a co-evaporation solvent. The obtained product was used for preparation of a drug conjugate and a micelle without carrying out further purification. The $^1$H-NMR analysis results for the obtained product are shown in FIG. 24. In the obtained product, the methyl group of K252a disappeared and a peak of the hydrazide group proton was confirmed. Accordingly, it was confirmed that K252a-H was obtained. Further, K252a-H was analyzed by HPLC. The analysis results are shown in FIG. 25. It was confirmed that both of K252a-H and K252a have different structures because the retention times are different from each other. The conditions for HPLC analysis are as follows.

TSK-GEL ODS-100V column 4.6×150 mm, particle diameter of 5 μm (Tosoh Corporation)

Colum pressure: 10.7 MPa

Column temperature: constant temperature around 40° C.

Mobile phase: mixed solution containing methanol and formic acid buffer (pH of 3.0) at mixing ratio of 3:2

Flow rate: 1.2 mL/min, 20 to 30 minutes

UV detection: wavelength of 290 nm

Further, the synthesis scheme for K252a-H from K252a is shown below.

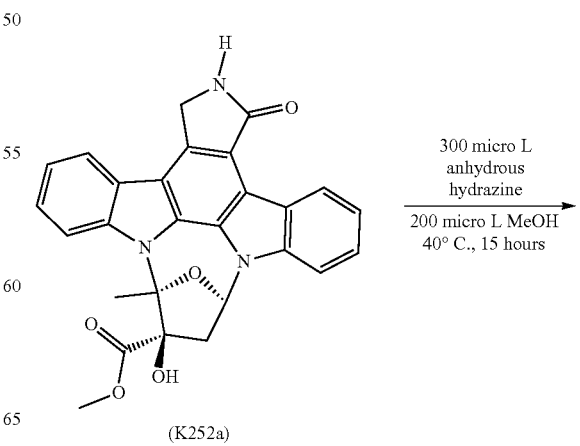

(K252a)

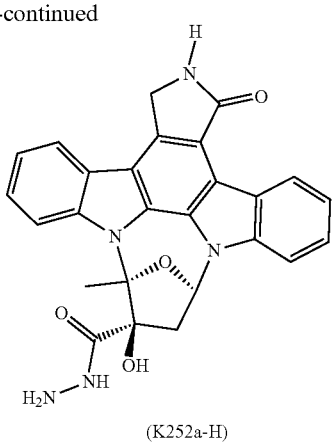

(K252a-H)

<Preparation of Drug Conjugate>

The reaction between the product (K252a-H) and the aromatic aldehyde group-containing polymer or the aliphatic ketone-containing polymer, obtained in the above-described manner, was carried out in a DMSO solution in a temperature range of 35° C. to 40° C. for 72 hours, and the solvent was exchanged for dimethylacetamide (DMAc) by dialysis (dialysis for 4 hours, the dialysis solvent was exchanged once). A transparent DMAc solution was generated due to this solvent exchange.

<Preparation of K252a-H Bonded Polymer Micelle>

The DMAc solution obtained in the above-described manner was used for preparation of a micelle. The DMAc solution of the drug conjugate was added dropwise to water such that the volume ratio of the solution to water was set to 1 to 10 and vortexed to prepare a micelle. This solution was dialyzed with water in a dialysis bag having a molecular cutoff (MWCO) of 3500 Da for 24 hours. The dialysis solvent was exchanged five times during the dialysis. The solution in the dialysis bag was filtered with a filter (0.22 μm) and concentrated by ultrafiltration using a 100 kDa MWCO filter membrane.

<Measurement of Micelle Size and PDI>

Figure 26A:
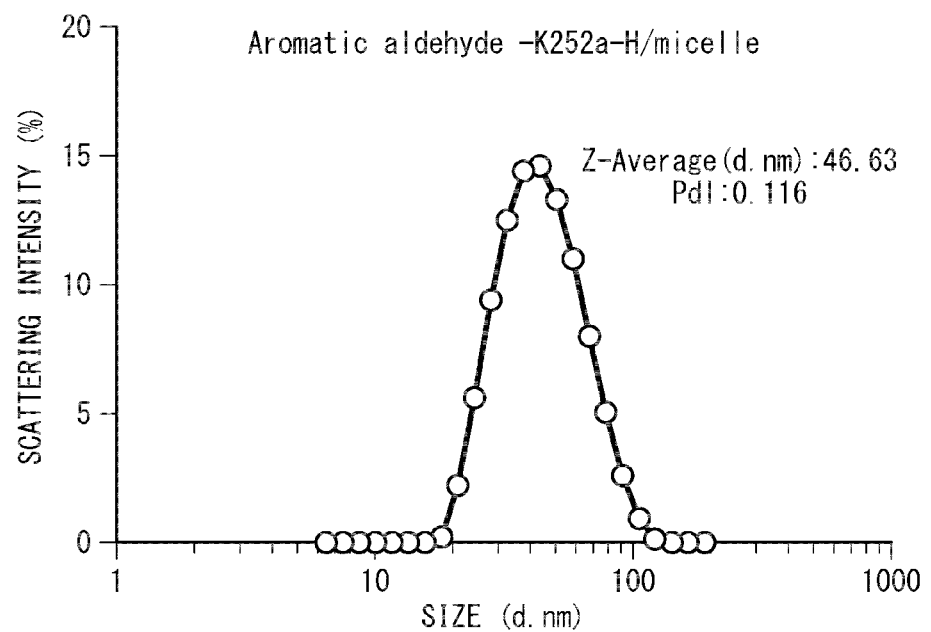
FIG. 26A shows analysis results for the polydispersion index (PDI) and the micelle size of a drug conjugate (K252a-H bonded aromatic polymer micelle) according to an embodiment of the present invention.
Figure 26B:
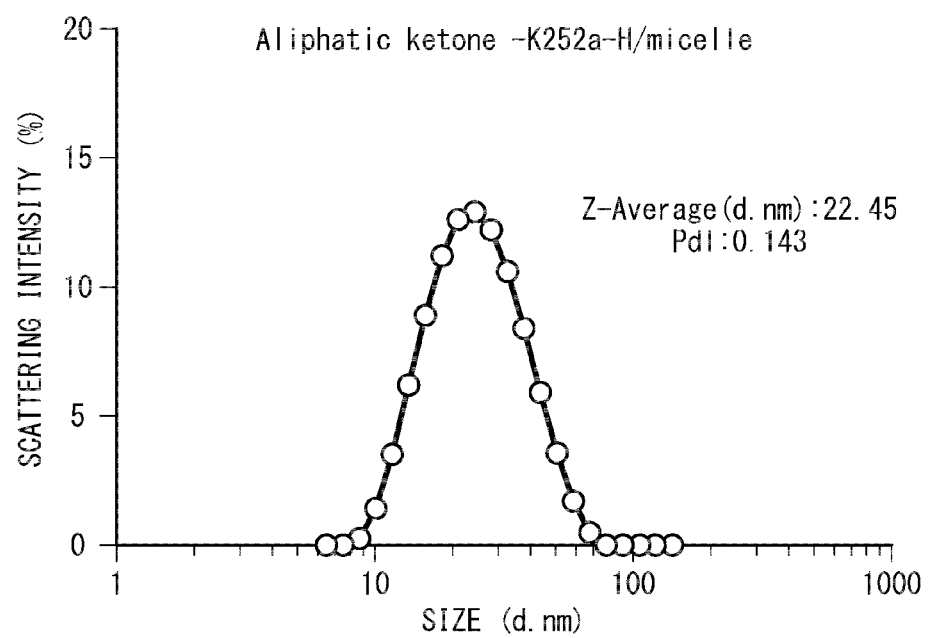
FIG. 26B shows analysis results for the polydispersion index (PDI) and the micelle size of a drug conjugate (K252a-H bonded aliphatic polymer micelle) according to an embodiment of the present invention.

The micelle size and the polydispersion index (PDI) were acquired using a dynamic light scattering (DLS) technique. The measurement was performed using a green laser (532 nm) as an incident beam and Zetasizer nano ZS (Malvern instruments, UK) at a detection angle of 173° under a temperature condition of 25° C. The results are shown in FIGS. 26A and 26B. FIG. 26A shows a micelle (hereinafter, referred to as a "K252a-H bonded aromatic polymer micelle") of a drug conjugate of an aromatic aldehyde group-containing polymer and K252a-H and FIG. 26B shows a micelle (hereinafter, referred to as a "K252a-H bonded aliphatic polymer micelle") of a drug conjugate of an aliphatic ketone group-containing polymer and K252a-H.

Example 10

Solubilization Test of K252a-H and Drug Conjugate Micelle in Water

Figure 27:
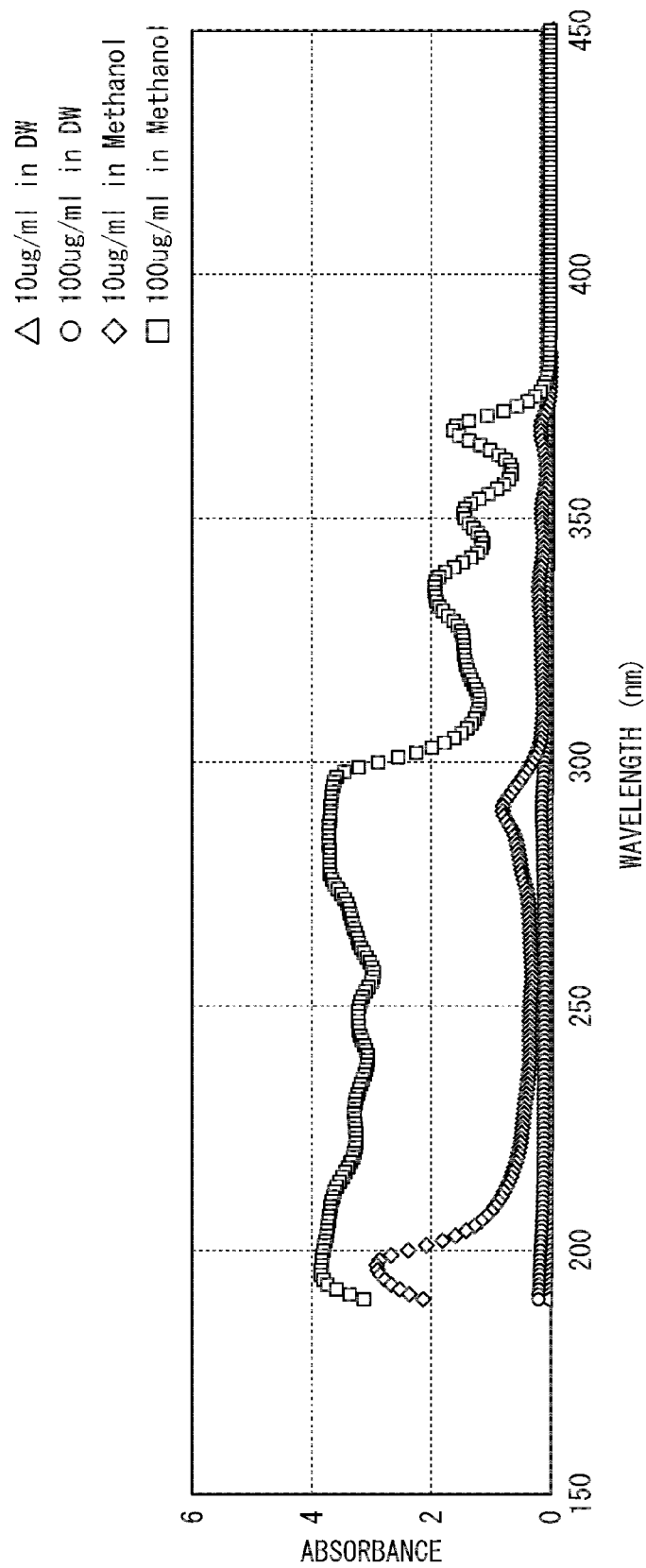
FIG. 27 is an ultraviolet absorption spectrum of a drug conjugate according to an embodiment of the present invention.

K252a-H powder was dissolved in distilled water or methanol at a ratio of 1 mg/mL and the solution was sufficiently mixed. Thereafter, the solution was filtered using a filter having a pore diameter of 22 μm. The ultraviolet absorption spectrum of the filtrate prepared as described above was measured using a spectrophotometer (Jasco V670). The results are shown in FIG. 27. Based on the results of FIG. 27, it was confirmed that K252a-H was only dissolved in water at a ratio of 1 μg/mL or less.

Meanwhile, the K252a-H bonded aromatic polymer micelle and the K252a-H bonded aliphatic polymer micelle were dissolved in water, and the concentration of K252a-H was measured using HPLC. As the result, it was confirmed that K252a-H exhibited solubility in water at a ratio of 2 mg/mL or greater (not shown). Based on the results described above, even in a case of a compound which is hardly soluble in water, such as K252a-H, it was found that the solubility of the compound in water can be increased by forming the compound into a micelle.

Example 11

Release of K252a-H from K252a-H Bonded Polymer Micelle

Figure 28:
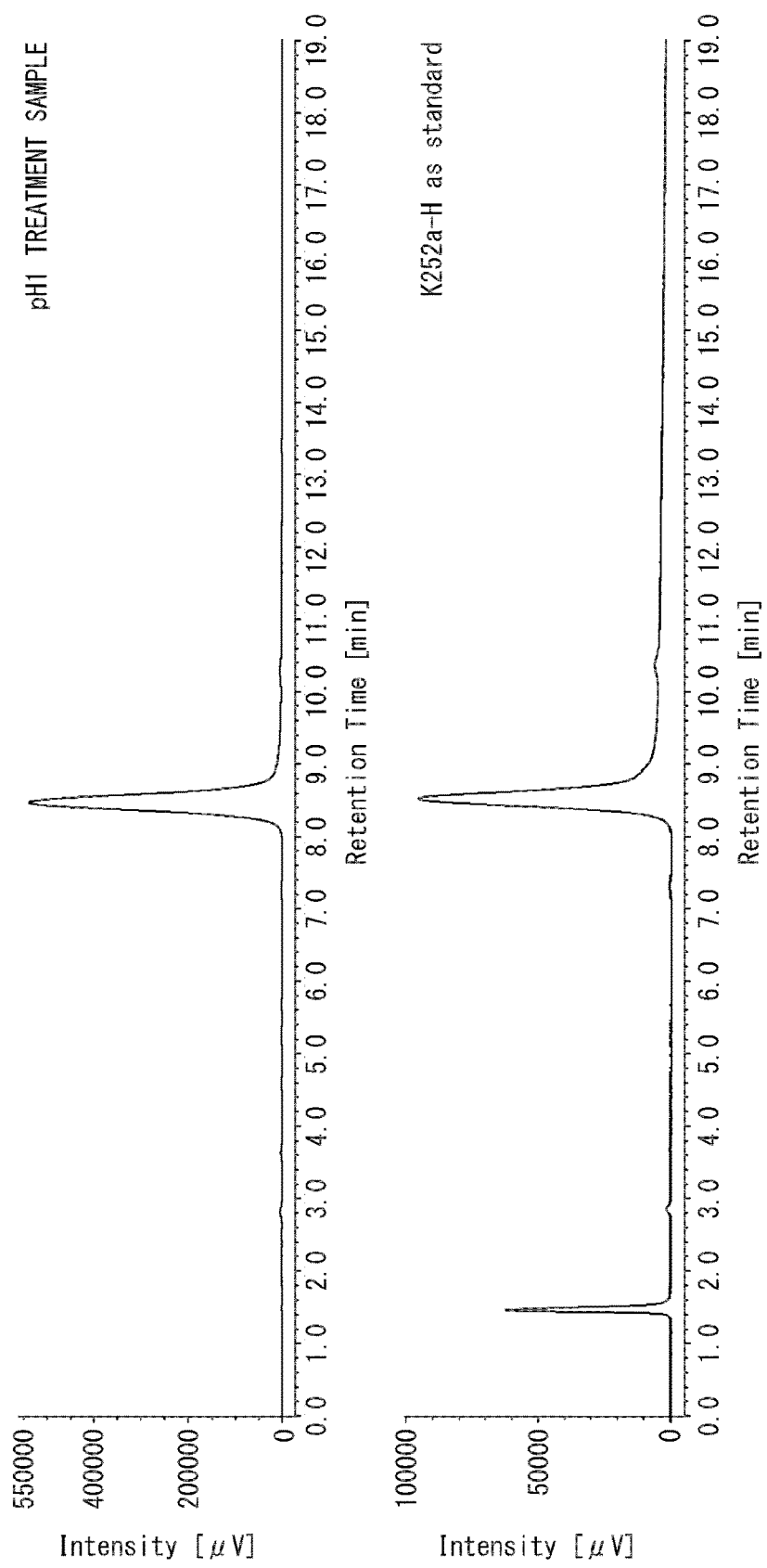
FIG. 28 shows HPLC analysis results for a sample after a drug conjugate according to an embodiment of the present invention is subjected to a treatment using an aqueous buffer having a pH of 1.

The K252a-H bonded aliphatic polymer micelle was incubated in an aqueous buffer having a pH of 1 (methanol: formic acid buffer (pH of 3)=3:2) at 37° C. for 1 hour. Thereafter, HPLC analysis was performed. The HPLC conditions are the same as those in Example 9. The results are shown in FIG. 28. Since the same peak as the peak of K252a-H was confirmed in the sample after being subjected to the treatment using an aqueous buffer having a pH of 1, it was found that K252a-H was released from the K252a-H bonded aliphatic polymer micelle under an acidic condition.

Example 12

Cytotoxicity Test of K252a-H Bonded Polymer Micelle Against Lung Cancer Cells

The cytotoxicity test was performed on the K252a-H bonded aromatic polymer micelle and the K252a-H bonded aliphatic polymer micelle using the lung cancer cell strains listed in Table 4.

Further, in the following example, the used cell strains were purchased from the cell bank of American Type Culture. Collection, ATCC or National Institutes of Biomedical Innovation, Health and Nutrition (JCRB). PC14 PE6 was distributed from Profession Hosho (Tottori University). As the culture medium, DMEM, RPMI, or E-MEM was used unless otherwise specified. Gefitinib, Afatinib, Erlotinib, Cisplatin, Pemetrexed, and Gemicitabine were purchased from Funakoshi Co., Ltd. Osimertinib was purchased from Sellek Chemicals LLC.

TABLE 4

| Lung cancer cell strains | Cancer type | characteristics |
|---|---|---|
| PC14 | Non small cell cancer | PTEN |
| PC14-E6-luc | Non small cell cancer | Metastatic strain PTEN of PC14 into thoracic cavity |
| A549 | Non small cell cancer | CDKN2A(p16), KRAS, SMARCA4, STK11 |
| H358 | Non small cell cancer | K-Ras |
| H460 | Large cell cancer | PIK3CA |
| NCI-1650 | Non small cell cancer | EGFR E746_A750del |
| H2228 | Non small cell cancer | EML4-ALK |
| H1975 | Non small cell cancer | L858R/T790M EGFR Gatekeeper mutation |
| H520 | Non small cell cancer | EGFR deficient strain |

2000 cells/50 μL of a cell solution was adjusted to have an appropriate amount, and 50 μL of the solution was each seeded to the rows 2 to 2 of a 96-well plate. Only a culture medium (DMEM culture medium containing 10% FBS) was added to the raw 1. After the seeding, the 96-well plate was incubated for 24 hours.

300 μL of a culture medium was added to each of 10 wells of the 24-well plate. 100 μL of the micelle solution was added to the well 1A of the 24-well plate and stirred by pipetting (approximately 10 times), and 100 μL of the micelle solution was transferred to the well 2B and stirred in the same manner as described above. The same operation was repeated 10 times, and micelle solutions having ten different concentrations were prepared.

50 μL of each micelle solution adjusted in the above-described manner was added to the row 3 to the row 12 of a 96-well plate seeded with cancer cells in descending order of micelle concentrations of the solutions. Only 50 μL of a culture medium was added to the rows 1 and 2. Thereafter, the 96-well plate was incubated. After the incubation, the cells remained, the solutions in the wells were removed, and the cells in each well were washed with 200 μL of the culture medium. Finally, 100 μL of the culture medium was added to each well and the 96-well plate was incubated for 48 hours.

After 48 hours, 10 μL of a cell counting kit-8 solution (DOJINDO) was added to each well. The 96-well plate was incubated again, and the absorbance at a wavelength of 450 nm was measured after 30 minutes, 1 hour, and 2 hours.

Figure 29:
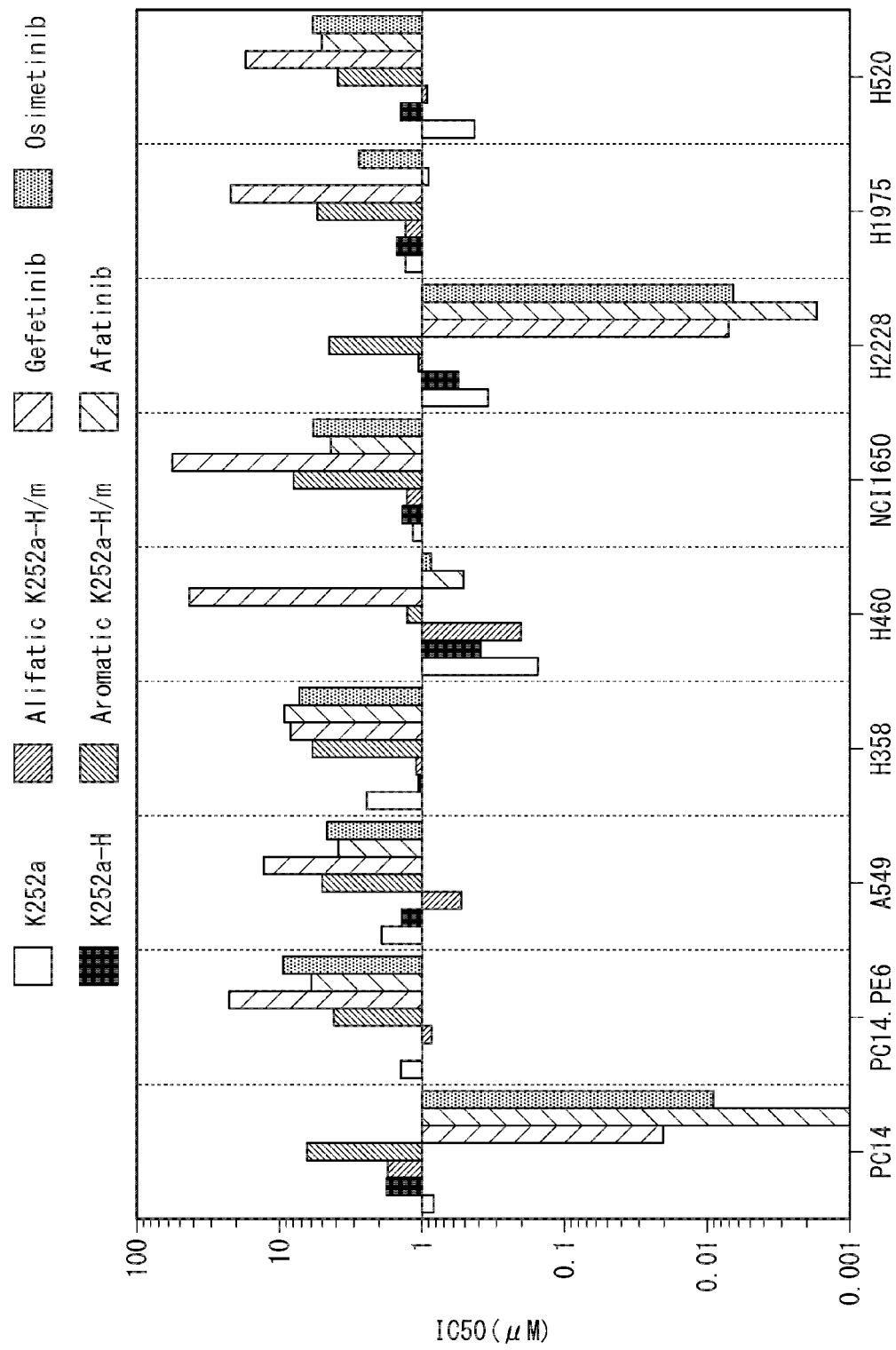
FIG. 29 is a graph showing results of a cytotoxicity test of a drug conjugate according to an embodiment of the present invention against lung cancer cells.

The results are shown in FIG. 29. Gefitinib, Afatinib, and Osimertinib are molecular target drugs for lung cancer which have been currently approved by FDA. Based on the results of FIG. 29, it was found that K252a-H and the K252a-H bonded polymer micelle exhibited excellent cytotoxic activity against lung cancer having resistance to lung cancer treatment drugs of the related art.

Figure 30:
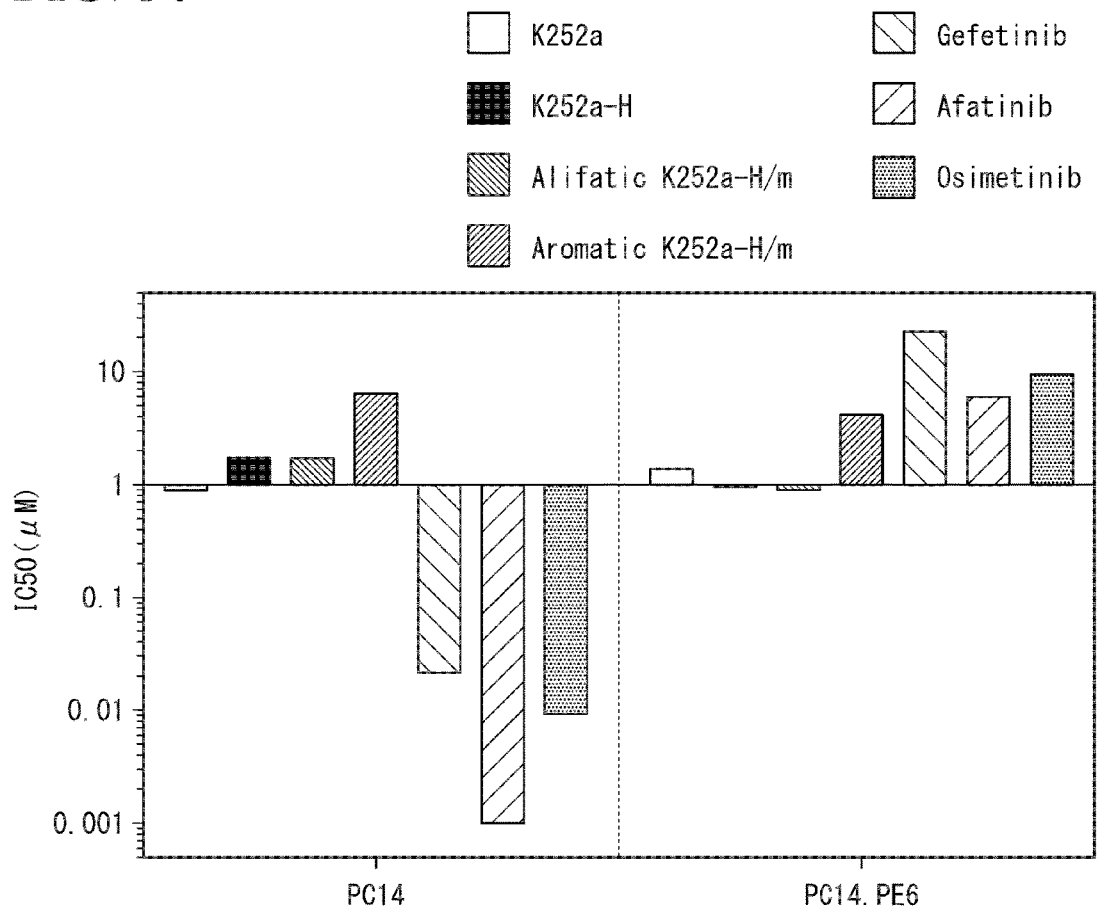
FIG. 30 is a graph showing results of a cytotoxicity test of a drug conjugate according to an embodiment of the present invention against lung cancer cells.

The PC14 strain and the PC14.PE6 strain extracted from FIG. 29 are shown in FIG. 30. The PC14.PE6 strain is a cancer cell strain (Yano et al., Oncology Research 9:573 to 579 (1997)) obtained by performing an operation of administering the PC14 strain to the tail vein of a mouse and establishing the cancer cells metastasized to the thoracic cavity six times. Therefore, the PC14.PE6 strain is a cancer cell strain which is extremely metastatic and malignant. As shown in FIGS. 29 and 30, Gefitinib, Afatinib, and Osimertinib exhibited excellent cytotoxic activity against the PC14 strain. However, the cytotoxic activity of these molecular target drugs of the related art against the malignant PC14.PE6 strain was significantly decreased. Meanwhile, the cytotoxic activity of K252a-H and the K252a-H bonded polymer micelle against the PC14.PE6 strain was increased. These results indicate that K252a-H and the K252a-H bonded polymer micelle are more effective for malignant metastatic cancer. Further, between the K252a-H bonded aromatic polymer micelle and the K252a-H bonded aliphatic polymer micelle, the K252a-H bonded aliphatic polymer micelle tends to exhibit higher cytotoxic activity against cancer cells.

Example 13

Figure 31:
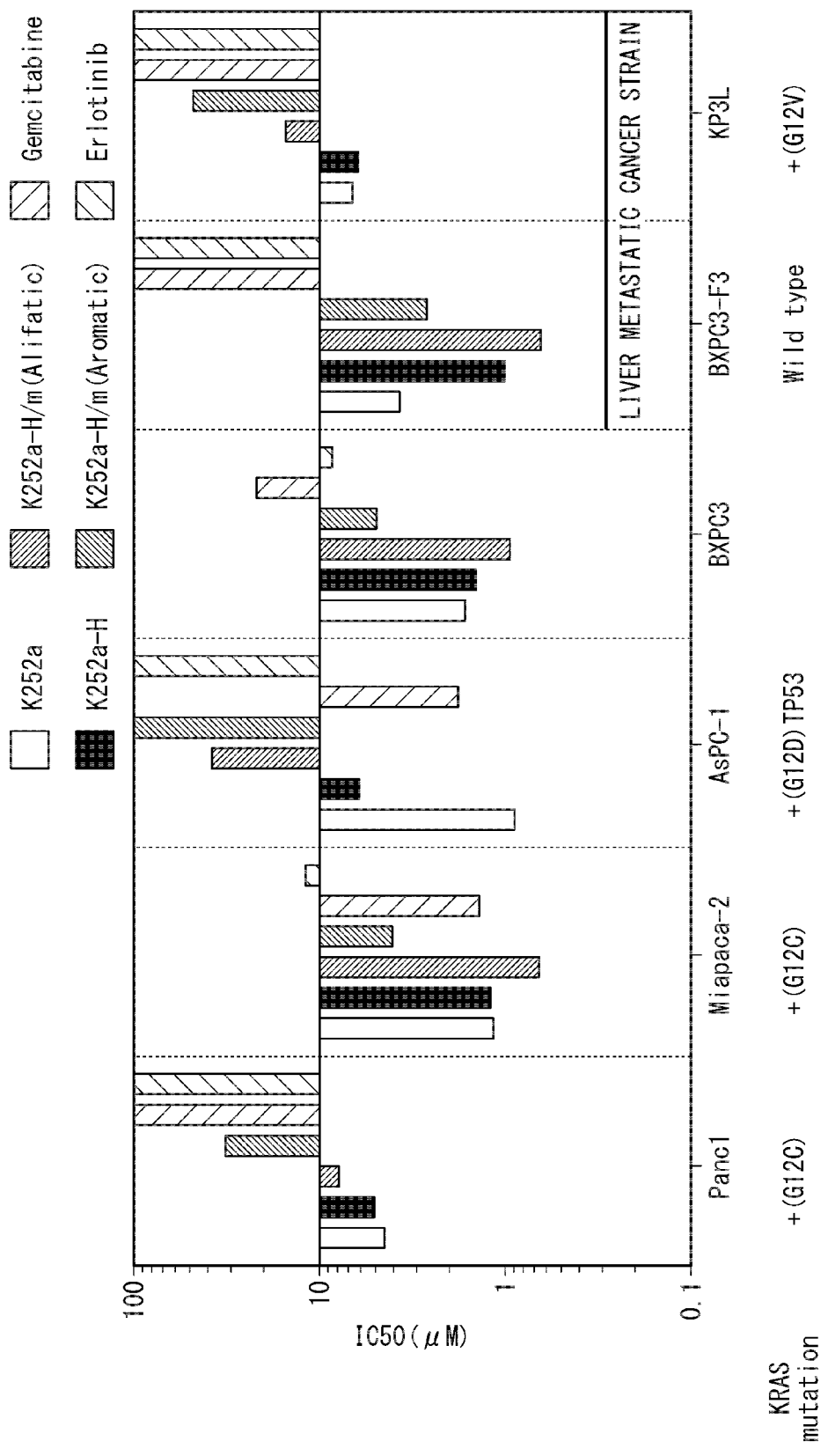
FIG. 31 is a graph showing results of a cytotoxicity test of a drug conjugate according to an embodiment of the present invention against pancreatic cancer cells.

Cytotoxicity Test of K252a-H Bonded Polymer Micelle Against Pancreatic Cancer Cells The cytotoxicity test was performed on the K252a-H bonded aromatic polymer micelle and the K252a-H bonded aliphatic polymer micelle using various pancreatic cancer cell strains in the same manner as described above. The results are shown in FIG. 31. The BXPC3-F3 strain is a metastatic strain which became malignant by performing an operation of establishing a cancer cell strain metastasized to the liver after orthotopic transplant into a mouse, three times. Further, KP-3L is a metastatic strain (available from the cell bank of National Institutes of Biomedical Innovation, Health and Nutrition JCRB) obtained by establishing a cancer cell strain metastasized to the liver after human liver metastatic pancreatic cancer was transplanted to the spleen of a nude mouse. Further, Gemcitabine and Erlotinib are pancreatic cancer treatment drugs which have been currently approved.

As shown in FIG. 31, it was confirmed that K252a-H and the K252a-H bonded polymer micelle are effective for K-ras mutant strains and malignant metastatic strains which are not largely affected by Gemcitabine and Erlotinib. Further, between the K252a-H bonded aromatic polymer micelle and the K252a-H bonded aliphatic polymer micelle, the K252a-H bonded aliphatic polymer micelle tends to exhibit higher cytotoxic activity against cancer cells.

Example 14

Figure 32:
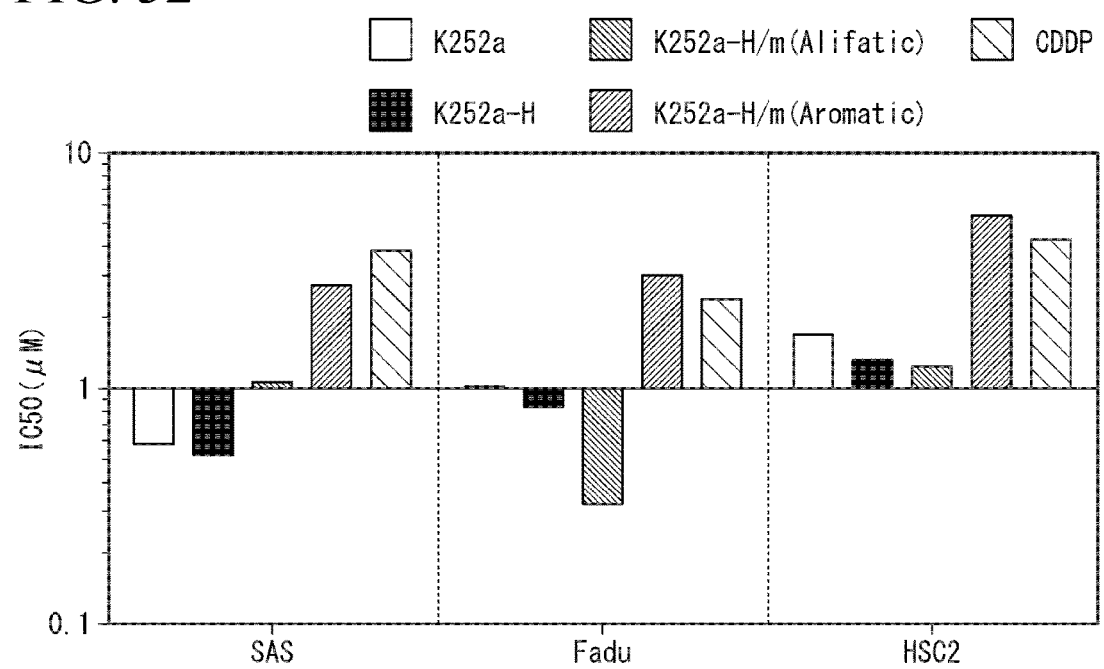
FIG. 32 is a graph showing results of a cytotoxicity test of a drug conjugate according to an embodiment of the present invention against head and neck cancer cells.

Cytotoxicity Test of K252a-H Bonded Polymer Micelle Against Head and Neck Cancer Cells The cytotoxicity test was performed on the K252a-H bonded aromatic polymer micelle and the K252a-H bonded aliphatic polymer micelle using various head and neck cancer cell strains in the same manner as described above. The results are shown in FIG. 32. Further, CDDP indicates Cisplatin serving as a target treatment drug for head and neck cancer.

As shown in FIG. 32, K252a-H and the K252a-H bonded aliphatic polymer micelle exhibited higher cytotoxic activity against all head and neck cancer cell strains than that of Cisplatin. Particularly, in the Fradu strain, the cytotoxic activity of the K252a-H bonded aliphatic polymer micelle was excellent.

Example 15

Cytotoxicity Test of K252a-H Bonded Polymer Micelle Against Mesothelioma Cells

Figure 33:
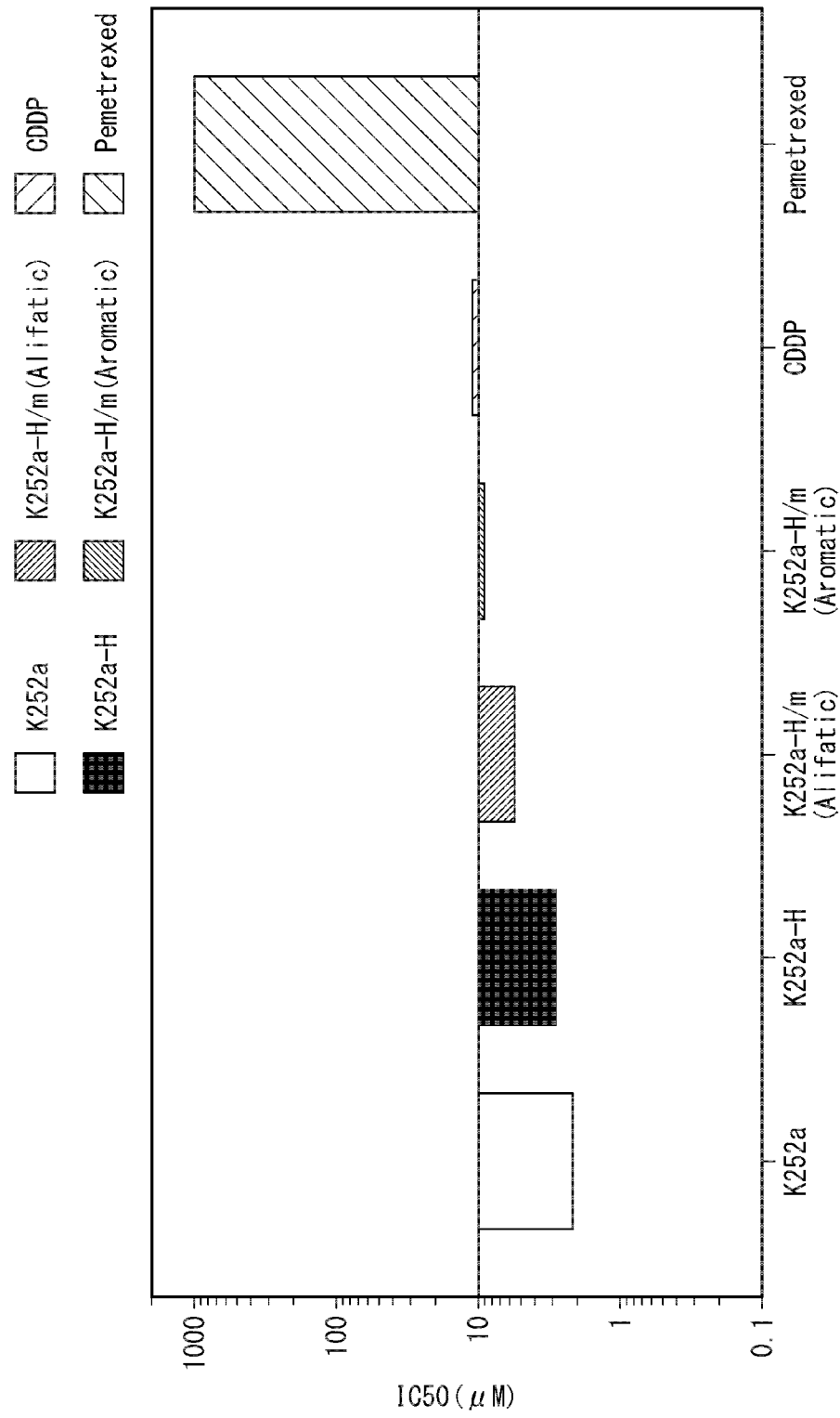
FIG. 33 is a graph showing results of a cytotoxicity test of a drug conjugate according to an embodiment of the present invention against mesothelioma cells.

The cytotoxicity test was performed on the K252a-H bonded aromatic polymer micelle and the K252a-H bonded aliphatic polymer micelle using the mesothelioma cell strain MSTO-211H in the same manner as described above. The results are shown in FIG. 33. Further, CDDP indicates Cisplatin serving as a target treatment drug for mesothelioma. Pemetrexed is also a target treatment drug for mesothelioma.

As shown in FIG. 33, K252a-H and the K252a-H bonded aliphatic polymer micelle exhibited higher cytotoxic activity than that of Cisplatin and Pemetrexed. The K252a-H bonded aromatic polymer micelle exhibited the same level of cytotoxic activity as Cisplatin.

Example 16

Preparation of Drug Conjugate with JQ-1-Hydrazide (JQ-1-H)

<Synthesis of JQ-1-H>

JQ-1 was purchased from BOC Science (US). The JQ-1 (20 mg) was dissolved in anhydrous methanol (500 μL), and the solution was added to anhydrous hydrazine (500 μL). The reaction mixture was stirred at 40° C. overnight. The reaction mixture was evaporated to obtain a dried product.

Figure 34:
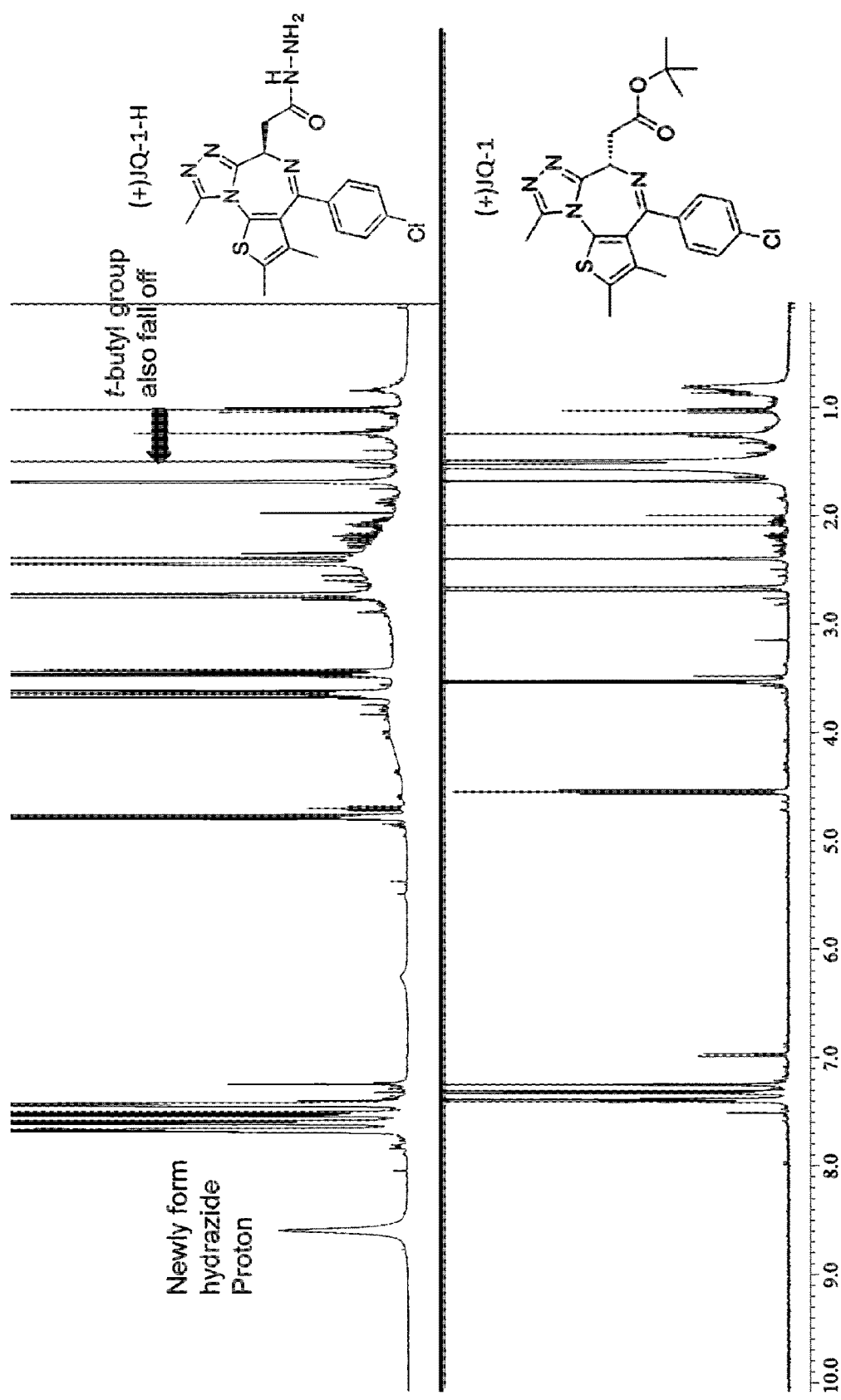
FIG. 34 shows a $^1$H-NMR spectrum of JQ-1 and JQ-1 hydrazide (JQ-1-H).

In the evaporation, toluene was used as a co-evaporation solvent. The obtained product was used for preparation of a drug conjugate and a micelle without carrying out further purification. The $^1$H-NMR analysis results for the obtained JQ-1-H are shown in FIG. 34.

Further, the synthesis scheme of JQ-1-H from JQ-1 is shown below.

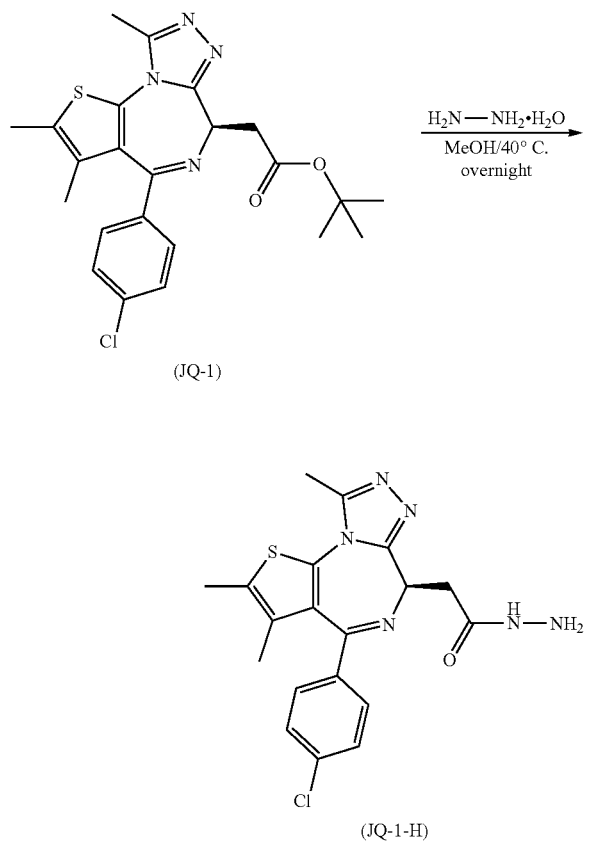

(JQ-1)

(JQ-1-H)

<Preparation of Drug Conjugate>

The reaction between the product (JQ-1-H) and the aromatic aldehyde group-containing polymer, obtained in the above-described manner, was carried out in a DMSO solution in a temperature range of 35° C. to 40° C. for 72 hours, and the solvent was exchanged for dimethylacetanmide (DMAc) by dialysis (dialysis for 4 hours, the dialysis solvent was exchanged once). A transparent DMAc solution was generated due to this solvent exchange.

<Preparation of JQ-1-H Bonded Polymer Micelle>

Figure 35:
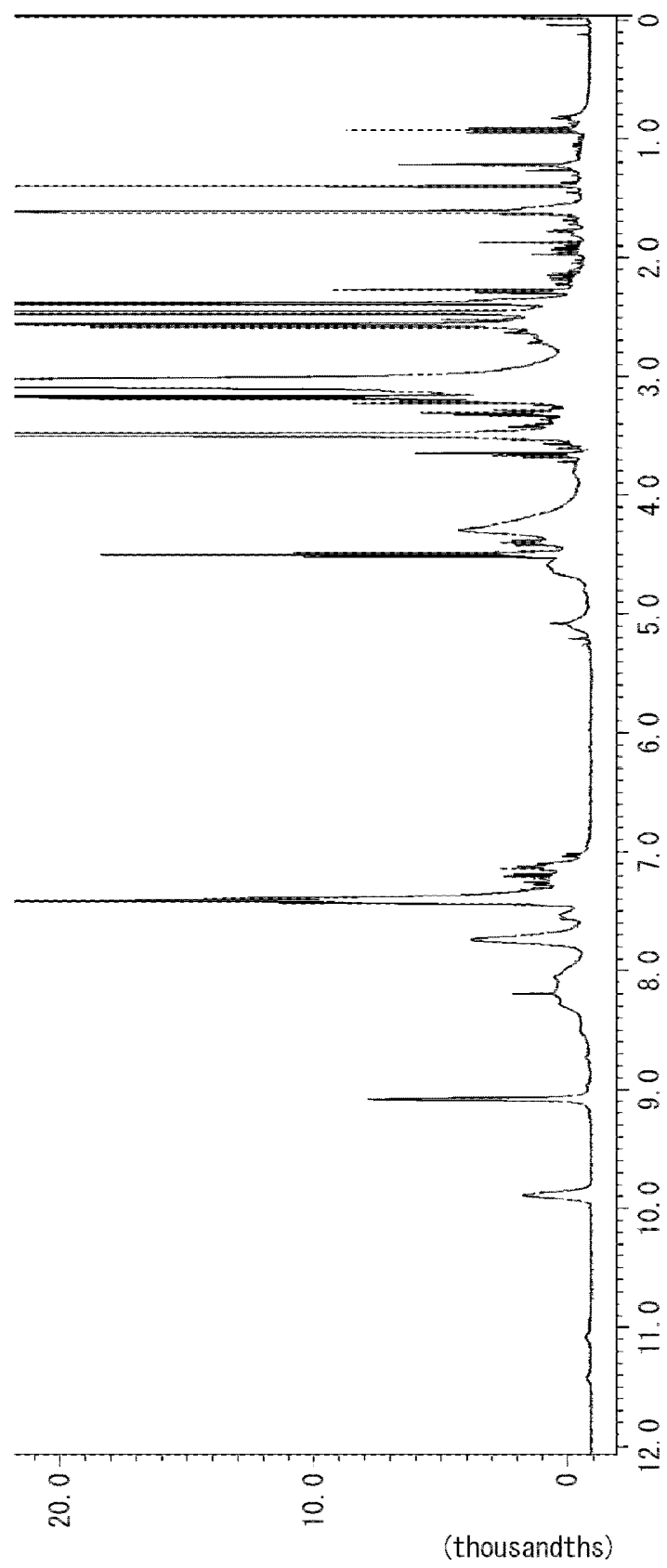
FIG. 35 shows a $^1$H-NMR spectrum of a drug conjugate (JQ-1-H bonded aromatic polymer micelle) according to an embodiment of the present invention.

The DMAc solution obtained in the above-described manner was used for preparation of a micelle. The DMAc solution of the drug conjugate was added dropwise to water such that the volume ratio of the solution to water was set to 1 to 10 and vortexed to prepare a micelle. This solution was dialyzed with water in a dialysis bag having a molecular cutoff (MWCO) of 3500 Da for 24 hours. The dialysis solvent was exchanged five times during the dialysis. The solution in the dialysis bag was filtered with a filter (0.22 µm) and concentrated by ultrafiltration using a 100 kDa MWCO filter membrane. The $^1$H-NMR analysis results for the obtained JQ-1-H bonded polymer micelle are shown in FIG. 35.

<Measurement of Micelle Size and PDI>

Figure 36:
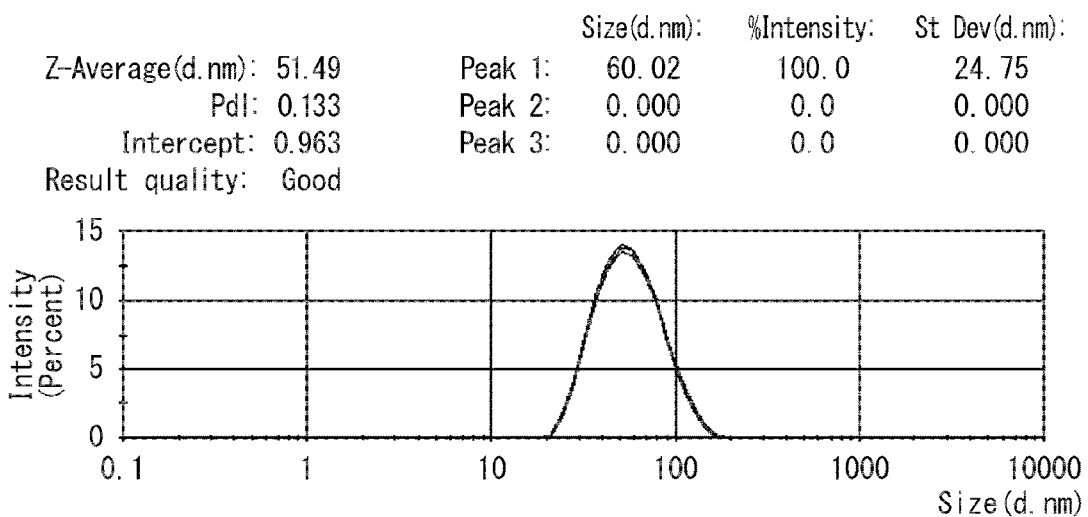
FIG. 36 shows analysis results for the polydispersion index (PDI) and the micelle size of a drug conjugate (JQ-1-H bonded aromatic polymer micelle) according to an embodiment of the present invention.
Figure 37:
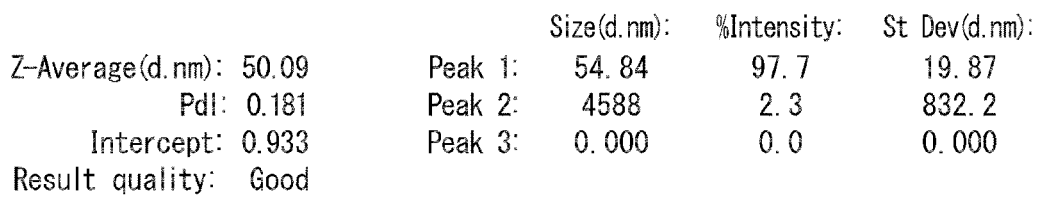
FIG. 37 shows analysis results for the polydispersion index (PDI) and the micelle size of a drug conjugate (JQ-1-H bonded aliphatic polymer micelle) according to an embodiment of the present invention.
Figure 37:
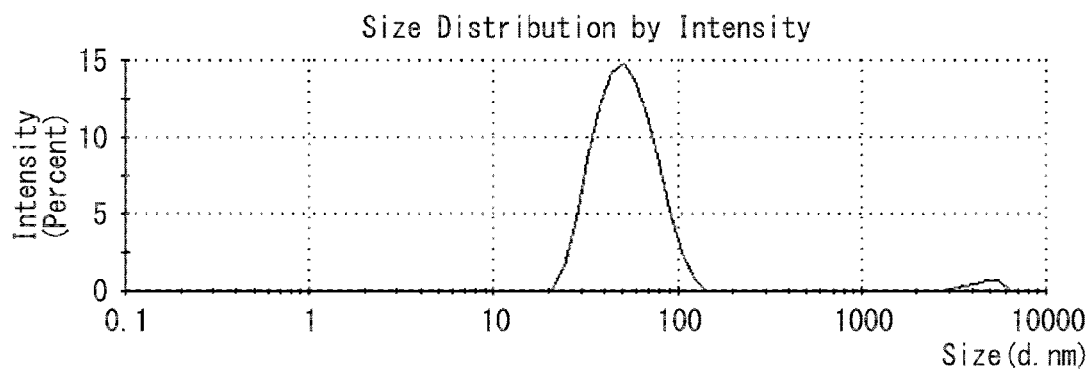

The micelle size and the polydispersion index (PDI) were acquired using a dynamic light scattering (DLS) technique. The measurement was performed using a green laser (532 nm) as an incident beam and Zetasizer nano ZS (Malvern instruments, UK) at a detection angle of 173° under a temperature condition of 25° C. The results are shown in FIGS. 36 and 37. FIG. 36 shows the micelle of the drug conjugate containing the aromatic aldehyde group-containing polymer and JQ-1-H (hereinafter, referred to as the "JQ-1-H bonded aromatic polymer micelle"). FIG. 37 shows the micelle of the drug conjugate containing the aliphatic aldehyde group-containing polymer and JQ-1-H (hereinafter, referred to as the "JQ-1-H bonded aliphatic polymer micelle").

Example 17

Cytotoxicity Test of JQ-1-H Bonded Polymer Micelle Against Lung Cancer Cells

The cytotoxicity test of the JQ-1-H bonded aromatic polymer micelle against the lung cancer cell strain H1975 and the lung cancer cell strain A549 was performed in the same manner as in Example 12. Further, the survival rate after incubation for 72 hours was confirmed by setting the concentration of H1975 to be added to 5 µg/ml and the concentration of A549 to be added to 30 µg/ml.

Figure 38:
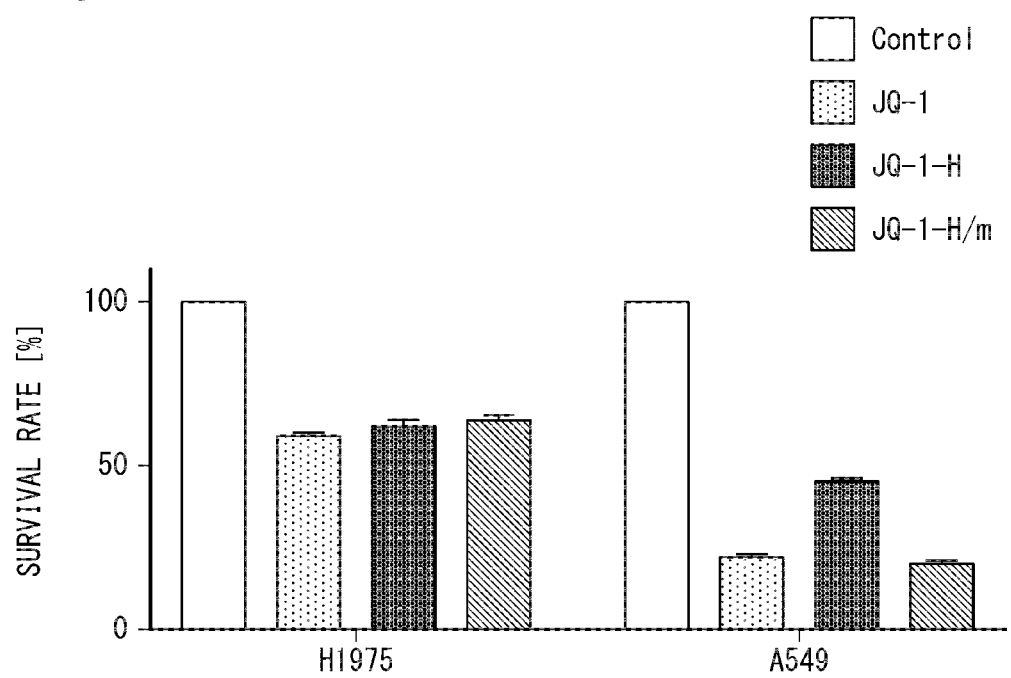
FIG. 38 is a graph showing results of a cytotoxicity test of a drug conjugate according to an embodiment of the present invention against lung cancer cells.

The results are shown in FIG. 38. Based on the results of FIG. 38, it was confirmed that the JQ1-H bonded aromatic polymer micelle exhibited the same level of cytotoxic activity as JQ1 and JQ1-H at a concentration of 5 µg/mL.

Example 18

Hot Spot Kinase Profiling of K252a-H

The kinase profiling of K252a-H was performed using Monthly 202 mutant kinase panel by entrustment with Reaction Biology Corporation. The conditions for the kinase assay are as follows. KK252a was dissolved in DMSO and the assay was performed at 100 nM.

Buffer condition: 20 mM HEPES, pH of 7.5, 10 mM $MgCl_2$, 1 mM EGTA, (in a case of being applicable, 2 mM $MnCl_2$)

ATP concentration: 10 µM

Reaction time: 2 hours

Figure 39A:
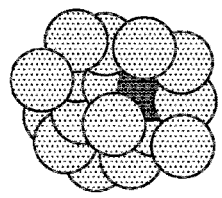
FIG. 39A is a view showing the first to third generations TKIs and the variations in resistance thereof.
Figure 39A:
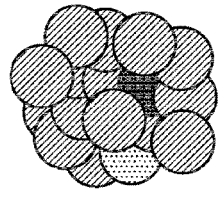
Figure 39A:
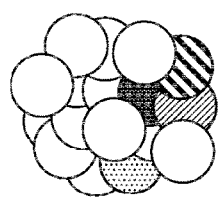
Figure 39A:
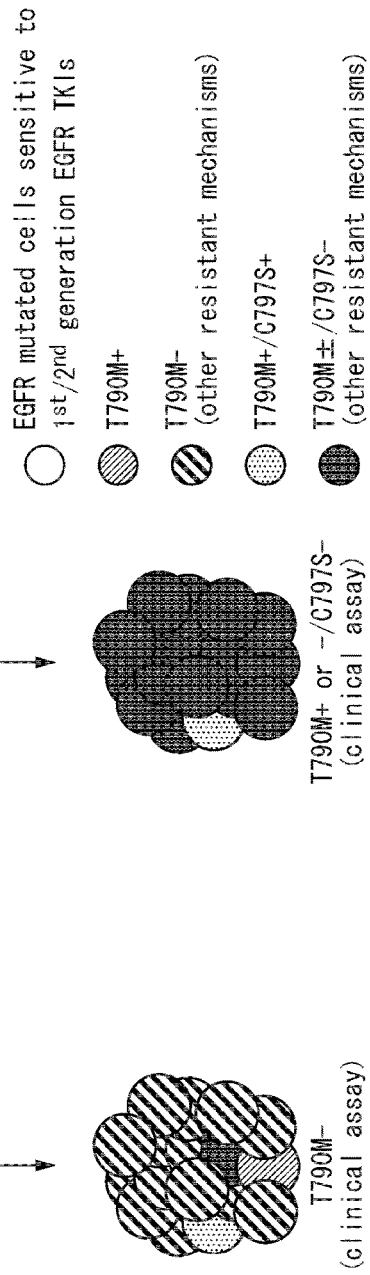
Figure 39B:
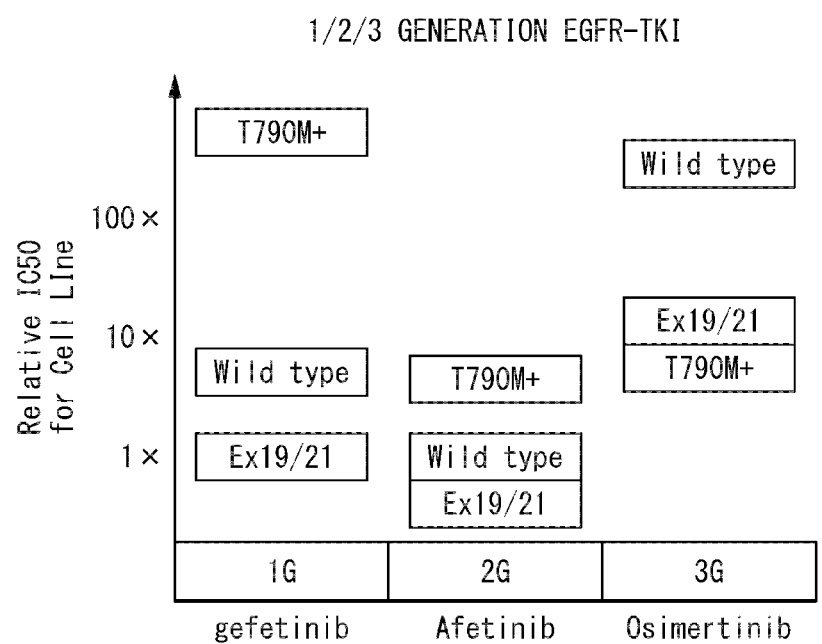
FIG. 39B is a diagram showing the first to third generations TKIs and the variations in resistance thereof.

As a reference, the first generation, the second generation, and the third generation of tyrosine kinase inhibitors (TKI) and the resistant mutations are shown in FIGS. 39A and 39B. As shown in FIGS. 39A and 39B, since the first to third generation TKIs are not effective for a C797S mutation, a TKI which is effective for the C797S mutation is required.

Figure 40:
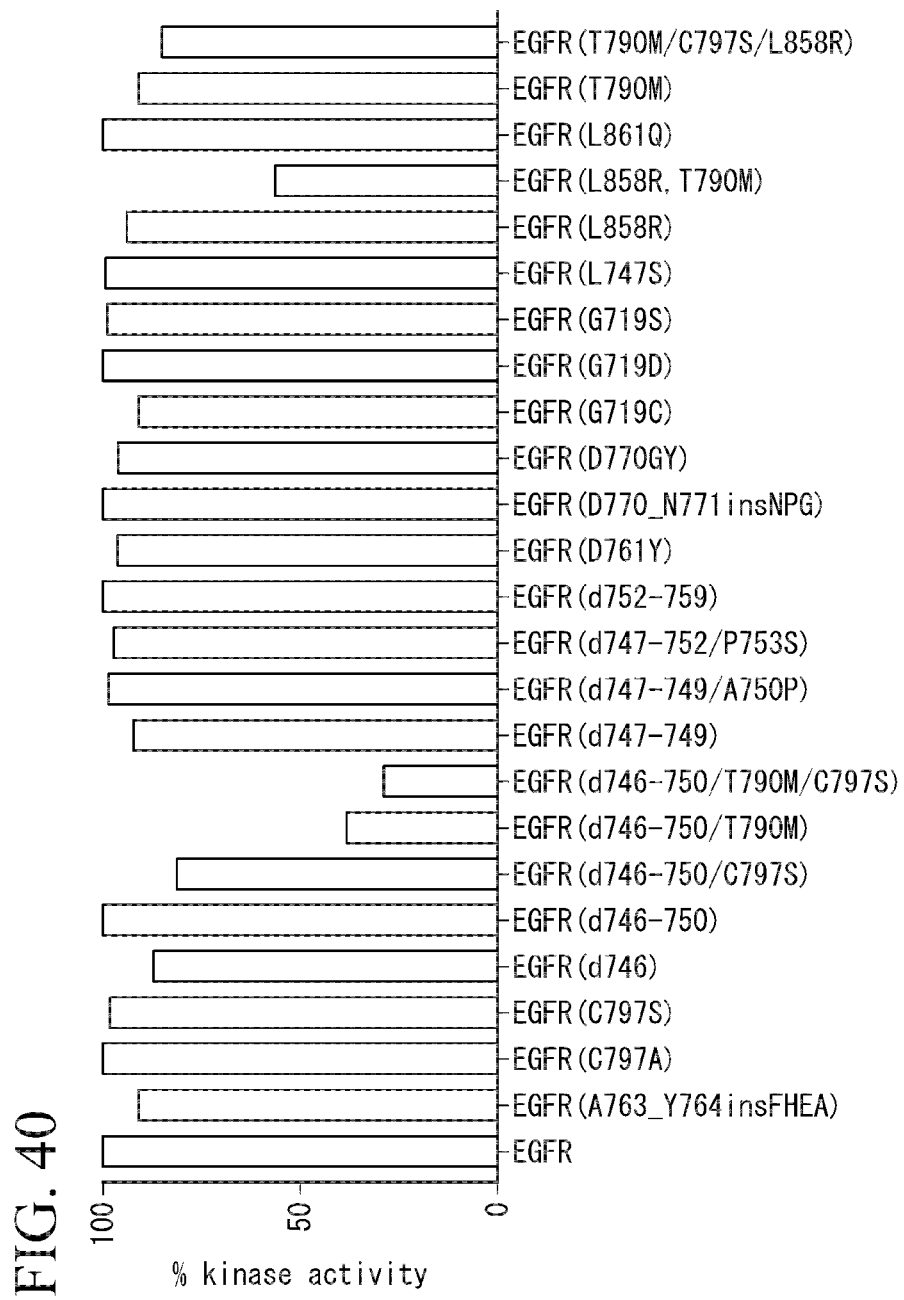
FIG. 40 is a diagram showing kinase assay results of K252a-H with respect to an EGFR mutation.

The kinase assay results of K252a-H against an EGFR mutation are shown in FIG. 40. As shown in FIG. 40, K252a-H exhibits specifically high activity against gatekeeper mutations (such as d746-750/T790M, d746-750/T790M/C797S, L858R, and T790M) in which many TKIs do not exhibit effectiveness.

Figure 41A:
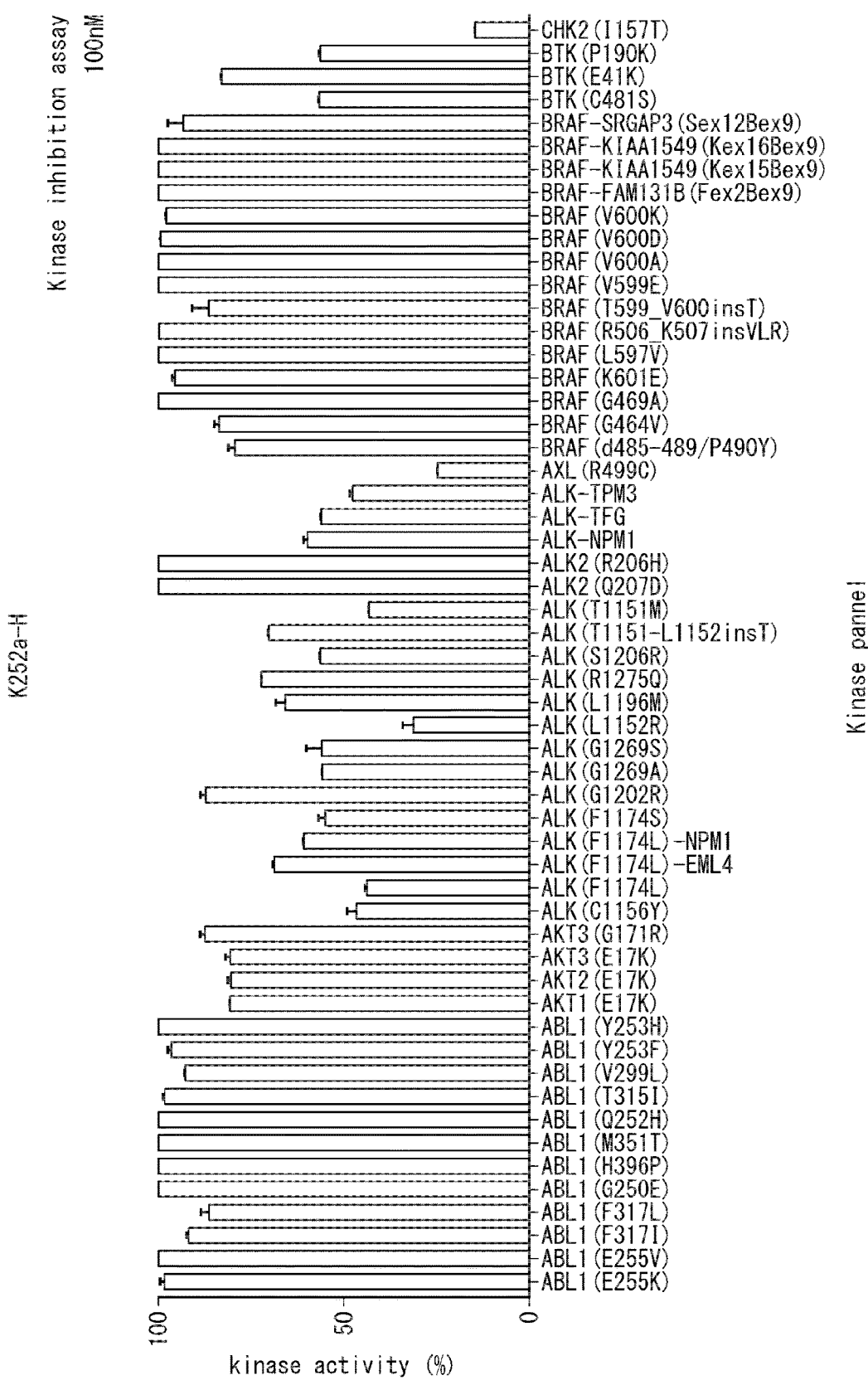
FIG. 41A is a diagram showing kinase profiling results.
Figure 41B:
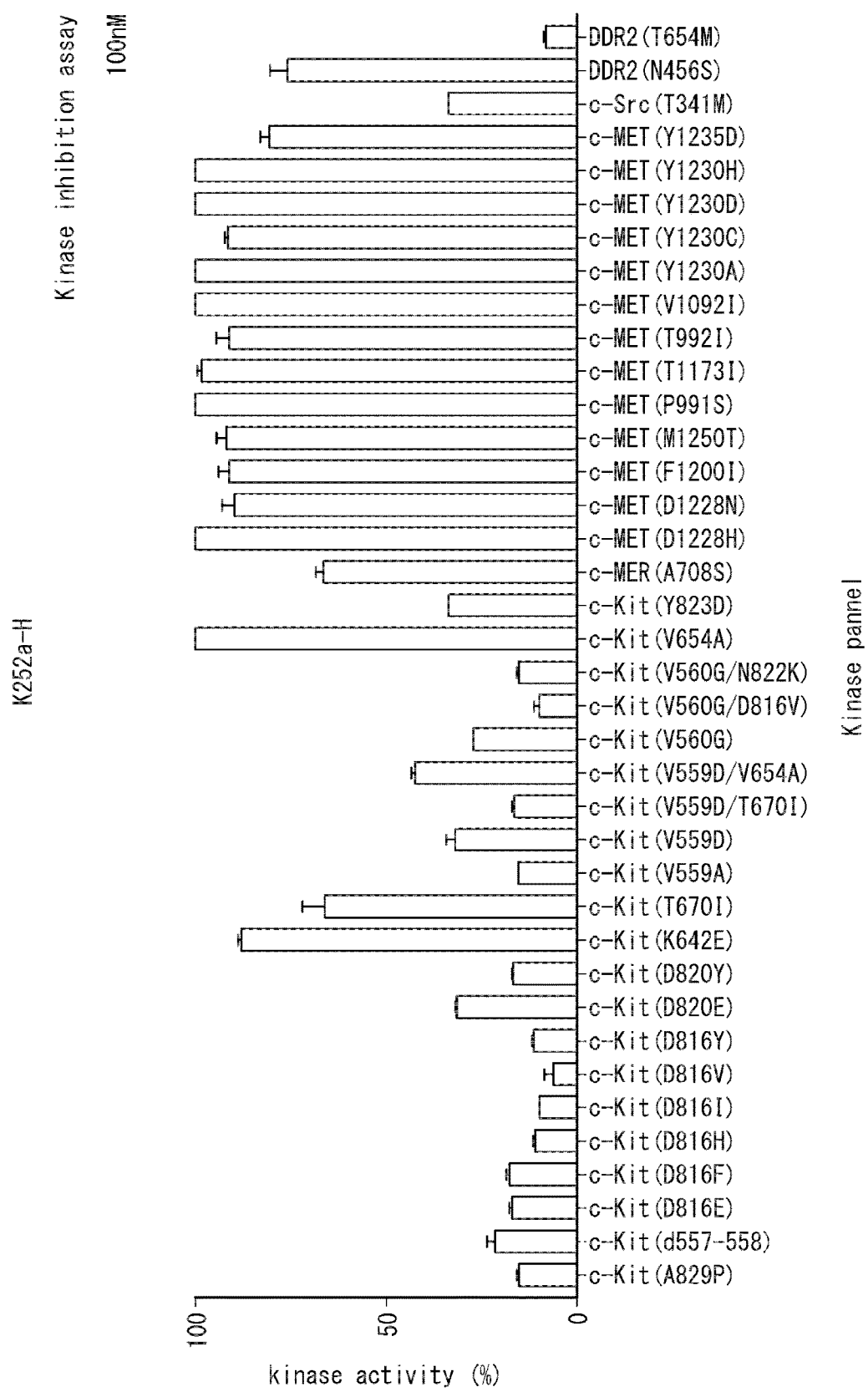
FIG. 41B is a diagram showing kinase profiling results.
Figure 41C:
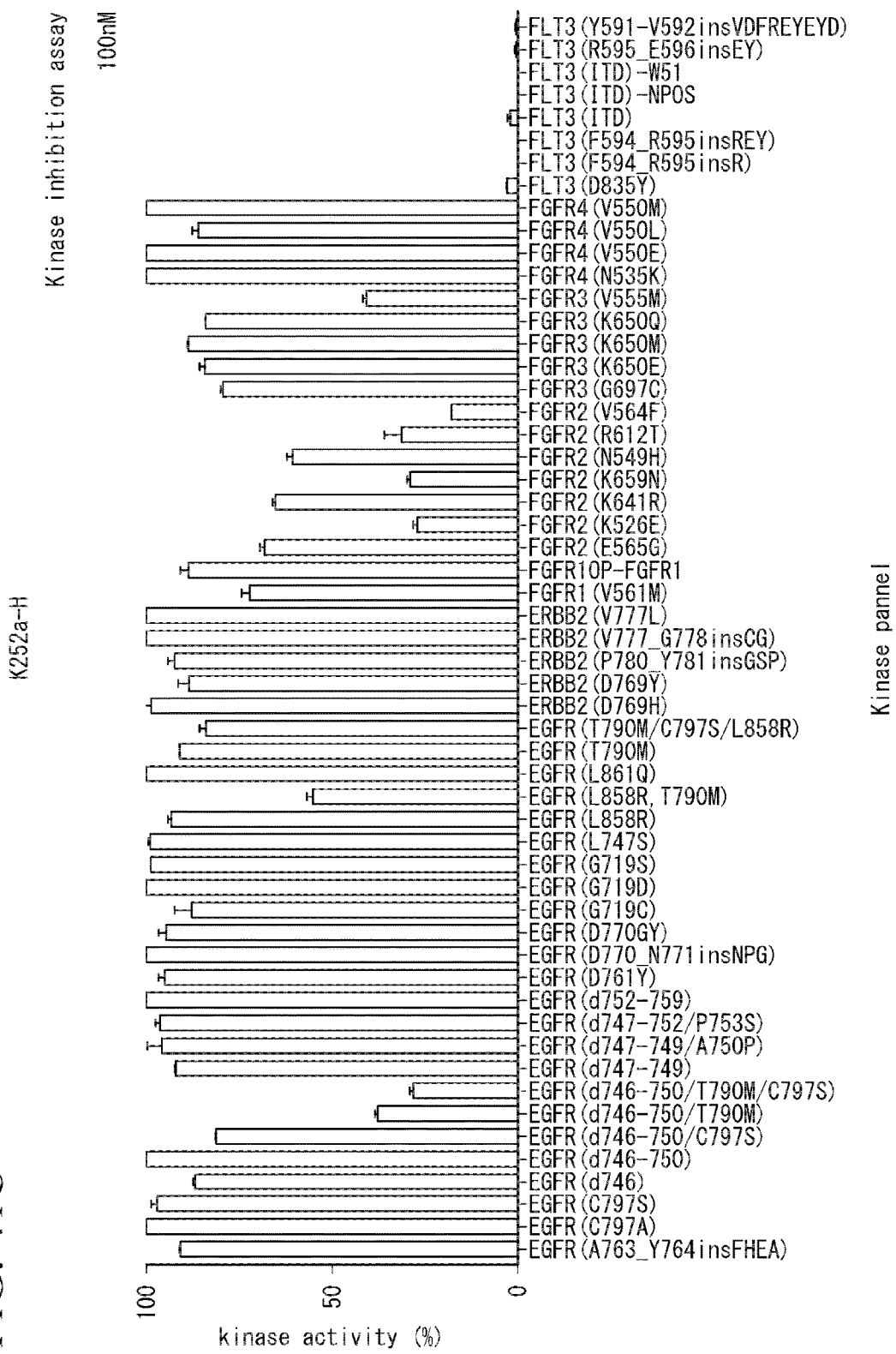
FIG. 41C is a diagram showing kinase profiling results.

The results of kinase profiling are shown in FIGS. 41A to 41C. FIG. 42 shows the results of kinase profiling for K252a-H and a list of mutant kinases whose kinase activity was suppressed to 30% or less. K252a-H was confirmed to be a strong inhibitor for oncogene c-kit/Flt3/RET.

The invention claimed is:

1. A polymer comprising:
   a repeating unit (I) represented by Formula (I); and
   a repeating unit (II) represented by Formula (II)

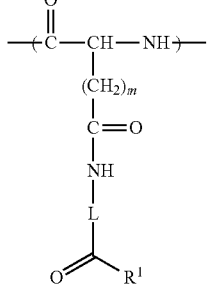
(I)

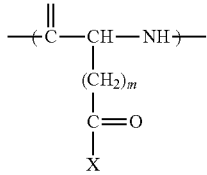
(II)

wherein, m represents 1 or 2, L represents a divalent aromatic hydrocarbon group or a divalent aliphatic hydrocarbon group, $R^1$ represents a hydrogen atom, an aliphatic hydrocarbon group, or an aromatic hydrocarbon group, X represents $OR^x$, $SR^x$, or $NR^{x1}R^{x2}$, $R^x$ represents a hydrogen atom, an aliphatic hydrocarbon group, or an aromatic hydrocarbon group, $R^{x1}$ and $R^{x2}$ each independently represent a hydrogen atom, an aliphatic hydrocarbon group, or an aromatic hydrocarbon group.

2. A method for producing a polymer, comprising:
   a step (1) of reacting a polymer (P1) which has a repeating unit (II') represented by Formula (II') with a compound (1a) represented by Formula (1a) to obtain a polymer (P2) which has a repeating unit represented by Formula (I') and the repeating unit (II'); and
   a step (2) of hydrolyzing the polymer (P2) under a neutral condition or an acidic condition to obtain a polymer which has a repeating unit (I) represented by Formula (I) and a repeating unit (II-1) represented by Formula (II-1)

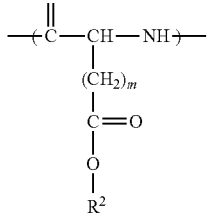
(II')

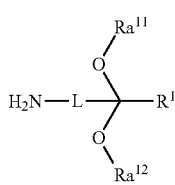
(1a)

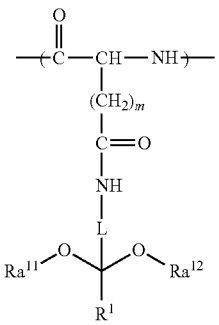
(I')

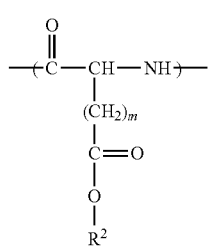
(II')

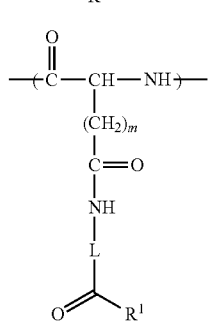
(I)

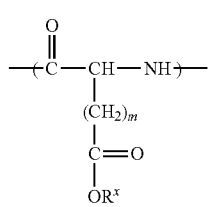
(II-1)

wherein m represents 1 or 2, $R^2$ represents a hydrogen atom, an aliphatic hydrocarbon group, or an aromatic hydrocarbon group, L represents a divalent aromatic hydrocarbon group, or a divalent aliphatic hydrocarbon group, $R^1$ represents a hydrogen atom, an aliphatic hydrocarbon group, or an aromatic hydrocarbon group, $Ra^{11}$ and $Ra^{12}$ each independently represent a methyl group or an ethyl group or $Ra^{11}$ and $Ra^{12}$ are bonded to each other and represent an ethylene group or a propylene group, and $R^x$ represents a hydrogen atom, an aliphatic hydrocarbon group, or an aromatic hydrocarbon group.

3. A method for producing a polymer, comprising:
   a step (1) of reacting a polymer (P1) which has a repeating unit (II') represented by Formula (II') with a compound (1a) represented by Formula (1a) to obtain a polymer (P2) which has a repeating unit represented by Formula (I') and the repeating unit (II');
   a step (2a) of applying at least one treatment selected from the group consisting of hydrolysis under an alkaline condition, a transesterification reaction, aminolysis, and hydrolysis and amide coupling under an alkaline condition to the polymer (P2) to obtain a polymer (P3) which has a repeating unit (I') represented by Formula (I') and a repeating unit (II) represented by Formula (II); and a step (2b) of hydrolyzing the polymer (P3) under a neutral condition or an acidic condition to obtain a polymer which has a repeating unit (I) represented by Formula (I) and a repeating unit (II) represented by Formula (II)

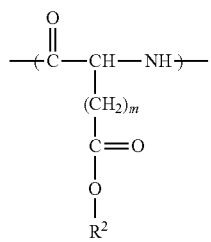
(II')

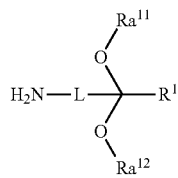
(1a)

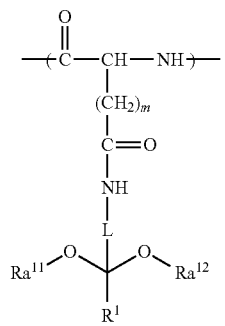
(I')

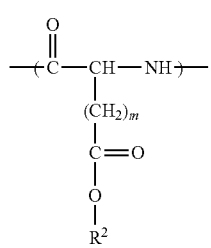
(II')

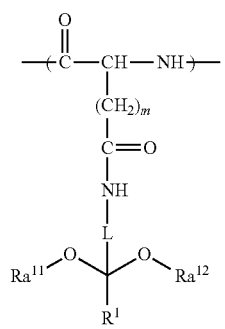
(I')

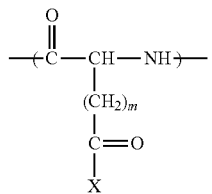
(II)

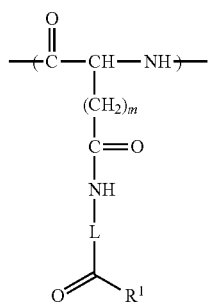
(I)

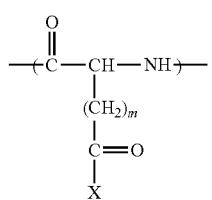
(II)

wherein m represents 1 or 2, $R^2$ represents a hydrogen atom, an aliphatic hydrocarbon group, or an aromatic hydrocarbon group, L represents a divalent aromatic hydrocarbon group, or a divalent aliphatic hydrocarbon group, $R^1$ represents a hydrogen atom, an aliphatic hydrocarbon group, or an aromatic hydrocarbon group, $Ra^{11}$ and $Ra^{12}$ each independently represent a methyl group or an ethyl group or $Ra^{11}$ and $Ra^{12}$ are bonded to each other and represent an ethylene group or a propylene group, X represents $OR^x$, $SR^x$, or $NR^{x1}R^{x2}$, $R^x$ represents a hydrogen atom, an aliphatic hydrocarbon group, or an aromatic hydrocarbon group, and $R^{x1}$ and $R^{x2}$ each independently represent a hydrogen atom, an aliphatic hydrocarbon group, or an aromatic hydrocarbon group.

4. A drug conjugate comprising:
   the polymer according to claim 1; and
   at least one drug bonded to the polymer.

5. The drug conjugate according to claim 4, comprising:
   a polymer which includes a repeating unit (Ia) represented by Formula (Ia) and a repeating unit (II) represented by Formula (II)

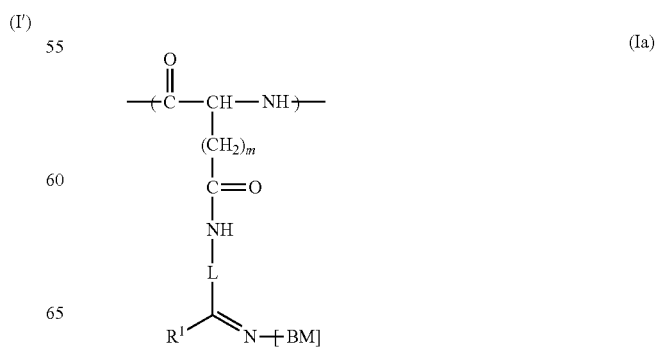
(Ia)

-continued

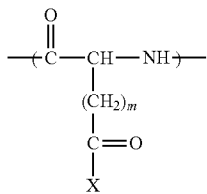
(II)

wherein m represents 1 or 2, L represents a divalent aromatic hydrocarbon group or a divalent aliphatic hydrocarbon group, $R^1$ represents a hydrogen atom, an aliphatic hydrocarbon group, or an aromatic hydrocarbon group, BM represents an active molecule, X represents $OR^x$, $SR^x$, or $NR^{x1}R^{x2}$, $R^x$ represents a hydrogen atom, an aliphatic hydrocarbon group, or an aromatic hydrocarbon group, $R^{x1}$ and $R^{x2}$ each independently represent a hydrogen atom, an aliphatic hydrocarbon group, or an aromatic hydrocarbon group.

6. A micelle comprising:
the drug conjugate according to claim 5.

7. A pharmaceutical composition comprising the drug conjugate according to claim 4.

8. A pharmaceutical composition comprising the drug conjugate according to claim 5.

9. A pharmaceutical composition comprising the micelle according to claim 6.

10. A method of treating tumors in a patient, comprising:
administering to the patient the drug conjugate according to claim 4.

11. A method of treating tumors in a patient, comprising:
administering to the patient the drug conjugate according to claim 5.

12. A method of treating tumors in a patient, comprising:
administering to the patient the micelle according to claim 6.

* * * * *